United States Patent
Masukawa et al.

(10) Patent No.: US 9,663,716 B2
(45) Date of Patent: *May 30, 2017

(54) TETRAHYDROPYRAN COMPOUND, LIQUID CRYSTAL COMPOSITION AND LIQUID CRYSTAL DISPLAY DEVICE

(75) Inventors: Tokifumi Masukawa, Chiba (JP); Kenji Hirata, Chiba (JP); Junichi Yamashita, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 52 days.

This patent is subject to a terminal disclaimer.

(21) Appl. No.: 13/390,930
(22) PCT Filed: Aug. 10, 2010
(86) PCT No.: PCT/JP2010/063530
§ 371 (c)(1),
(2), (4) Date: Feb. 16, 2012
(87) PCT Pub. No.: WO2011/021534
PCT Pub. Date: Feb. 24, 2011

(65) Prior Publication Data
US 2012/0145958 A1 Jun. 14, 2012

(30) Foreign Application Priority Data
Aug. 19, 2009 (JP) ................. 2009-190184

(51) Int. Cl.
C09K 19/34 (2006.01)
C07D 309/06 (2006.01)
C07D 405/04 (2006.01)
C07D 309/02 (2006.01)
C07D 405/10 (2006.01)
C09K 19/04 (2006.01)

(52) U.S. Cl.
CPC ........ C09K 19/3402 (2013.01); C07D 309/02 (2013.01); C07D 309/06 (2013.01); C07D 405/04 (2013.01); C07D 405/10 (2013.01); C09K 2019/0407 (2013.01); C09K 2019/3422 (2013.01)

(58) Field of Classification Search
CPC . C09K 19/3402; C07D 309/06; C07D 405/04
See application file for complete search history.

(56) References Cited

U.S. PATENT DOCUMENTS

| 5,279,764 A | 1/1994 | Reiffenrath et al. | |
|---|---|---|---|
| 5,856,152 A * | 1/1999 | Wilson ............... | C07K 14/4712 435/320.1 |
| 7,510,749 B2 * | 3/2009 | Shimada ............ | C09K 19/3098 252/299.61 |
| 8,097,309 B2 * | 1/2012 | Kawasaki .......... | C09K 19/3028 252/299.61 |
| 8,124,197 B2 * | 2/2012 | Saito .................. | C09K 19/3001 252/299.61 |
| 8,158,219 B2 * | 4/2012 | Hattori ............... | C09K 19/12 252/299.61 |

(Continued)

FOREIGN PATENT DOCUMENTS

| EP | 0967261 | 12/1999 |
|---|---|---|
| GB | 2478451 | 9/2011 |

(Continued)

OTHER PUBLICATIONS

English Translation of JP2008214199.*

(Continued)

*Primary Examiner* — Cynthia H Kelly
*Assistant Examiner* — Anna Malloy
(74) *Attorney, Agent, or Firm* — Jianq Chyun IP Office

(57) ABSTRACT

A compound represented by formula (1-1) or (1-2) is provided.

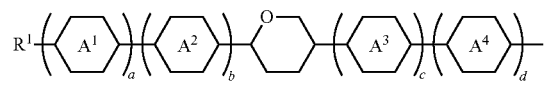

(1-1)

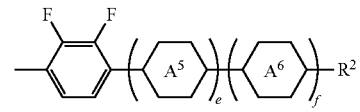

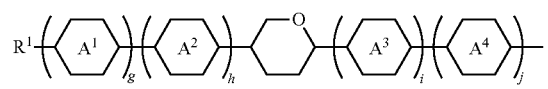

(1-2)

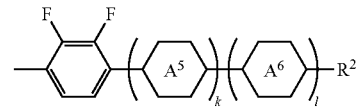

For example, $R^1$ and $R^2$ are independently hydrogen, alkyl having 1 to 10 carbons or alkoxy having 1 to 9 carbons; the ring $A^1$, the ring $A^2$, the ring $A^3$, the ring $A^4$, the ring $A^5$ and the ring $A^6$ are independently 1,4-cyclohexylene or 1,4-phenylene; a, b, c, d, e and f are independently 0 or 1, and the sum of a, b, c, d, e and f is 2; and g, h, i, j, k and l are independently 0 or 1, and the sum of g, h, i, j, k and l is 2.

23 Claims, No Drawings

(56) References Cited

U.S. PATENT DOCUMENTS

| | | | | |
|---|---|---|---|---|
| 8,206,795 B2* | 6/2012 | Saito | ............... | C09K 19/3402 |
| | | | | 252/299.61 |
| 8,211,512 B2* | 7/2012 | Saito | ............... | C09K 19/3003 |
| | | | | 252/299.01 |
| 8,273,421 B2* | 9/2012 | Saito | ............... | C09K 19/3003 |
| | | | | 252/299.61 |
| 8,337,964 B2* | 12/2012 | Yamashita | ......... | C09K 19/3402 |
| | | | | 252/299.61 |
| 8,357,436 B2* | 1/2013 | Saito | ............... | C09K 19/3003 |
| | | | | 252/299.61 |
| 8,361,344 B2* | 1/2013 | Yanai | ............... | C09K 19/3001 |
| | | | | 252/299.01 |
| 8,394,468 B2* | 3/2013 | Ito | ............... | C09K 19/12 |
| | | | | 252/299.61 |
| 8,398,886 B2* | 3/2013 | Yanai | ............... | C09K 19/3028 |
| | | | | 252/299.01 |
| 8,404,317 B2* | 3/2013 | Saito | ............... | C09K 19/16 |
| | | | | 252/299.61 |
| 8,535,768 B2* | 9/2013 | Saito | ............... | C09K 19/12 |
| | | | | 252/299.01 |
| 8,580,142 B2* | 11/2013 | Shimada | ............... | C09K 19/20 |
| | | | | 252/299.01 |
| 8,632,696 B2* | 1/2014 | Saito | ............... | C09K 19/3001 |
| | | | | 252/299.01 |
| 8,637,125 B2* | 1/2014 | Goto | ............... | C07C 22/00 |
| | | | | 252/299.01 |
| 8,703,012 B2* | 4/2014 | Furusato | ............ | C09K 19/3001 |
| | | | | 252/299.01 |
| 8,741,397 B2* | 6/2014 | Hattori | ............... | C08F 2/50 |
| | | | | 252/299.4 |
| 8,900,479 B2* | 12/2014 | Furusato | ............ | C09K 19/322 |
| | | | | 252/299.01 |
| 8,916,063 B2* | 12/2014 | Goto | ............... | C09K 19/12 |
| | | | | 252/299.61 |
| 8,956,552 B2* | 2/2015 | Sasada | ............... | C09K 19/3098 |
| | | | | 252/299.63 |
| 8,962,105 B2* | 2/2015 | Furusato | ............ | C09K 19/3402 |
| | | | | 252/299.01 |
| 8,968,597 B2* | 3/2015 | Furusato | ............... | C09K 19/56 |
| | | | | 252/299.6 |
| 9,045,684 B2* | 6/2015 | Gotoh | ............... | C09K 19/3402 |
| 9,062,250 B2* | 6/2015 | Ito | ............... | C09K 19/3003 |
| 9,074,132 B2* | 7/2015 | Gotoh | ............... | C09K 19/14 |
| 9,102,869 B2* | 8/2015 | Furusato | ............ | C09K 19/3003 |
| 9,139,672 B2* | 9/2015 | Fujita | ............... | C08F 20/20 |
| 9,150,787 B2* | 10/2015 | Gotoh | ............... | C09K 19/3402 |
| 2002/0038858 A1* | 4/2002 | Kato et al. | ............. | 252/299.63 |
| 2004/0065866 A1* | 4/2004 | Kato | ............... | C07C 17/2635 |
| | | | | 252/299.61 |
| 2009/0091703 A1* | 4/2009 | Matsumura et al. | ......... | 349/186 |
| 2010/0309402 A1 | 12/2010 | Kobayashi et al. | | |
| 2011/0090450 A1 | 4/2011 | Kobayashi | | |
| 2011/0147658 A1 | 6/2011 | Saito et al. | | |

FOREIGN PATENT DOCUMENTS

| | | | |
|---|---|---|---|
| JP | 02-004725 | | 1/1990 |
| JP | 10-237448 | | 9/1998 |
| JP | 2000-008040 | | 1/2000 |
| JP | 2008214199 A | * | 9/2008 |
| WO | 89/08633 | | 9/1989 |
| WO | 2009/031437 | | 3/2009 |
| WO | 2009/150966 | | 12/2009 |
| WO | WO 2009150966 A1 | * | 12/2009 |
| WO | 2010/032587 | | 3/2010 |
| WO | WO 2010029843 A1 * | 3/2010 | ......... C09K 19/3402 |
| WO | WO 2010032612 A1 * | 3/2010 | ............ C09K 19/12 |
| WO | WO 2010044334 A1 * | 4/2010 | ......... C09K 19/3003 |
| WO | WO 2010070979 A1 * | 6/2010 | ......... C09K 19/3402 |
| WO | 2010/082558 | | 7/2010 |
| WO | WO 2010084823 A1 * | 7/2010 | ............ C09K 19/12 |

OTHER PUBLICATIONS

English Translation of WO2009150966.*

F. M. Leslie, "Distortion of Twisted Orientation Patterns in Liquid Crystals by Magnetic Fields", Molecular Crystals and Liquid Crystals, 1970, pp. 57-72, vol. 12.

* cited by examiner

TETRAHYDROPYRAN COMPOUND, LIQUID CRYSTAL COMPOSITION AND LIQUID CRYSTAL DISPLAY DEVICE

CROSS-REFERENCE TO RELATED APPLICATION

This application is a 371 of international application of PCT application serial no. PCT/JP2010/063530, filed on Aug. 10, 2010, which claims the priority benefit of Japan application no. 2009-190184, filed on Aug. 19, 2009. The entirety of each of the above-mentioned patent applications is hereby incorporated by reference herein and made a part of this specification.

TECHNICAL FIELD

The invention relates to a new liquid crystal compound and a liquid crystal composition. More specifically, it relates to a liquid crystal compound in which the dielectric anisotropy ($\Delta\epsilon$) is negative, a liquid crystal composition including this compound and a liquid crystal display device containing this liquid crystal composition.

TECHNICAL BACKGROUND

A display device utilizing a liquid crystal compound (in this patent application, a liquid crystal compound is used as a generic term for a compound that exhibits a liquid crystal phase and a compound that exhibits no liquid crystal phases but useful as a component of a liquid crystal composition) has been widely used for the display of a watch, a calculator, a word processor or the like. The display device utilizes the refractive index anisotropy ($\Delta n$), the dielectric anisotropy ($\Delta\epsilon$) and so forth of the liquid crystal compound.

A liquid crystal phase includes a nematic liquid crystal phase, a smectic liquid crystal phase and a cholesteric liquid crystal phase, and the nematic liquid crystal phase is most widely applied. A display mode includes a DS (dynamic scattering) mode, a DAP (deformation of aligned phases) mode, a GH (guest-host) mode, a TN (twisted nematic) mode, a STN (super twisted nematic) mode, a TFT (thin film transistor) mode, a VA (vertical alignment) mode, an IPS (in-plane switching) mode and a PSA (polymer sustained alignment) mode.

A liquid crystal compound used for these display modes is required to exhibit a liquid crystal phase in a wide temperature range, centering at room temperature, to be sufficiently stable under conditions in which the display device is used, and also to have sufficient characteristics for driving the display device. However, no single liquid crystal compound that satisfies these conditions has been found until now.

The actual situation is that a liquid crystal composition is prepared by mixing from several to several tens of liquid crystal compounds in order to satisfy the required characteristics. It is required that the liquid crystal composition is stable to moisture, light, heat and air, which are normally present under conditions in which the display device is used, and is stable to an electric field or electromagnetic radiation, and is also stable chemically to a compound that will be mixed. It is required that the liquid crystal composition has suitable values of a variety of physical properties such as refractive index anisotropy ($\Delta n$) and dielectric anisotropy ($\Delta\epsilon$), depending on the display mode or the shape of the display device. Furthermore, it is important that each component in the liquid crystal composition has an excellent solubility in each other.

In recent years, modes such as IPS, VA, OCB and PSA among the display modes have been receiving attention as a display mode capable of overcoming a narrow viewing angle of a liquid crystal display device, which is the greatest subject to be solved. In liquid crystal display devices having these modes, a liquid crystal display device, especially having the VA mode or the IPS mode, has been studied earnestly, since it has an excellent responsivity in addition to a wide viewing angle, and is capable of providing a high-contrast display. The liquid crystal composition used in the liquid crystal display devices having these display modes is characterized by the negative dielectric anisotropy ($\Delta\epsilon$). It is known that a liquid crystal composition having a large negative dielectric anisotropy ($\Delta\epsilon$) can decrease the driving voltage of a liquid crystal display device containing the liquid crystal composition (Non-patent document No. 1). Accordingly, liquid crystal compounds as the components of the liquid crystal composition are also required to have a larger negative dielectric anisotropy ($\Delta\epsilon$).

A variety of liquid crystal compounds in which lateral hydrogen on the benzene ring had been replaced by fluorine have conventionally been studied as a component of a liquid crystal composition having negative dielectric anisotropy (Patent documents No. 1 and No. 2). For example, a compound represented by formula (a) has been reported (hereinafter, it may be abbreviated to the compound (a); the same applies to a compound represented by another formula, giving a term such as compound (1-1)). However, the compound (a) did not always have a large value although it had negative dielectric anisotropy ($\Delta\epsilon$) and the value might not be sufficiently large for decreasing the driving voltage of a liquid crystal display device having a VA mode, an IPS mode or the like.

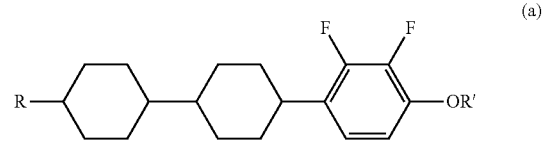

(a)

In formula (a), R and R' are alkyl.

Thus, in a compound having a 2,3-difluorophenylene moiety, attempts have been made to increase the absolute value of negative dielectric anisotropy ($\Delta\epsilon$). For example, a compound having the 2,3-difluorophenylene moiety, to which a tetrahydropyran-2,5-diyl moiety is introduced has been reported (Patent document No. 3). The compound (b) has a large negative dielectric anisotropy ($\Delta\epsilon$) in comparison with the compound (a).

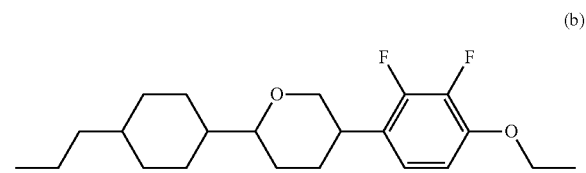 [SMILES: CCCC1CCC(C2CCC(c3ccc(OCC)c(F)c3F)CO2)CC1]

(b)

On the other hand, a liquid crystal composition having a wide temperature range of a nematic phase has been requested along with an increased use of a liquid crystal display device, and thus a liquid crystal compound having a high clearing point has been requested. There is generally a tendency to increase the viscosity of a liquid crystal compound as the clearing point increases. However, a low viscosity is desirable in order to achieve a high response speed in the liquid crystal composition. Because of this point of view, a liquid crystal compound having a large negative dielectric anisotropy (Δε) and having both a high clearing point and a low viscosity has been expected.

PRIOR ART

Patent Document

Patent document No. 1: JP 2811342 B (1998).
Patent document No. 2: JP H02-004725 (1990)
Patent document No. 3: JP 2000-008040 (2000). .

Non-Patent Document

Non-Patent Document No. 1: Mol. Cryst. Liq. Cryst., 12, (1970).

OUTLINE OF THE INVENTION

Subject to be Solved by the Invention

The first aim of the invention is to provide a liquid crystal compound not only having a large negative dielectric anisotropy (Δε), a high clearing point and a low viscosity, but also having at least one of characteristics such as stability to heat, light or the like, a suitable refractive index anisotropy (Δn), a large negative dielectric anisotropy (Δε) and an excellent compatibility with other liquid crystal compounds.

The second aim of the invention is to provide a liquid crystal composition including the compound and having at least one of characteristics such as a low viscosity, a suitable refractive index anisotropy (Δn), a suitable negative dielectric anisotropy (Δε), a low threshold voltage, a high maximum temperature of a nematic phase (the phase transition temperature between a nematic phase and an isotropic phase) and a low minimum temperature of a nematic phase, or having a suitable balance between at least two of the characteristics.

The third aim of the invention is to provide a liquid crystal display device containing the composition and having at least one of characteristics such as a short response time, low power consumption, a low driving voltage, a large contrast and a wide temperature range in which the device can be used, or having a suitable balance between at least two of the characteristics.

Means for Solving the Subject

As a result of earnest research on these subjects, the inventors have found that a compound having a specific structure, that is to say, having a tetrahydropyran ring and a 2,3-fluorophenylene ring especially had an excellent effect exhibiting a large negative dielectric anisotropy (Δε) and exhibiting both a high clearing point and a low viscosity. Moreover, it was found that the subjects could be solved by applying the effect, and thus the invention has completed.

That is to say, the invention includes a structure such as items 1 to 31.

Item 1. A compound represented by formula (1-1) or (1-2).

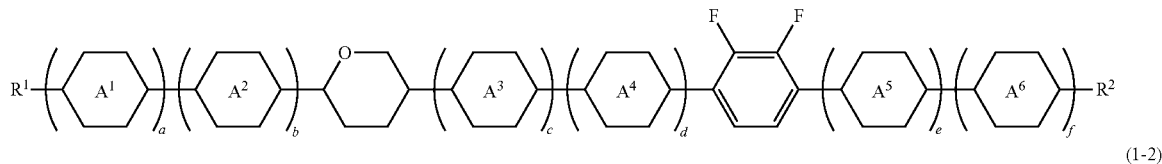

(1-1)

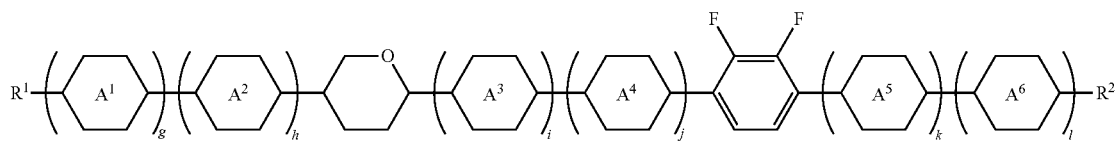

(1-2)

In formulas (1-1) and (1-2), $R^1$ and $R^2$ are independently hydrogen, alkyl having 1 to 10 carbons or alkoxy having 1 to 9 carbons;

the ring $A^1$, the ring $A^2$, the ring $A^3$, the ring $A^4$, the ring $A^5$ and the ring $A^6$ are independently 1,4-cyclohexylene or 1,4-phenylene, and in the 1,4-cyclohexylene arbitrary —$CH_2$— may be replaced by —O— and arbitrary —$(CH_2)_2$— may be replaced by —CH=CH—, and in the 1,4-phenylene arbitrary —CH= may be replaced by —N=;

a, b, c, d, e and f are independently 0 or 1, and the sum of a, b, c, d, e and f is 2;

g, h, i, j, k and l are independently 0 or 1, and the sum of g, h, i, j, k and l is 2; and in formula (1-2), the ring $A^2$ is 1,4-cyclohexenylene, 2-fluoro-1,4-phenylene, 3-fluoro-1,4-phenylene, 2,3-difluoro-1,4-phenylene, tetrahydropyran-2,5-diyl, tetrahydropyran-3,6-diyl, 1,3-dioxane-2,5-diyl, pyrimidine-2,5-diyl, pyrimidine-3,6-diyl, pyridine-2,5-diyl or pyridine-3,6-diyl, when g and h are 1, i, j, k and l are 0, and the ring $A^1$ is 1,4-cyclohexylene or 1,4-cyclohexenylene.

Item 2. The compound according to item 1, wherein in formulas (1-1) and (1-2) according to item 1, $R^1$ and $R^2$ are independently hydrogen, alkyl having 1 to 10 carbons or alkoxy having 1 to 9 carbons; and the ring $A^1$, the ring $A^2$, the ring $A^3$, the ring $A^4$, the ring $A^5$ and the ring $A^6$ are independently 1,4-cyclohexylene, 1,4-cyclohexenylene, 1,4-phenylene, tetrahydropyran-2,5-diyl, tetrahydropyran-3,6-diyl, 1,3-dioxane-2,5-diyl, pyrimidine-2,5-diyl, pyrimidine-3,6-diyl, pyridine-2,5-diyl or pyridine-3,6-diyl.

Item 3. The compound according to item 2, wherein in formulas (1-1) and (1-2) according to item 1, $R^1$ is alkyl having 1 to 10 carbons, and $R^2$ is alkoxy having 1 to 9 carbons.

Item 4. The compound according to item 2, wherein in formulas (1-1) and (1-2) according to item 1, $R^1$ and $R^2$ are independently alkyl having 1 to 10 carbons.

Item 5. The compound according to any one of items 2 to 4, wherein in formula (1-2) according to item 1, at least one of i and j is 1.

Item 6. A compound represented by formula (1-1-1).

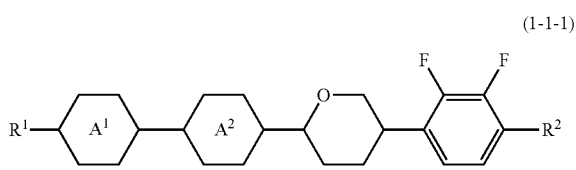

(1-1-1)

In formula (1-1-1), $R^1$ and $R^2$ are independently hydrogen, alkyl having 1 to 10 carbons or alkoxy having 1 to 9 carbons; and the ring $A^1$ and the ring $A^2$ are independently 1,4-cyclohexylene, 1,4-cyclohexenylene, 1,4-phenylene, 1,3-dioxane-2,5-diyl, pyrimidine-2,5-diyl, pyrimidine-3,6-diyl, pyridine-2,5-diyl or pyridine-3,6-diyl.

Item 7. The compound according to item 6, wherein in formula (1-1-1) according to item 6, the ring $A^1$ and the ring $A^2$ are 1,4-cyclohexylene.

Item 8. A compound represented by formula (1-1-2) or (1-2-2).

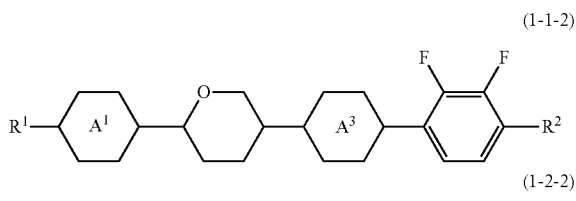

(1-1-2)

(1-2-2)

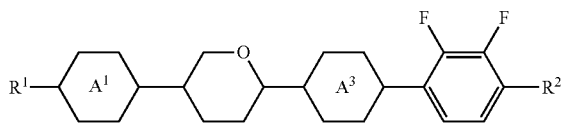

In formulas (1-1-2) and (1-2-2), $R^1$ and $R^2$ are independently hydrogen, alkyl having 1 to 10 carbons or alkoxy having 1 to 9 carbons; and the ring $A^1$ and the ring $A^3$ are independently 1,4-cyclohexylene, 1,4-cyclohexenylene, 1,4-phenylene, 1,3-dioxane-2,5-diyl, pyrimidine-2,5-diyl, pyrimidine-3,6-diyl, pyridine-2,5-diyl or pyridine-3,6-diyl.

Item 9. The compound according to item 8, wherein in formulas (1-1-2) and (1-2-2) according to item 8, the ring $A^1$ and the ring $A^3$ are 1,4-cyclohexylene.

Item 10. A compound represented by formula (1-1-3) or (1-2-3).

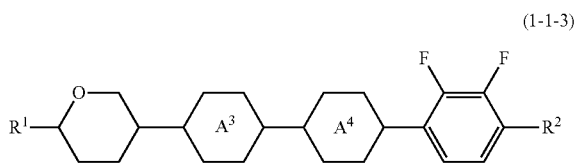

(1-1-3)

(1-2-3)

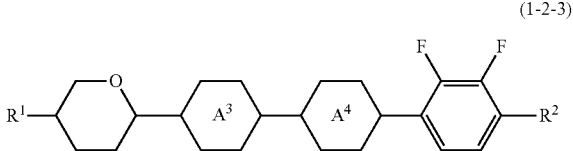

In formulas (1-1-3) and (1-2-3), $R^1$ and $R^2$ are independently hydrogen, alkyl having 1 to 10 carbons or alkoxy having 1 to 9 carbons; and the ring $A^3$ and the ring $A^4$ are independently 1,4-cyclohexylene, 1,4-cyclohexenylene, 1,4-phenylene, 1,3-dioxane-2,5-diyl, pyrimidine-2,5-diyl, pyrimidine-3,6-diyl, pyridine-2,5-diyl or pyridine-3,6-diyl.

Item 11. The compound according to item 10, wherein in formulas (1-1-3) and (1-2-3) according to item 10, the ring $A^3$ and the ring $A^4$ are 1,4-cyclohexylene.

Item 12. A compound represented by formula (1-1-4).

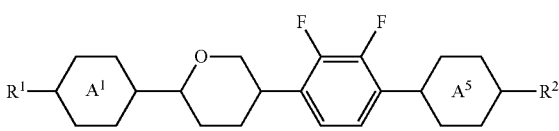

(1-1-4)

In formula (1-1-4), $R^1$ and $R^2$ are independently hydrogen, alkyl having 1 to 10 carbons or alkoxy having 1 to 9 carbons; and the ring $A^1$ and the ring $A^5$ are independently 1,4-cyclohexylene, 1,4-cyclohexenylene, 1,4-phenylene, 1,3-dioxane-2,5-diyl, pyrimidine-2,5-diyl, pyrimidine-3,6-diyl, pyridine-2,5-diyl or pyridine-3,6-diyl.

Item 13. The compound according to item 12, wherein in formula (1-1-4) according to item 12, the ring $A^1$ and the ring $A^5$ are 1,4-cyclohexylene.

Item 14. A compound represented by formula (1-1-5) or (1-2-5).

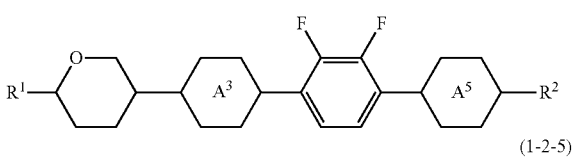

(1-1-5)

(1-2-5)

In formula (1-1-5) or (1-2-5), $R^1$ and $R^2$ are independently hydrogen, alkyl having 1 to 10 carbons or alkoxy having 1 to 9 carbons; and the ring $A^3$ and the ring $A^5$ are independently 1,4-cyclohexylene, 1,4-cyclohexenylene, 1,4-phenylene, 1,3-dioxane-2,5-diyl, pyrimidine-2,5-diyl, pyrimidine-3,6-diyl, pyridine-2,5-diyl or pyridine-3,6-diyl.

Item 15. The compound according to item 14, wherein in formula (1-1-5) or (1-2-5) according to item 14, the ring $A^3$ and the ring $A^5$ are 1,4-cyclohexylene.

Item 16. A compound represented by formula (1-1-6).

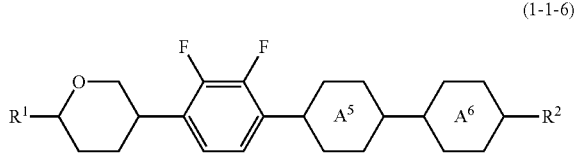
(1-1-6)

In formula (1-1-6), $R^1$ and $R^2$ are independently hydrogen, alkyl having 1 to 10 carbons or alkoxy having 1 to 9 carbons; and the ring $A^5$ and the ring $A^6$ are independently 1,4-cyclohexylene, 1,4-cyclohexenylene, 1,4-phenylene, 1,3-dioxane-2,5-diyl, pyrimidine-2,5-diyl, pyrimidine-3,6-diyl, pyridine-2,5-diyl or pyridine-3,6-diyl.

Item 17. The compound according to item 16, wherein in formula (1-1-6) according to item 16, the ring $A^5$ and the ring $A^6$ are 1,4-cyclohexylene.

Item 18. A compound represented by any one of formulas (1-A) to (1-F).

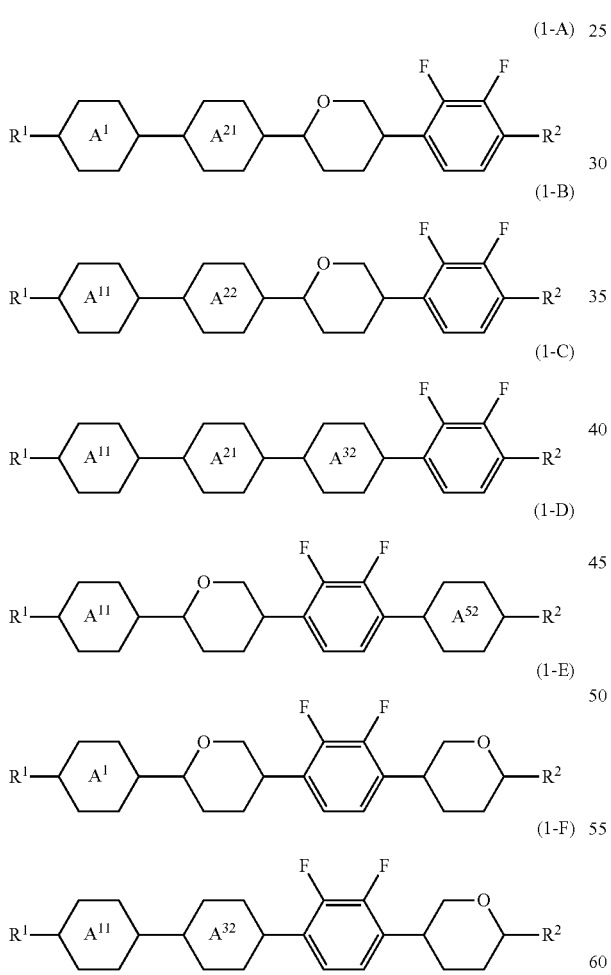

In formulas (1-A) to (1-F), $R^1$ and $R^2$ are independently hydrogen, alkyl having 1 to 10 carbons or alkoxy having 1 to 9 carbons;

the ring $A^1$ is 1,4-cyclohexylene, 1,4-cyclohexenylene, 1,4-phenylene, tetrahydropyran-2,5-diyl, tetrahydropyran-3,6-diyl, 1,3-dioxane-2,5-diyl, pyrimidine-2,5-diyl, pyrimidine-3,6-diyl, pyridine-2,5-diyl or pyridine-3,6-diyl, the ring $A^{11}$ and the ring $A^{21}$ are independently tetrahydropyran-2,5-diyl or tetrahydropyran-3,6-diyl; and the ring $A^{22}$ the ring $A^{32}$ and the ring $A^{52}$ are independently 1,4-cyclohexylene, 1,4-cyclohexenylene, 1,4-phenylene, 1,3-dioxane-2,5-diyl, pyrimidine-2,5-diyl, pyrimidine-3,6-diyl, pyridine-2,5-diyl or pyridine-3,6-diyl.

Item 19. The compound according to item 18, wherein in formulas (1-A) to (1-F) according to item 18, the ring $A^1$, the ring $A^{22}$, the ring $A^{32}$ and the ring $A^{52}$ are 1,4-cyclohexylene.

Item 20. A liquid crystal composition including a first component and a second component, wherein the first component is at least one selected from compounds according to any one of items 1 to 19.

Item 21. The liquid crystal composition according to item 20, including at least one compound selected from the group of compounds represented by formulas (2) to (4) as the second component.

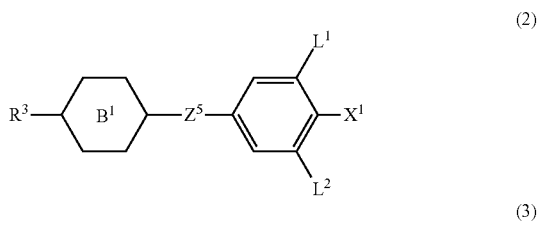
(2)

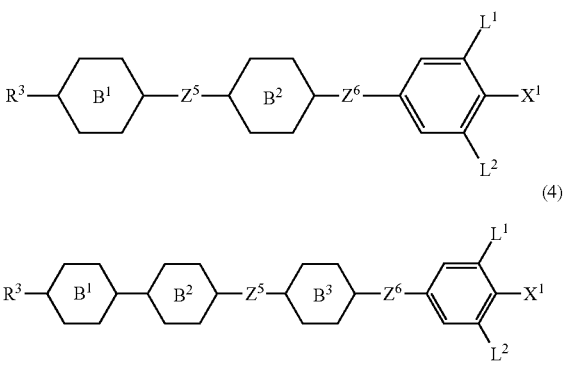
(3)

(4)

In formulas (2) to (4), $R^3$ is independently alkyl having 1 to 10 carbons or alkenyl having 2 to 10 carbons, and in the alkyl and the alkenyl, arbitrary hydrogen may be replaced by fluorine and arbitrary —$CH_2$— may be replaced by —O—;

$X^1$ is independently fluorine, chlorine, —$OCF_3$, —$OCHF_2$, —$CF_3$—$CHF_2$, —$CH_2F$, —$OCF_2CHF_2$ or —$OCF_2CHFCF_3$;

the ring $B^1$, the ring $B^2$ and the ring $B^3$ are independently 1,4-cyclohexylene, 1,3-dioxane-2,5-diyl, pyrimidine-2,5-diyl, tetrahydropyran-2,5-diyl or 1,4-phenylene in which arbitrary hydrogen may be replaced by fluorine;

$Z^5$ and $Z^6$ are independently —$(CH_2)_2$—, —$(CH_2)_4$—, —COO—, —$CF_2O$—, —$OCF_2$—, —CH=CH—, —C≡C—, —$CH_2O$— or a single bond; and $L^1$ and $L^2$ are independently hydrogen or fluorine.

Item 22. The liquid crystal composition according to item 20, including at least one compound selected from the group of compounds represented by formula (5) as the second component.

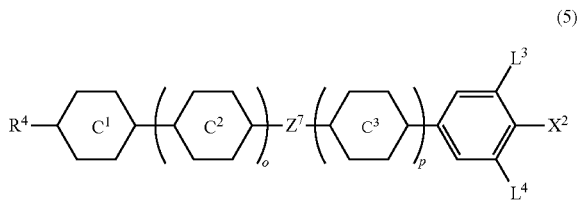
(5)

In formula (5), $R^4$ is alkyl having 1 to 10 carbons or alkenyl having 2 to 10 carbons, and in the alkyl and the alkenyl, arbitrary hydrogen may be replaced by fluorine and arbitrary —$CH_2$— may be replaced by —O—;

$X^2$ is —O≡N or —C≡C—C≡N;

the ring $C^1$, the ring $C^2$ and the ring $C^3$ are independently 1,4-cyclohexylene, 1,4-phenylene in which arbitrary hydrogen may be replaced by fluorine, 1,3-dioxane-2,5-diyl, tetrahydropyran-2,5-diyl or pyrimidine-2,5-diyl;

$Z^7$ is —$(CH_2)_2$—, —COO—, —$CF_2O$—, —$OCF_2$—, —C≡C—, —$CH_2O$— or a single bond;

$L^3$ and $L^4$ are independently hydrogen or fluorine; and o is 0, 1 or 2, and p is 0 or 1.

Item 23. The liquid crystal composition according to item 20, including at least one compound selected from the group of compounds represented by formulas (6) to (11) as the second component.

In formulas (6) to (11), $R^5$ and $R^6$ are independently alkyl having 1 to 10 carbons or alkenyl having 2 to 10 carbons, and in the alkyl or the alkenyl arbitrary —$CH_2$— may be replaced by —O—, and in the alkenyl arbitrary hydrogen may be replaced by fluorine;

the ring $D^1$, the ring $D^2$, the ring $D^3$ and the ring $D^4$ are independently 1,4-cyclohexylene, 1,4-cyclohexenylene, 1,4-phenylene in which arbitrary hydrogen may be replaced by fluorine or tetrahydropyran-2,5-diyl;

$Z^8$, $Z^9$, $Z^{10}$ and $Z^{11}$ are independently —$(CH_2)_2$—, —COO—, —$CH_2O$—, —$OCF_2$—, —$OCF_2(CH_2)_2$— or a single bond;

$L^5$ and $L^6$ are independently fluorine or chlorine; and q, r, s, t, u and v are independently 0 or 1, and the sum of r, s, t and u is 1 or 2.

Item 24. The liquid crystal composition according to item 20, including at least one compound selected from the group of compounds represented by formulas (12) to (14) as the second component.

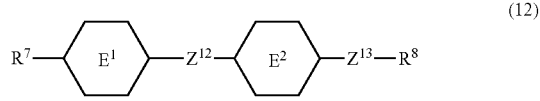
(12)

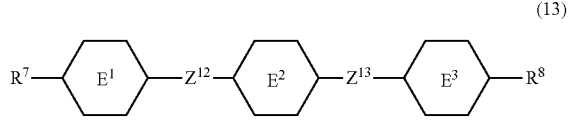
(13)

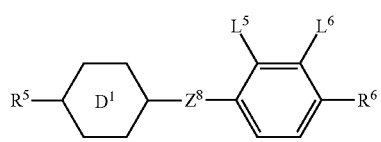
(6)

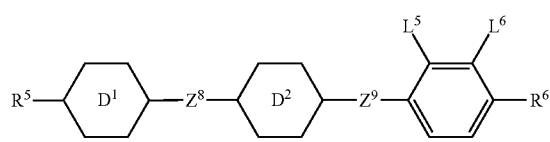
(7)

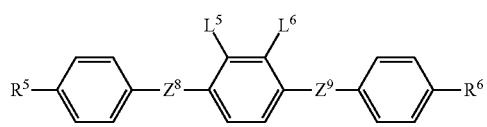
(8)

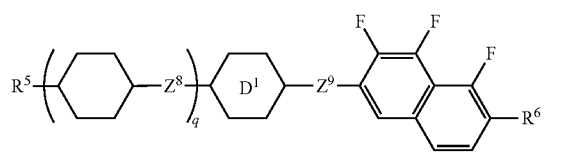
(9)

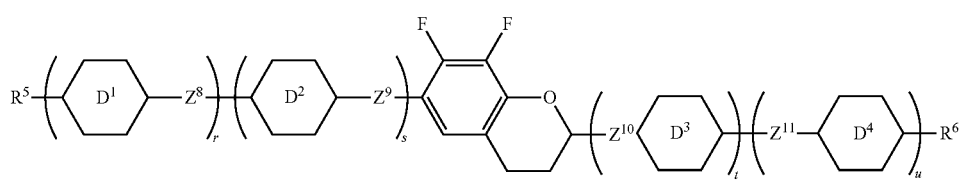
(10)

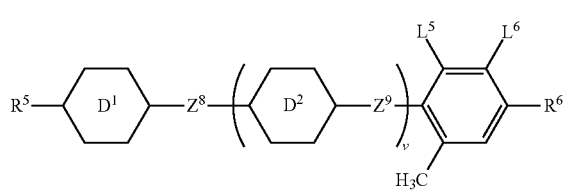
(11)

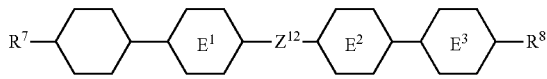

(14)

In formulas (12) to (14), $R^7$ and $R^8$ are independently alkyl having 1 to 10 carbons or alkenyl having 2 to 10 carbons, and in the alkyl or the alkenyl arbitrary —$CH_2$— may be replaced by —O—, and in the alkenyl arbitrary hydrogen may be replaced by fluorine;

the ring $E^1$, the ring $E^2$ and the ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{12}$ and $Z^{13}$ are independently —C≡C—, —COO—, —($CH_2)_2$—, —CH=CH— or a single bond.

Item 25. The liquid crystal composition according to item 21, further including at least one compound selected from the group of compounds represented by formula (5).

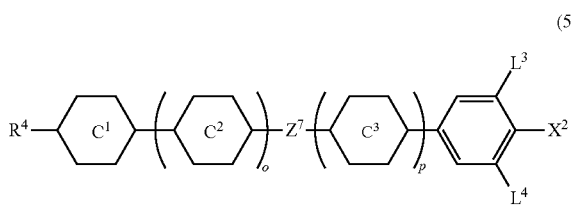

(5)

In formula (5)

$R^4$ is alkyl having 1 to 10 carbons or alkenyl having 2 to 10 carbons, and in the alkyl and the alkenyl, arbitrary hydrogen may be replaced by fluorine and arbitrary —$CH_2$— may be replaced by —O—;

$X^2$ is —C≡N or —C≡C—C≡N;

the ring $C^1$, the ring $C^2$ and the ring $C^3$ are independently 1,4-cyclohexylene, 1,4-phenylene in which arbitrary hydrogen may be replaced by fluorine, 1,3-dioxane-2,5-diyl, tetrahydropyran-2,5-diyl or pyrimidine-2,5-diyl;

$Z^7$ is —($CH_2)_2$—, —COO—, —$CF_2O$—, —$OCF_2$—, —C≡C—, —$CH_2O$— or a single bond;

$L^3$ and $L^4$ are independently hydrogen or fluorine; and o is 0, 1 or 2, and p is 0 or 1.

Item 26. The liquid crystal composition according to item 21, further including at least one compound selected from the group of compounds represented by formulas (12) to (14).

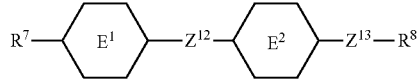

(12)

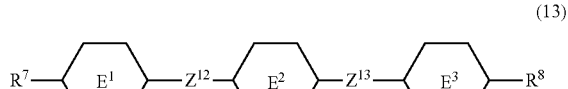

(13)

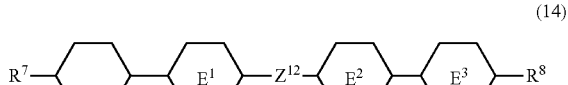

(14)

In formulas (12) to (14), $R^7$ and $R^8$ are independently alkyl having 1 to 10 carbons or alkenyl having 2 to 10 carbons, and in the alkyl or the alkenyl arbitrary —$CH_2$— may be replaced by —O—, and in the alkenyl arbitrary hydrogen may be replaced by fluorine;

the ring $E^1$, the ring $E^2$ and the ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{12}$ and $Z^{13}$ are independently —C≡C—, —COO—, —($CH_2)_2$—, —CH=CH— or a single bond.

Item 27. The liquid crystal composition according to item 22, further including at least one compound selected from the group of compounds represented by formulas (12) to (14).

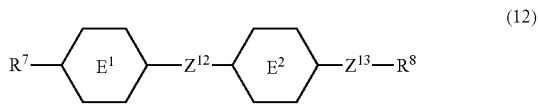

(12)

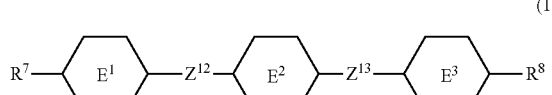

(13)

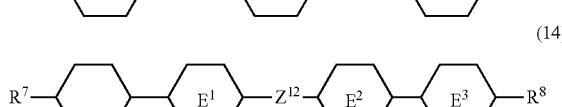

(14)

In formulas (12) to (14), $R^7$ and $R^8$ are independently alkyl having 1 to 10 carbons or alkenyl having 2 to 10 carbons, and in the alkyl or the alkenyl arbitrary —$CH_2$— may be replaced by —O—, and in the alkenyl arbitrary hydrogen may be replaced by fluorine;

the ring $E^1$, the ring $E^2$ and the ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{12}$ and $Z^{13}$ are independently —C≡C—, —COO—, —($CH_2)_2$—, —CH=CH— or a single bond.

Item 28. The liquid crystal composition according to item 23, further including at least one compound selected from the group of compounds represented by formulas (12) to (14).

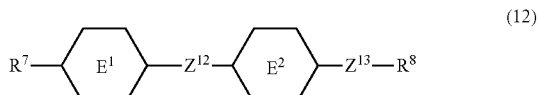

(12)

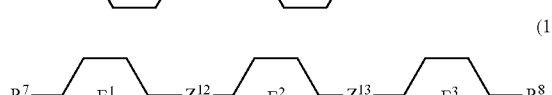

(13)

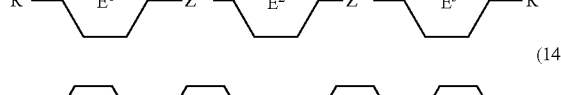

(14)

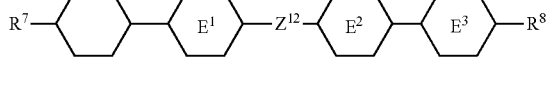

In formulas (12) to (14),

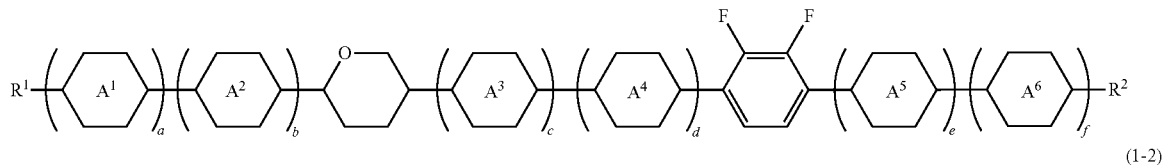

(1-1)

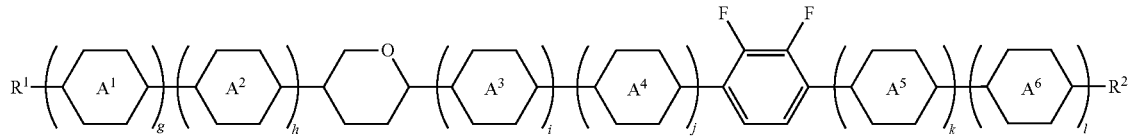

(1-2)

$R^7$ and $R^8$ are independently alkyl having 1 to 10 carbons or alkenyl having 2 to 10 carbons, and in the alkyl or the alkenyl arbitrary —$CH_2$— may be replaced by —O—, and in the alkenyl arbitrary hydrogen may be replaced by fluorine;

the ring $E^1$, the ring $E^2$ and the ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{12}$ and $Z^{13}$ are independently —C≡C—, —COO—, —$(CH_2)_2$—CH═CH— or a single bond.

Item 29. The liquid crystal composition according to item 20, further including at least one optically active compound and/or at least one polymerizable compound.

Item 30. The liquid crystal composition according to item 20, further including at least one antioxidant and/or at least one ultraviolet light absorber.

Item 31. A liquid crystal display device containing the liquid crystal composition according to item 20.

Effect of the Invention

The invention provides a liquid crystal compound not only having a large negative dielectric anisotropy (Δε), a high clearing point and a low viscosity, but also having at least one of characteristics such as stability to heat, light or the like, a suitable refractive index anisotropy (Δn) and an excellent compatibility with other liquid crystal compounds.

The invention also provides a liquid crystal composition having at least one of characteristics such as a low viscosity, a suitable refractive index anisotropy (Δn), a suitable negative dielectric anisotropy (Δε), a low threshold voltage, a high maximum temperature of a nematic phase and a low minimum temperature of a nematic phase.

The invention also provides a liquid crystal display device having at least one of characteristics such as a short response time, low power consumption, a low driving voltage, a large contrast and a wide temperature range in which the device can be used. The device can suitably be used for a liquid crystal display device having a display mode such as a PC mode, a TN mode, a STN mode, an ECB mode, an OCB mode, an IPS mode, a VA mode or a PSA mode. The device can suitably be used especially for a liquid crystal display device having the IPS mode, the VA mode or the PSA mode.

Embodiment to Carry out the Invention

Hereinafter, the invention will be explained more specifically. The liquid crystal compound of the invention is represented by the following formula (1-1) or (1-2).

In formulas (1-1) and (1-2), $R^1$ is hydrogen, alkyl having 1 to 10 carbons or alkoxy having 1 to 9 carbons.

In the alkyl chain in these groups, a straight chain is desirable. When the alkyl chain is straight, the temperature range of a liquid crystal phase is wide and the viscosity is low.

The alkyl is —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$ or —$C_{10}H_{21}$; and the alkoxy is —$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$ or —$OC_9H_{19}$.

Desirable $R^1$ is —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$ or —$C_{10}H_{21}$.

More desirable $R^1$ is —$CH_3$, —$C_2H_5$, —$C_3H_7$, —$C_4H_9$ or —$C_5H_{11}$.

$R^2$ is hydrogen, alkyl having 1 to 10 carbons or alkoxy having 1 to 9 carbons.

The alkyl is —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$ or —$C_{10}H_{21}$; and the alkoxy is —$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$ or —$OC_9H_{19}$.

Desirable $R^2$ is —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$OCH_3$, —$OC_2H_5$, —$OC_3H_7$, —$OC_4H_9$, —$OC_5H_{11}$ or —$OC_6H_{13}$.

More desirable $R^2$ is —$CH_3$, —$C_2H_5$, —$C_3H_7$, —$C_4H_9$, —$C_5H_{11}$, —$OCH_3$, —$OC_2H_5$, —$OC_3H_7$ or —$OC_4H_9$.

In formulas (1-1) and (1-2), the ring $A^1$, the ring $A^2$, the ring $A^3$, the ring $A^4$, the ring $A^5$ and the ring $A^6$ are 1,4-cyclohexylene or 1,4-phenylene, and in the 1,4-cyclohexylene arbitrary —$CH_2$— may be replaced by —O— and arbitrary —$(CH_2)_2$— may be replaced by —CH═CH—, and in the 1,4-phenylene arbitrary —CH═ may be replaced by —N═.

The refractive index anisotropy (Δn) is small and the viscosity is low when these rings are 1,4-cyclohexylene. When the liquid crystal compound is added to a liquid crystal composition, the maximum temperature of a nematic phase is increased.

The refractive index anisotropy (Δn) is relatively large and the orientational order parameter is large when these rings are 1,4-phenylene in which hydrogen may be replaced by fluorine.

Desirable ring $A^1$, ring $A^2$, ring $A^3$, ring $A^4$, ring $A^5$ and ring $A^6$ are 1,4-cyclohexylene, 1,4-cyclohexenylene, 1,4-phenylene, tetrahydropyran-2,5-diyl or tetrahydropyran-3,6-diyl.

It is desirable that the double bond of a 1,4-cyclohexenylene ring should not be bonded directly to a phenylene ring in view of the stability to heat, light or the like.

a, b, c, d, e and f are independently 0 or 1, and the sum of a, b, c, d, e and f is 2.

g, h, i, j, k and l are independently 0 or 1, and the sum of g, h, i, j, k and l is 2.

It is desirable that at least one of i and j in formula (1-2) should be 1 for increasing dielectric anisotropy (Δε) negatively.

Desirable examples of a liquid crystal compound represented by formula (1-1) include formulas (1-1-1) to (1-1-6). Desirable examples of a liquid crystal compound represented by formula (1-2) include formulas (1-2-2), (1-2-3) and (1-2-5).

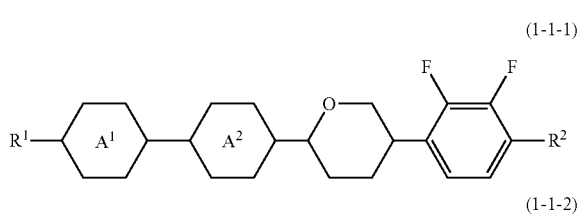
(1-1-1)

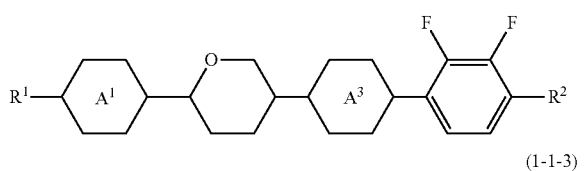
(1-1-2)

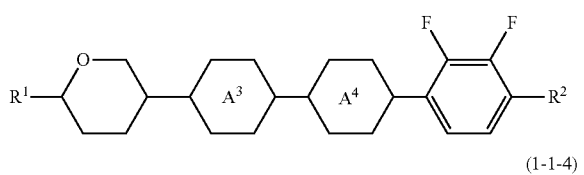
(1-1-3)

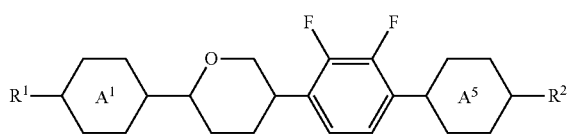
(1-1-4)

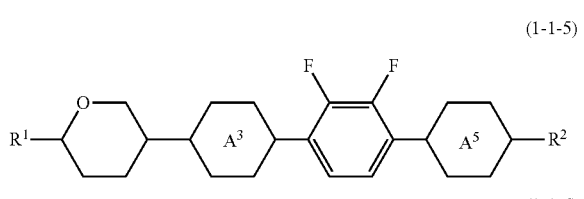
(1-1-5)

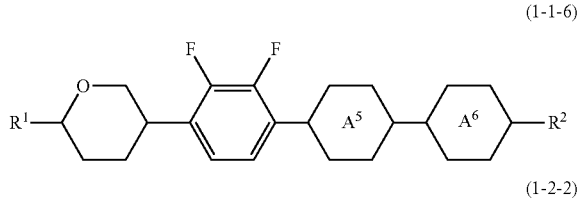
(1-1-6)

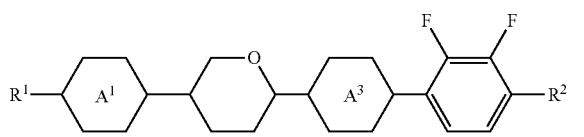
(1-2-2)

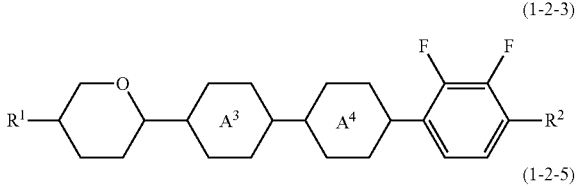
(1-2-3)

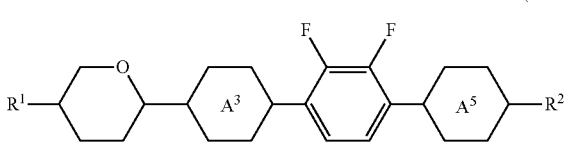
(1-2-5)

In the formulas, $R^1$ and $R^2$ are independently hydrogen, alkyl having 1 to 10 carbons or alkoxy having 1 to 9 carbons; and the ring $A^1$ the ring $A^2$, the ring $A^3$, the ring $A^4$, the ring $A^5$ and the ring $A^6$ are independently 1,4-cyclohexylene, 1,4-cyclohexenylene, 1,4-phenylene, 1,3-dioxane-2,5-diyl, pyrimidine-2,5-diyl, pyrimidine-3,6-diyl, pyridine-2,5-diyl or pyridine-3,6-diyl.

Incidentally, in this specification tetrahydropyran-2,5-diyl means the structure represented by formula (I), and tetrahydropyran-3,6-diyl means the structure represented by formula (II).

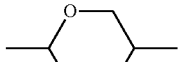
(I)

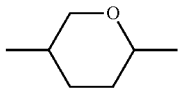
(II)

The distinction of the compound structures in 1,3-dioxane-2,5-diyl is difficult according to the position of oxygen in the ring, which is different from the case of tetrahydropyran-2,5-diyl and tetrahydropyran-3,6-diyl, for instance. Thus, the following two compound structures are allowable in the notation of 1,3-dioxane-2,5-diyl.

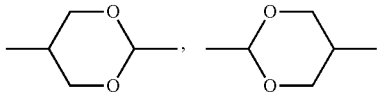

A compound represented by formula (1-1) or (1-2) of the invention can be prepared by the introduction of a predetermined group into $R^1$, $R^2$, the ring $A^1$, the ring $A^2$, the ring $A^3$, the ring $A^4$, the ring $A^5$ and the ring $A^6$ in the formula. The introduction of these kinds of groups can be carried out by known and general synthetic organic methods. Representative examples of the synthesis include the methods described in "Vol. 14: Synthesis and Reaction of Organic Compounds" (1978) in Shin-Jikken Kagaku Kouza (New Experimental Chemistry Course, in English; Maruzen Co., Ltd.), or "Vol. 19 to Vol. 26: Organic Synthesis I to VIII" (1991) in Daiyonhann-Jikken Kagaku Kouza (Fourth edition-Experimental Chemistry Course, in English; Maruzen Co., Ltd.).

Next, one example of the method for the preparation of the compound (1-1) or (1-2) will be shown in the scheme.

The preparation of the intermediate (30) having an oxetane moiety is explained first, and then one example of the method of the preparation of the tetrahydropyran-3,6-diyl compound (36) is described, in which the synthetic intermediate (30) is the starting material.

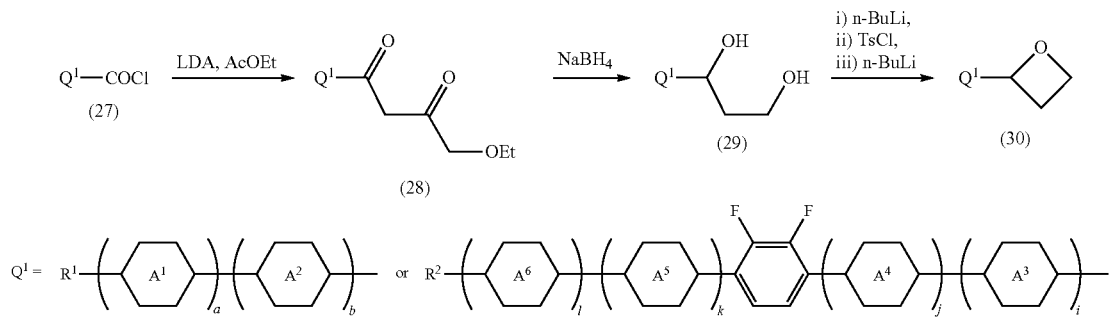

In the compounds (27) to (30), $Q^1$ is a structural unit in formula (1-1) or (1-2). The structural unit is shown in the scheme. The definitions of the symbols $R^1$, $R^2$, $A^1$, $A^2$, $A^3$, $A^4$, $A^5$, $A^6$, a, b, i, j, k and l in these compounds are the same as those described in item 1.

That is to say, the compound (28) is prepared by the reaction of the compound (27) with LDA (lithium diisopropylamide), followed by the reaction with ethyl acetate. These reactions is preferably carried out in a tetrahydrofuran solvent at temperatures of −65° C. or less, and then the reaction mixture is slowly warmed to room temperature. The compound (29) is prepared by the reaction of the compound (28) with sodium borohydride. The reaction is preferably carried out in an ethanol solvent in the temperature range of room temperature to 50° C. The compound (29) is allowed to react with n-butyllithium in a tetrahydrofuran solvent in the temperature range of −5° C. to 5° C., and then with p-toluenesulfonyl chloride. n-Butyllithium is then added, and the reaction mixture is slowly heated to its boiling point to give the compound (30). It is desirable that the interval of the reactions should be sufficient, and one equivalent of each reagent should be used.

The compound (27), which is a starting material, can be easily prepared according to the methods in synthetic organic chemistry.

Next, One example of the method for synthesizing the compound (36) is shown.

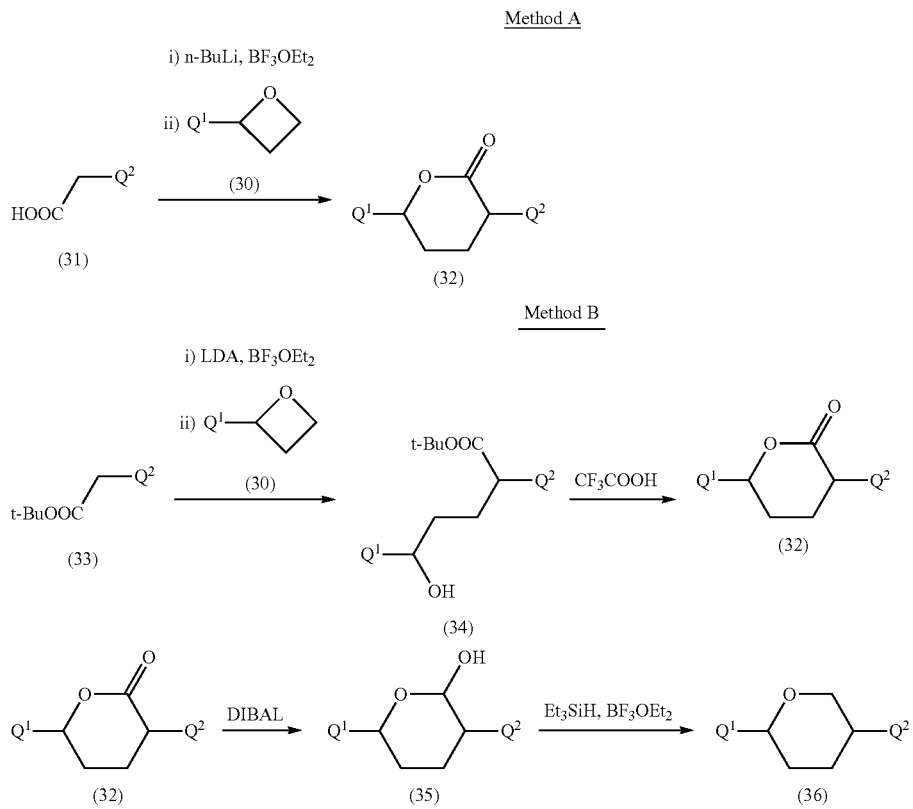

case 1

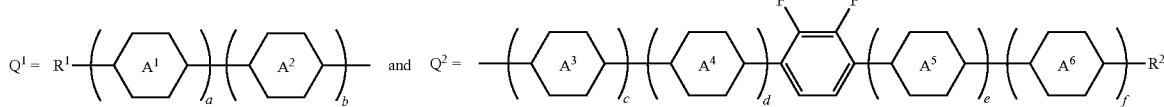

case 2

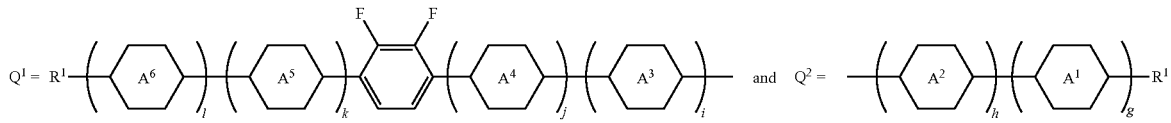

In the compounds (30) to (34), $Q^1$ or $Q^2$ is the structural unit of formula (1-1) or (1-2). The structural unit is shown in the scheme. The definitions of the symbols $R^1, R^2, A^1, A^2, A^3, A^4, A^5, A^6$, a, b, c, d, e, f, g, h, i, j, k and l in these compounds are the same as those described in item 1. In the scheme, the case 1 corresponds to the compound (1-1) and the case 2 corresponds to the compound (1-2).

The method for the preparation of the compound (32) is different depending on the structure of $Q^2$. Two examples of the synthetic methods will be shown. The method A is used for the preparation of a compound where c and d are 0 in the case 1. The method B is used for the preparation of a compound where at least one of c and d is 1, and of a compound of case 2.

Method A: The compound (32) is prepared by the reaction of the compound (31) with n-butyllithium, and then with the compound (30) in the presence of a boron trifluoride-ethyl ether complex. The reaction is preferably carried out in a tetrahydrofuran solvent at −65° C. or lower.

Method B: The compound (34) is prepared by the reaction of the compound (33) with LDA (lithium diisopropylamide), and then with the compound (30) in the presence of a boron trifluoride-ethyl ether complex. The reaction is carried out preferably in a tetrahydrofuran solvent at −65° C. or lower. The compound (34) is then allowed to react with trifluoroacetic acid in a dichloromethane solvent at room temperature to give the compound (32).

The compound (35) is prepared by the reaction of the compound (32) with DIBAL (diisobutylaluminium hydride). The reaction is carried out preferably in a toluene solvent at −50° C. or lower. The compound (36) is prepared by the reaction of the compound (35) in the presence of triethylsilane and a boron trifluoride-ethyl ether complex in a dichloromethane solvent at −50° C. or lower.

The compound (31) and the compound (33) are easily prepared according to the methods in synthetic organic chemistry.

The liquid crystal composition of the invention should include a compound represented by formula (1-1) or (1-2) of the invention described above as a component A. The composition may include the component A only. The composition may include the component A and another component that is not specifically described in this specification. The liquid crystal composition of the invention which has a variety of characteristics can be provided by the addition of a component selected from the components B, C, D and E, these of which will be shown below, to the component A.

Desirable components that will be added to the component A is the component B that is at least one compound selected from the group of compounds represented by formulas (2), (3) and (4) described above, and/or the component C that is at least one compound selected from the group of compounds represented by formula (5) described above, and/or the component D that is at least one compound selected from the group of compounds represented by formulas (6), (7), (8), (9), (10) and (11) described above. Further, the threshold voltage, the temperature range of a liquid crystal phase, the refractive index anisotropy (Δn), the dielectric anisotropy (Δε), the viscosity and so forth can be adjusted by the addition of the component E that is at least one compound selected from the group of compounds represented by formulas (12), (13) and (14).

In each component used in the liquid crystal composition of the invention, there are no major differences in physical properties even if the compound is an analogue composed of any isotope of each element.

In component B described above, desirable examples of the compound (2) include the compounds (2-1) to (2-16), desirable examples of the compound (3) include the compounds (3-1) to (3-112), and desirable examples of the compound (4) include the compounds (4-1) to (4-54).

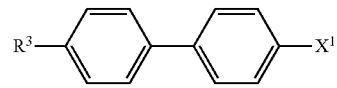

(2-1)

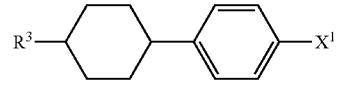

(2-2)

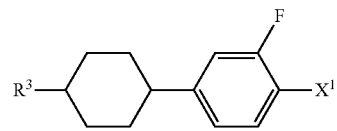

(2-3)

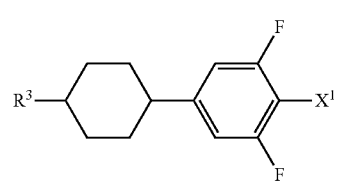

(2-4)

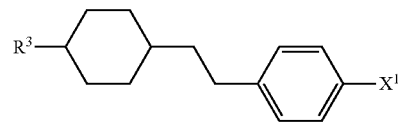

(2-5)

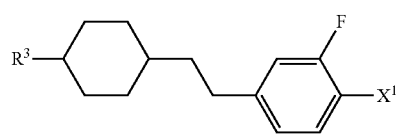
(2-6)
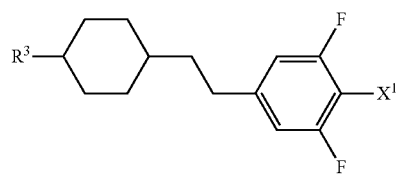
(2-7)
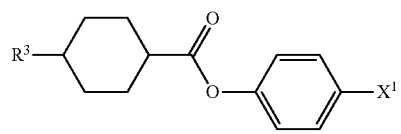
(2-8)
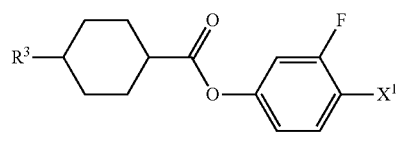
(2-9)
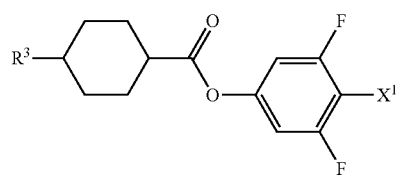
(2-10)
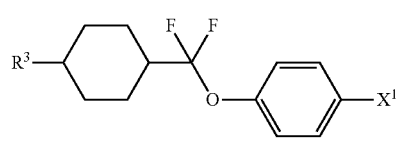
(2-11)
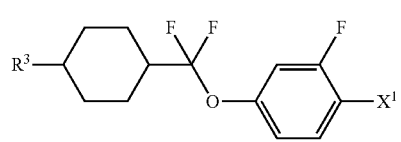
(2-12)
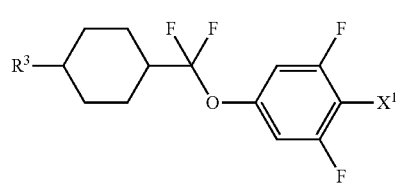
(2-13)
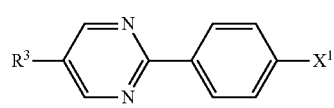
(2-14)
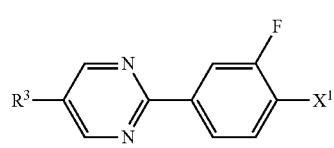
(2-15)
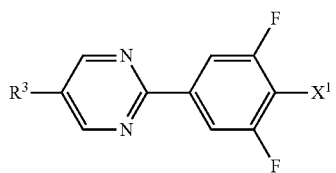
(2-16)
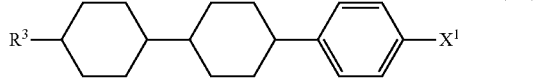
(3-1)
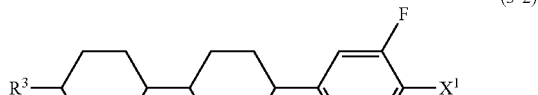
(3-2)
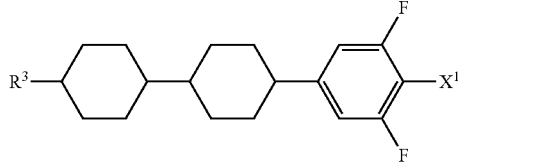
(3-3)
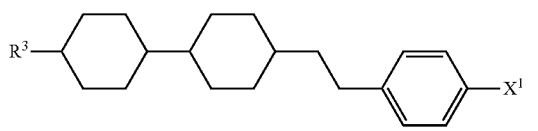
(3-4)
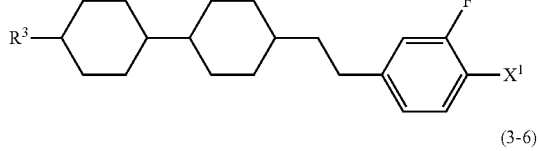
(3-5)
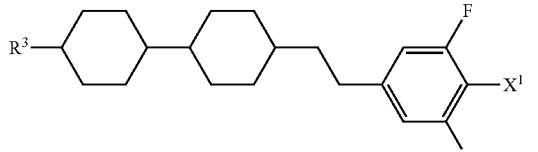
(3-6)
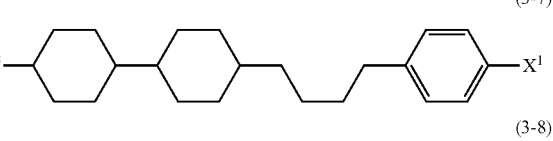
(3-7)
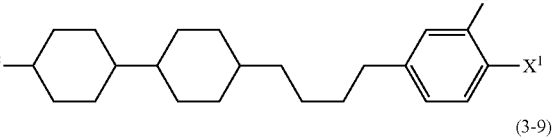
(3-8)
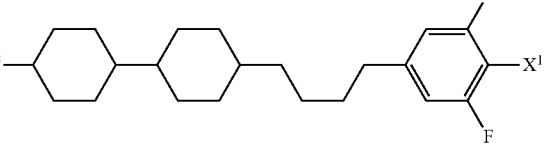
(3-9)

(3-10)
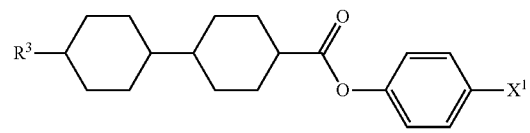
(3-11)
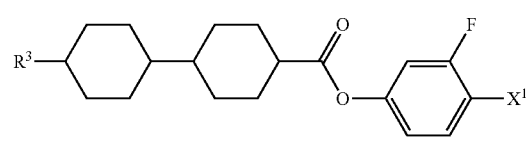
(3-12)
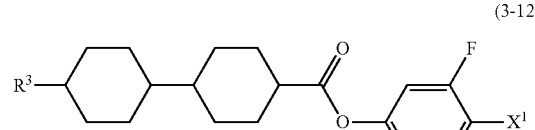
(3-13)
(3-14)
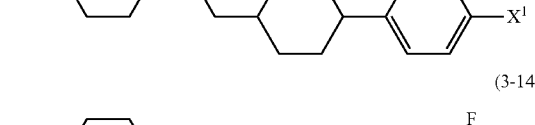
(3-15)
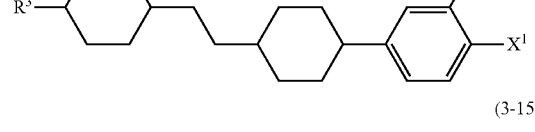
(3-16)
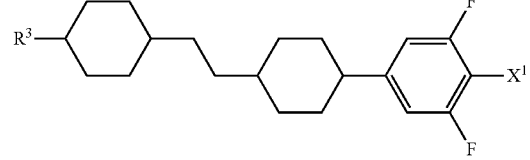
(3-17)
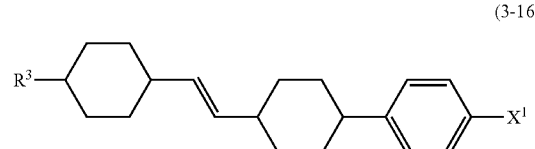
(3-18)
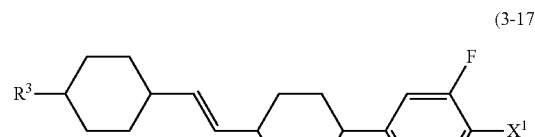
(3-19)
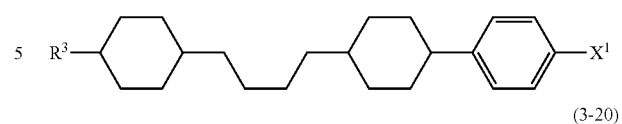
(3-20)
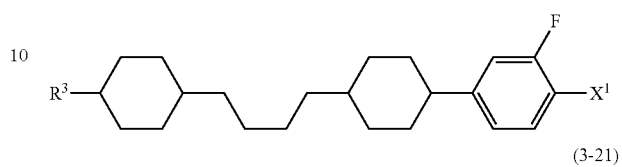
(3-21)
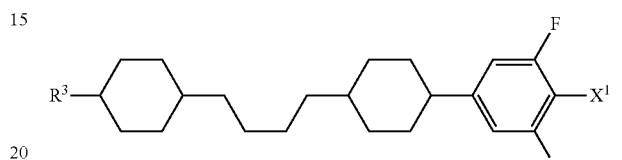
(3-22)
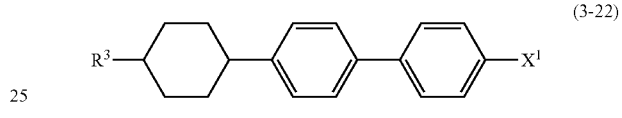
(3-23)
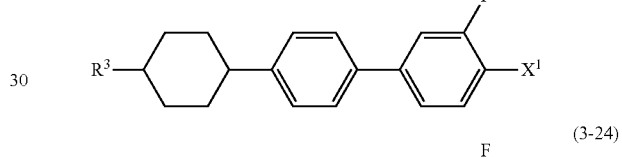
(3-24)
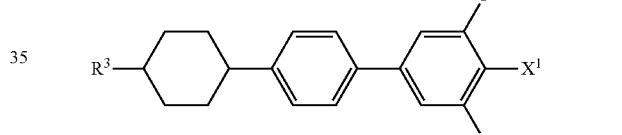
(3-25)
(3-26)
(3-27)
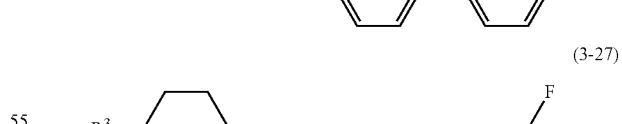
(3-28)
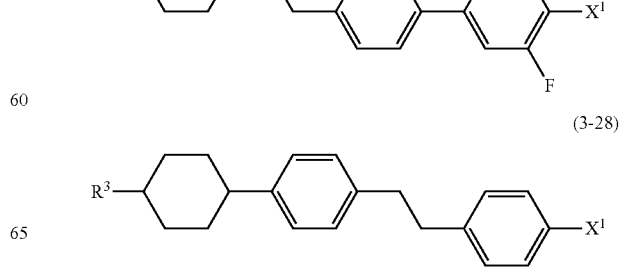

(3-29)
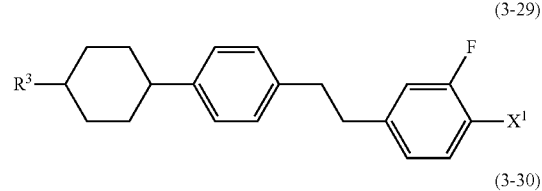
(3-30)
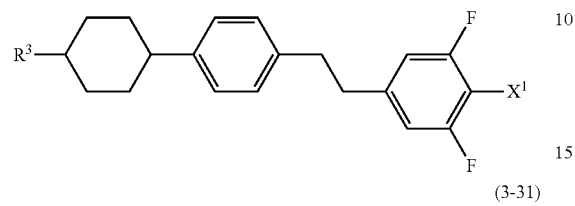
(3-31)
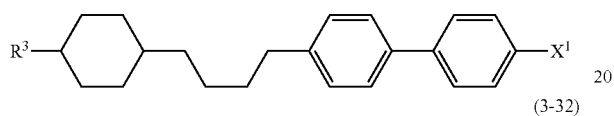
(3-32)
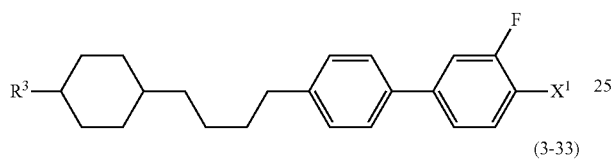
(3-33)
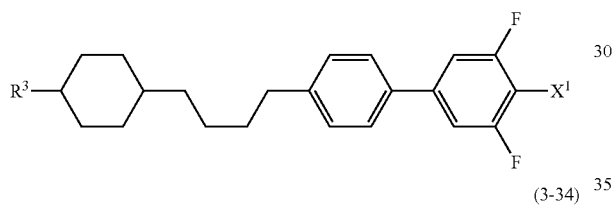
(3-34)
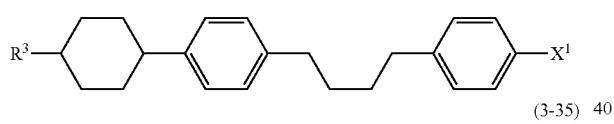
(3-35)
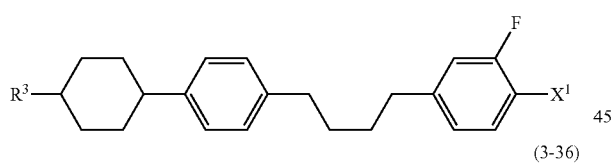
(3-36)
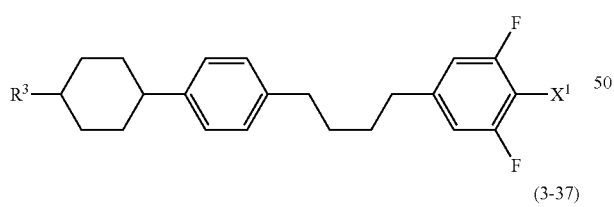
(3-37)
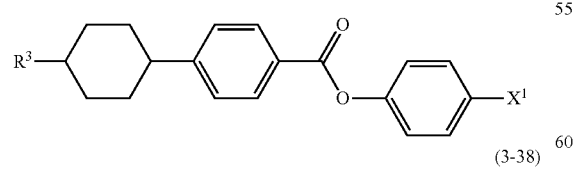
(3-38)
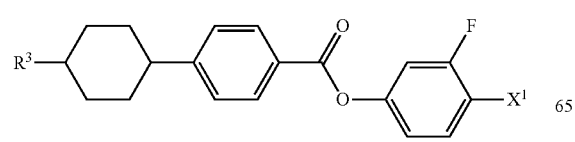
(3-39)
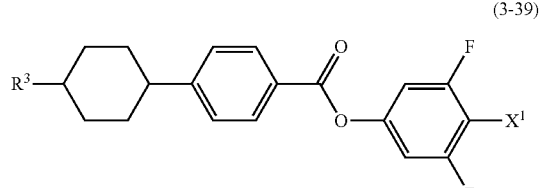
(3-40)
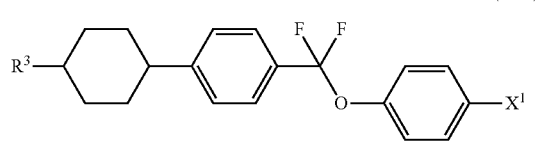
(3-41)
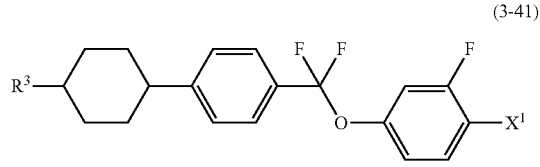
(3-42)
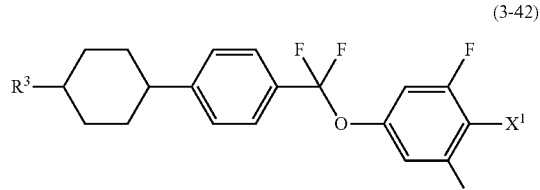
(3-43)
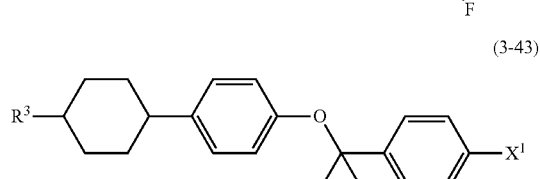
(3-44)
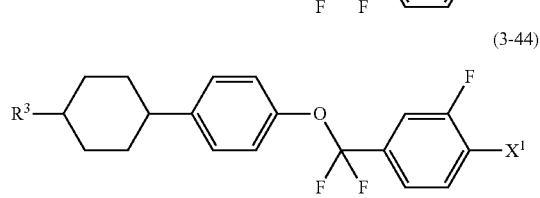
(3-45)
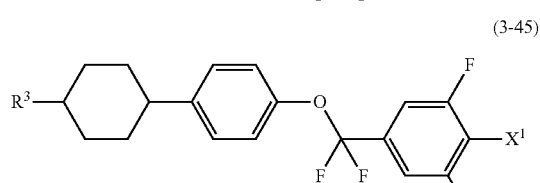
(3-46)
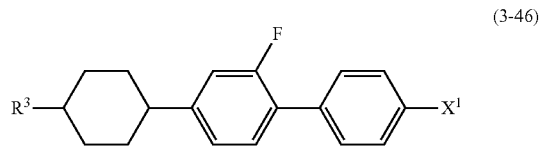
(3-47)
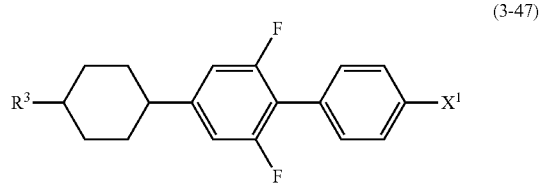

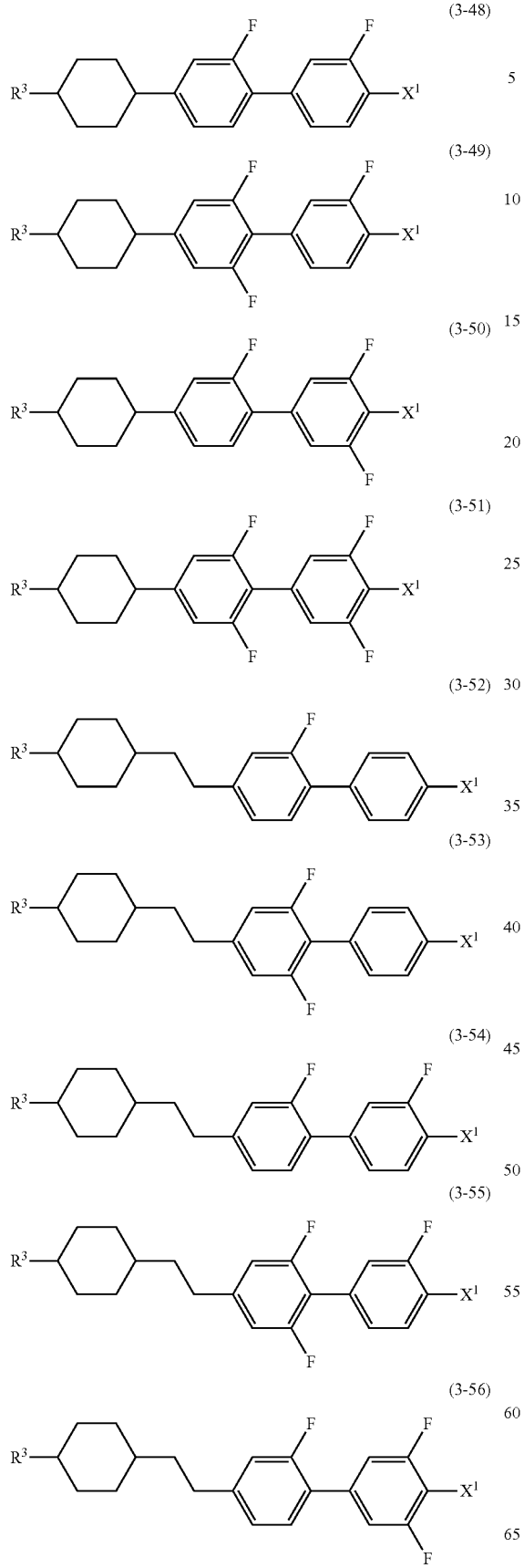
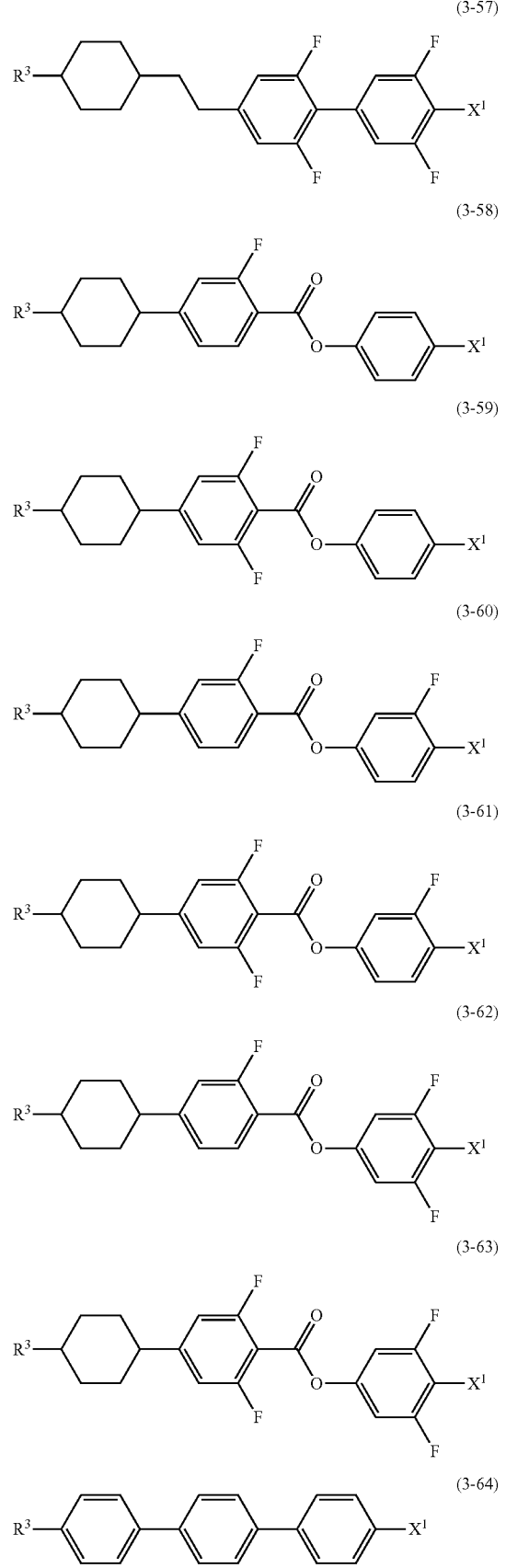

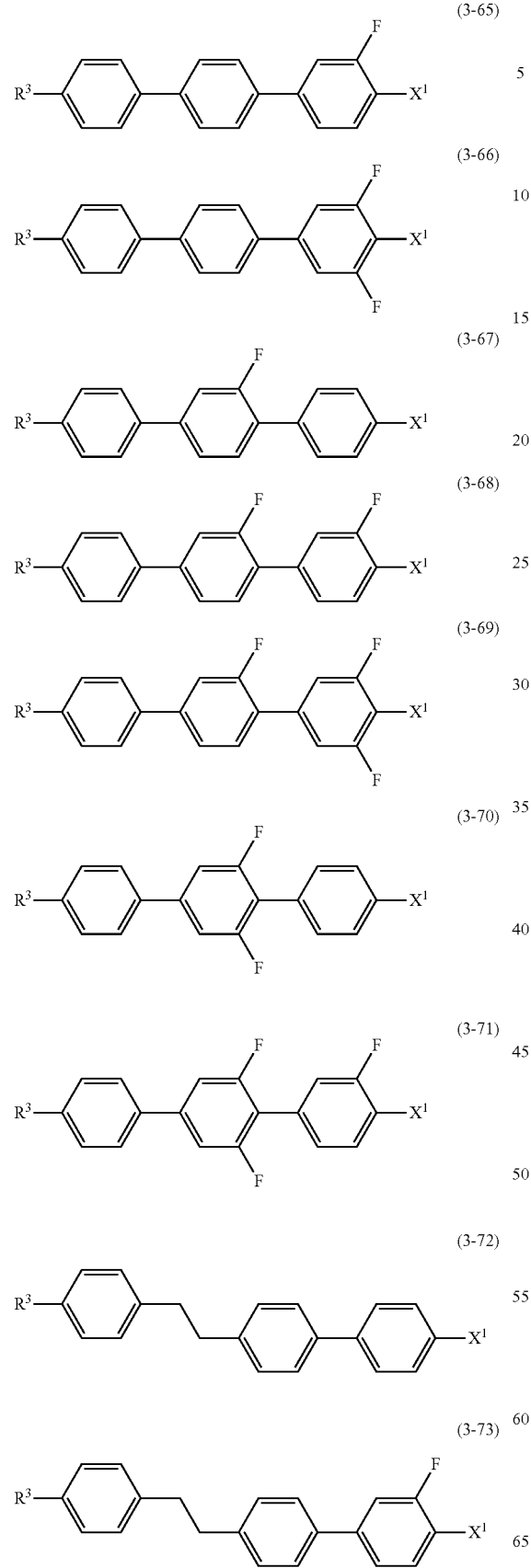
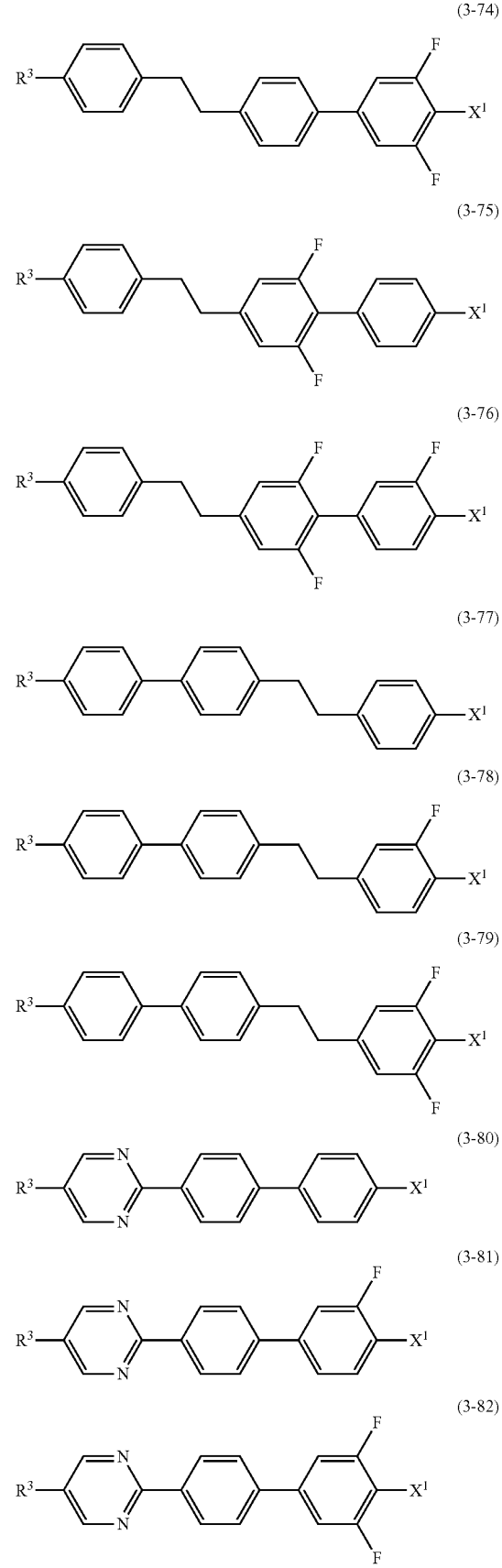

(3-83) 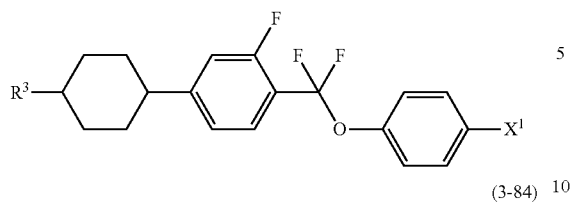
(3-84) 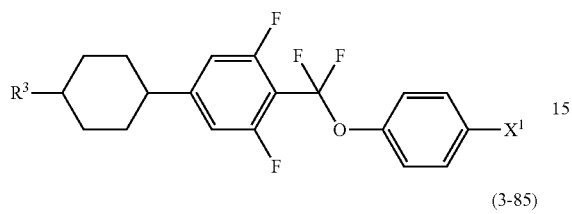
(3-85) 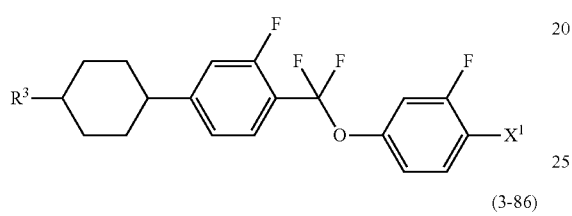
(3-86) 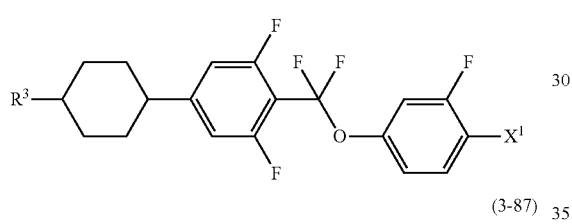
(3-87) 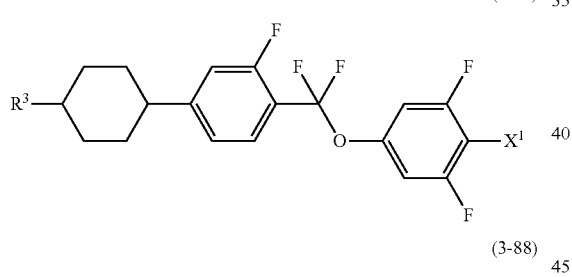
(3-88) 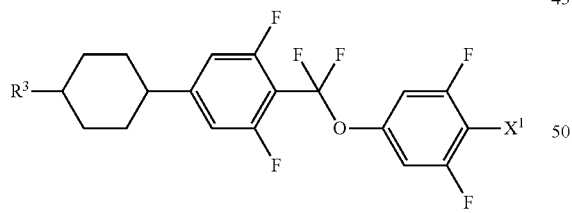
(3-89) 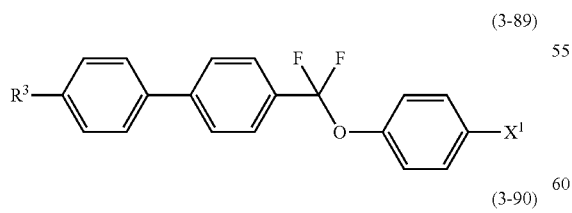
(3-90) 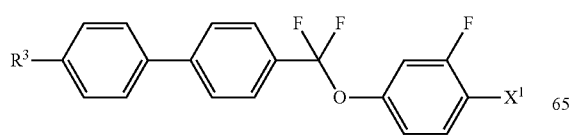
(3-91) 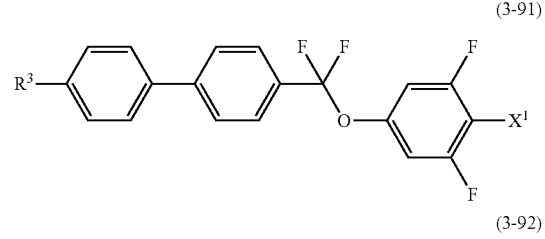
(3-92) 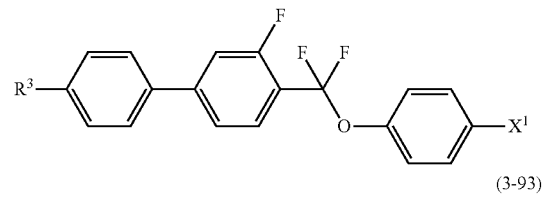
(3-93) 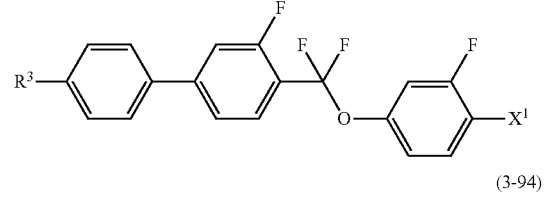
(3-94) 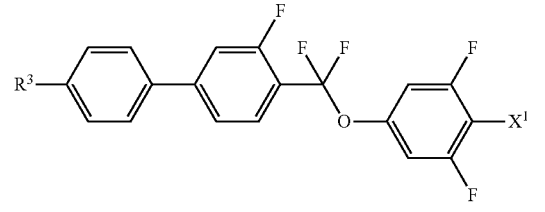
(3-95) 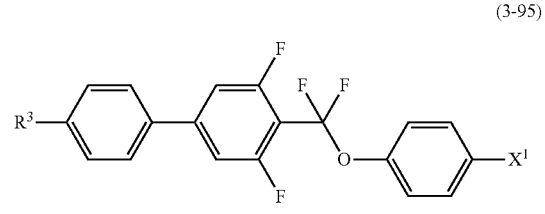
(3-96) 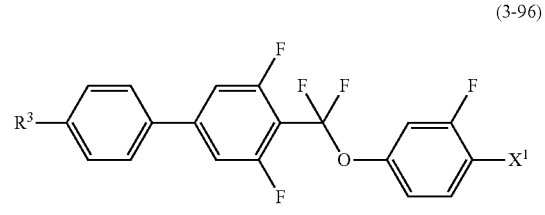
(3-97) 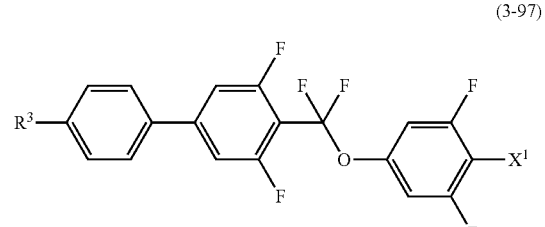
(3-98) 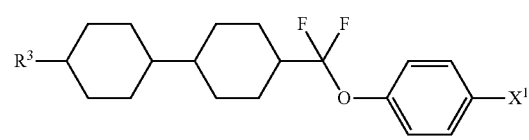

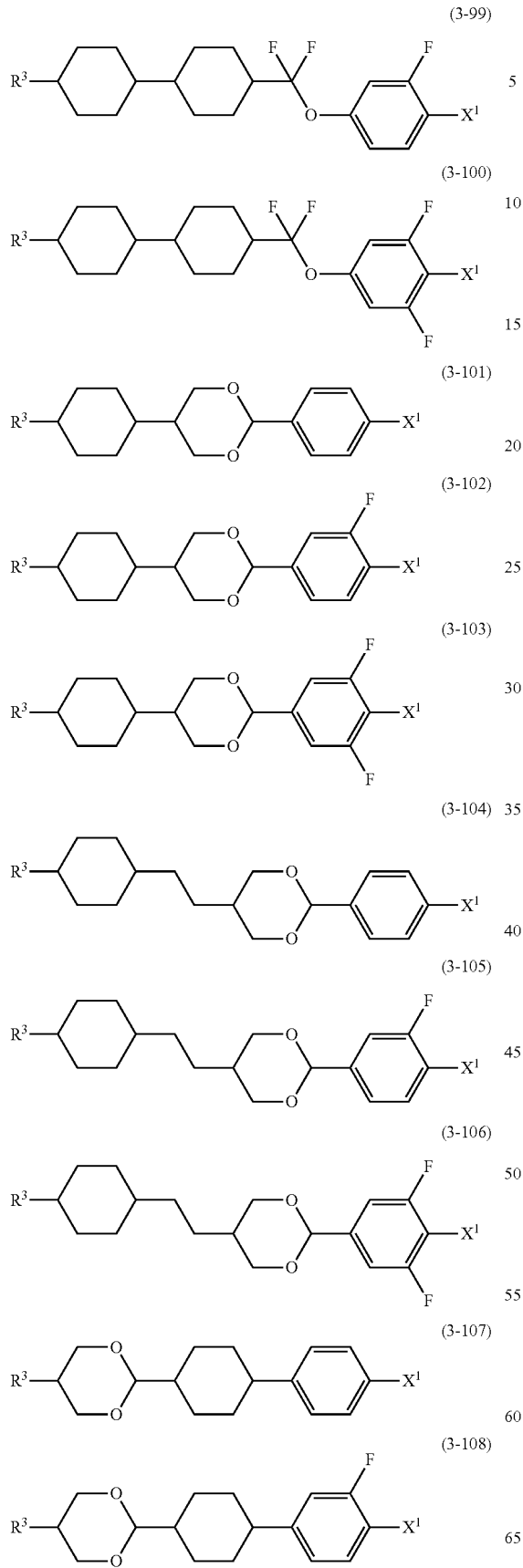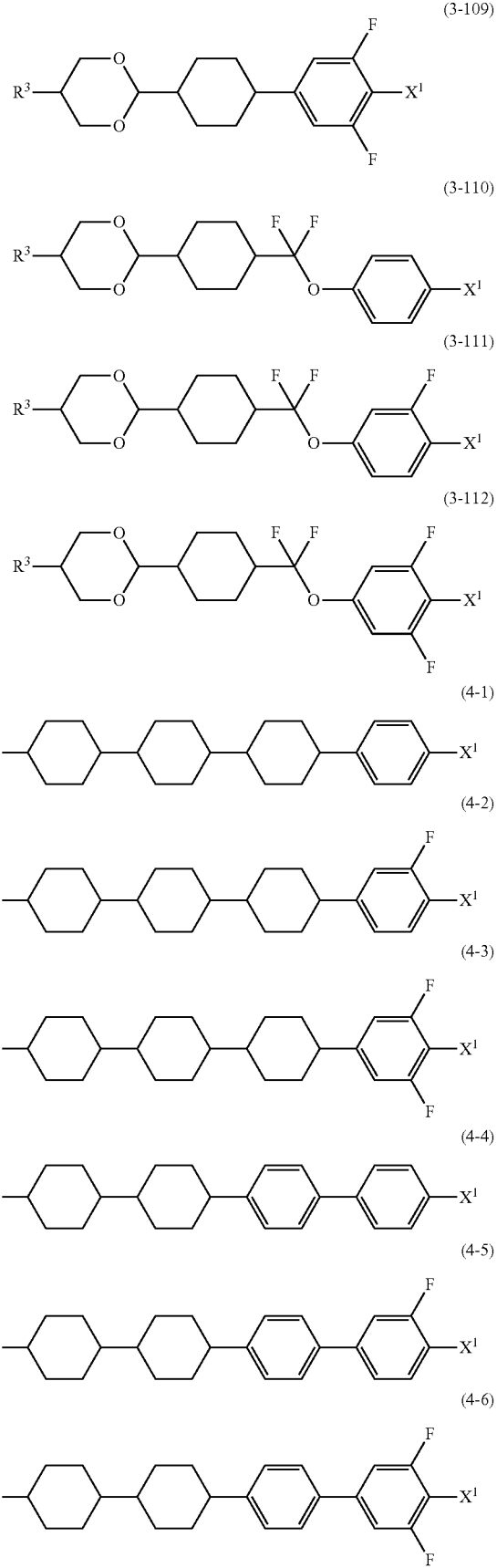

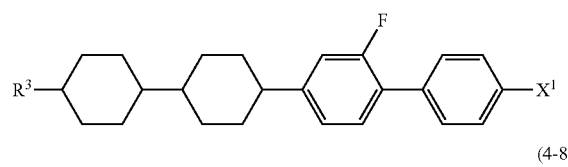 (4-7)
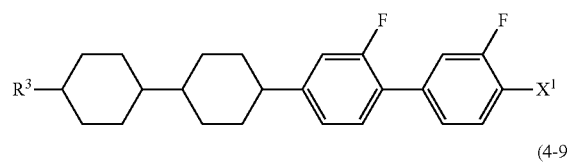 (4-8)
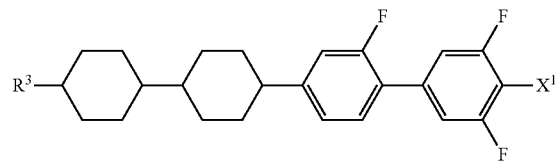 (4-9)
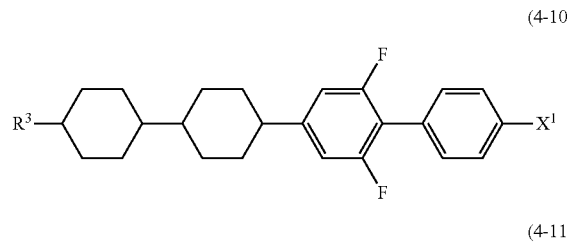 (4-10)
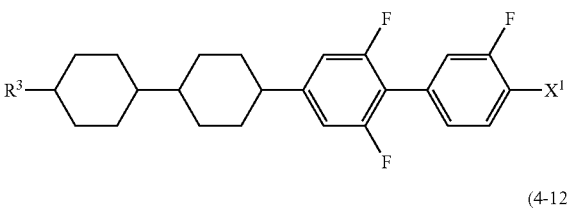 (4-11)
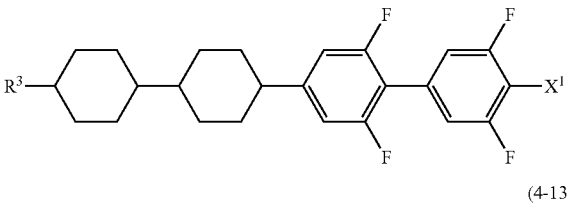 (4-12)
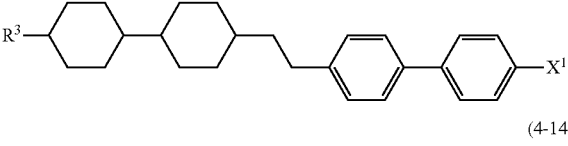 (4-13)
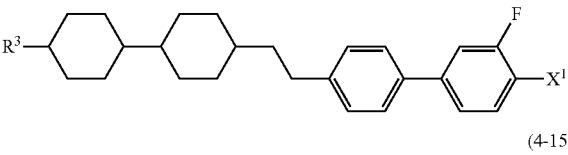 (4-14)
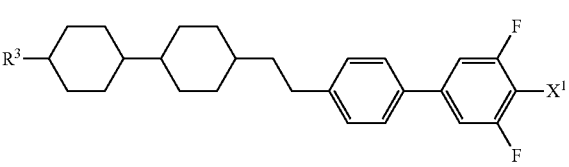 (4-15)
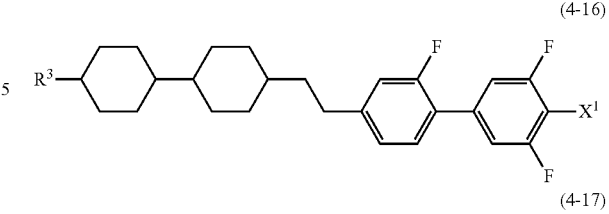 (4-16)
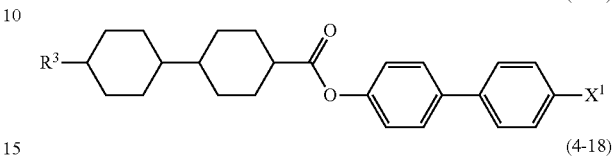 (4-17)
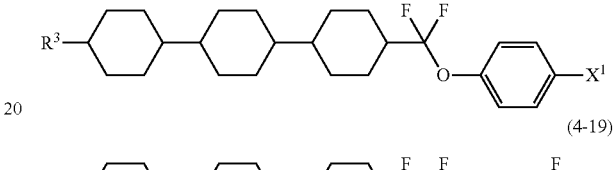 (4-18)
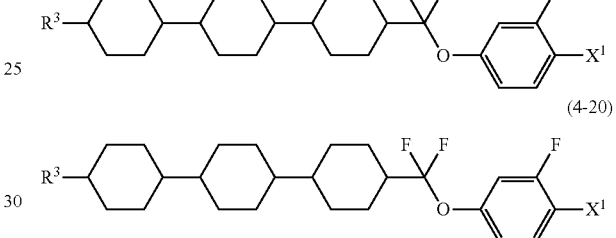 (4-19)
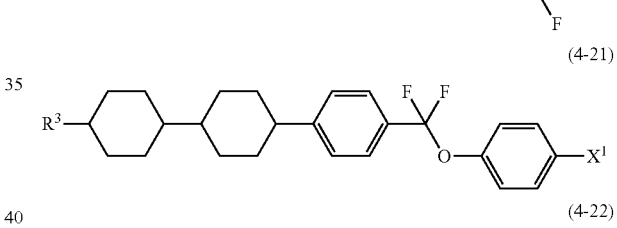 (4-20)
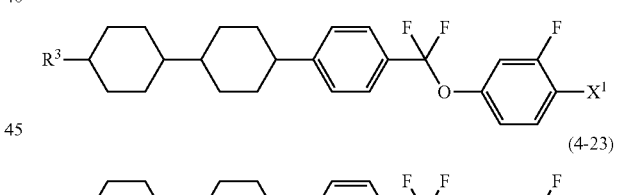 (4-21)
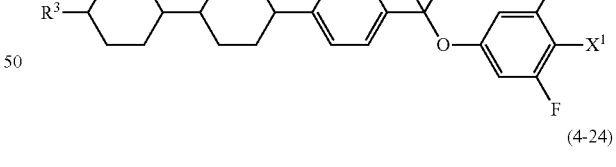 (4-22)
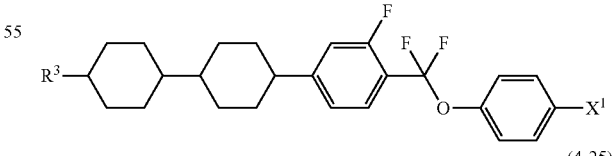 (4-23)
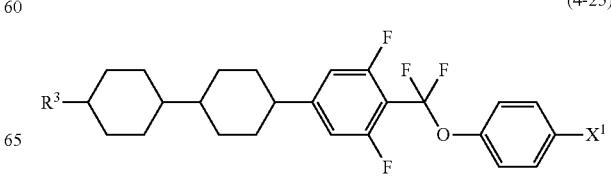 (4-24)
(4-25)

(4-26) 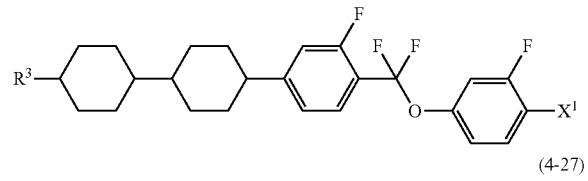
(4-27) 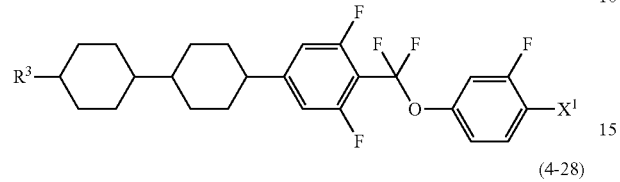
(4-28) 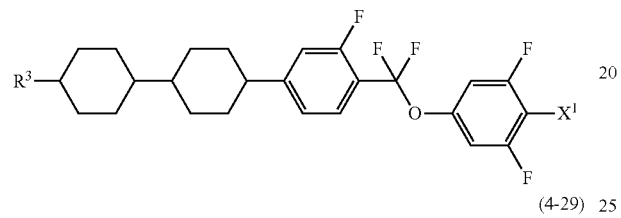
(4-29) 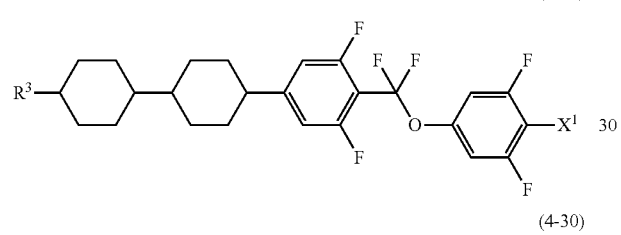
(4-30) 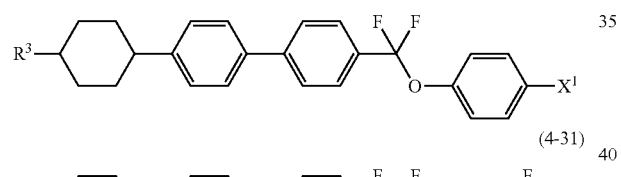
(4-31) 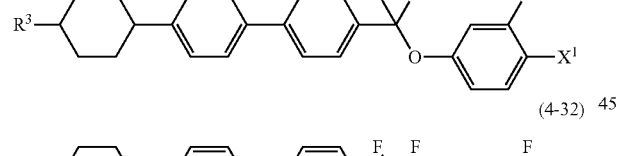
(4-32) 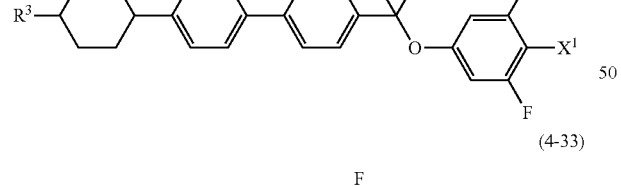
(4-33) 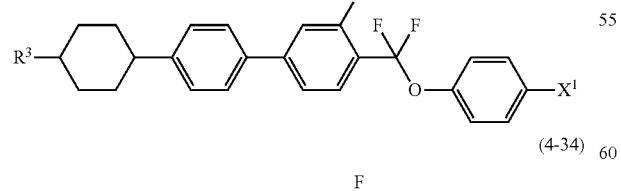
(4-34) 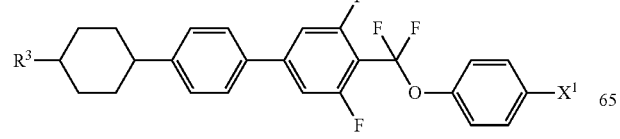
(4-35) 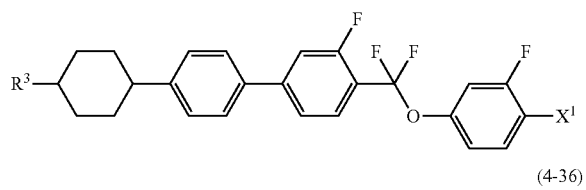
(4-36) 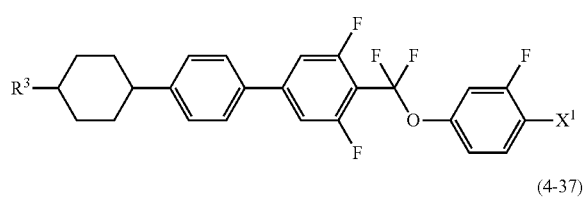
(4-37) 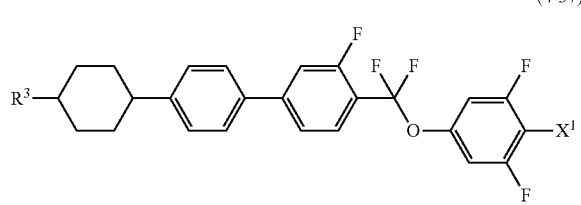
(4-38) 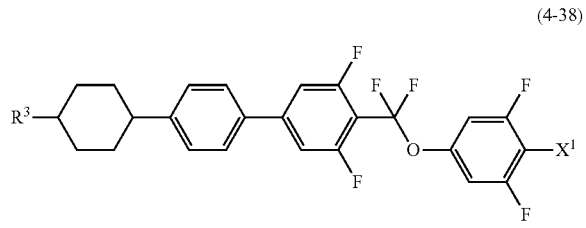
(4-39) 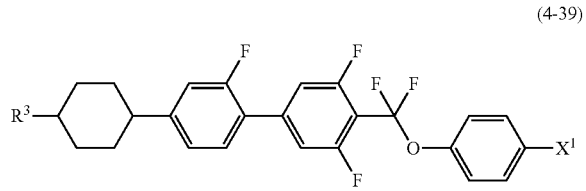
(4-40) 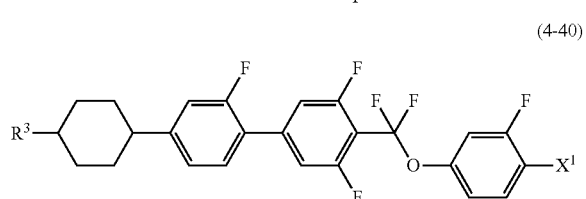
(4-41) 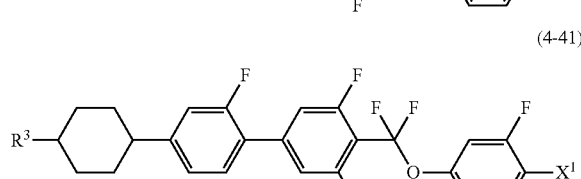
(4-42) 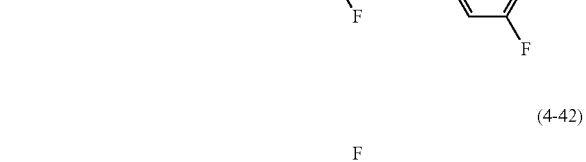
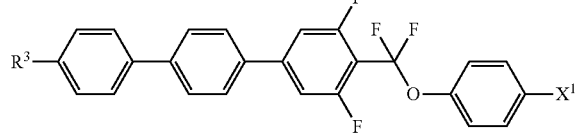

(4-43)
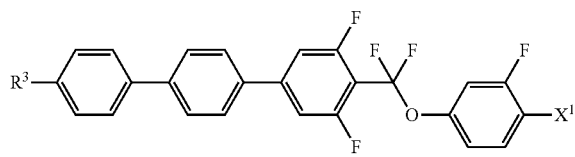

(4-44)
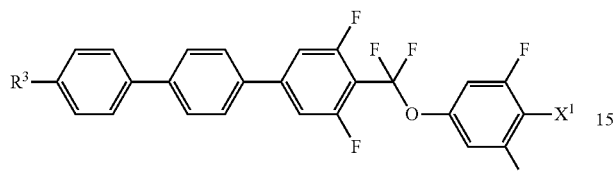

(4-45)
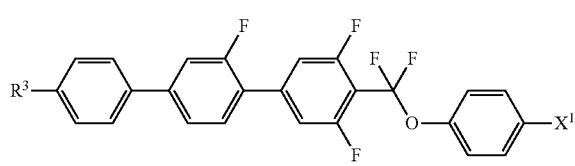

(4-46)
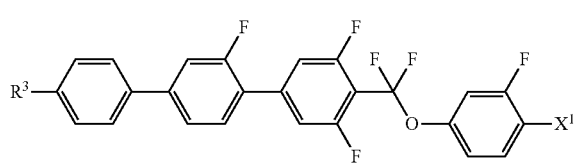

(4-47)
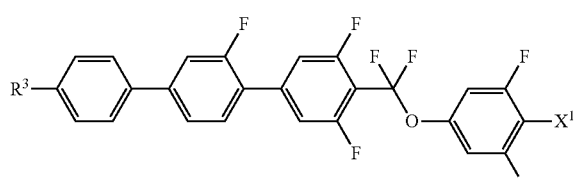

(4-48)
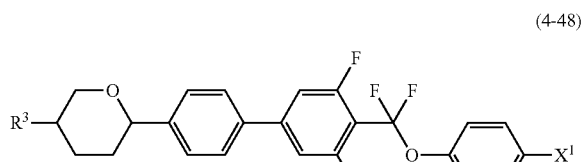

(4-49)
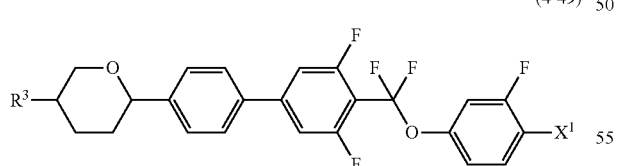

(4-50)
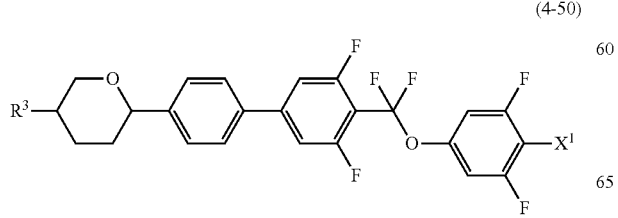

(4-51)
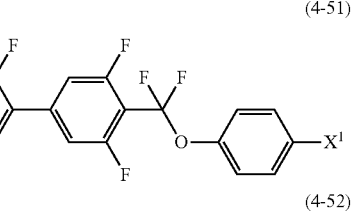

(4-52)
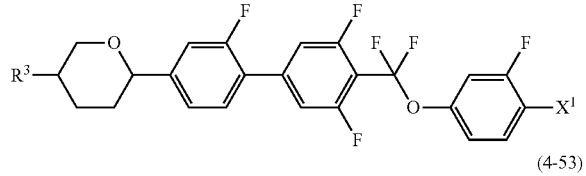

(4-53)
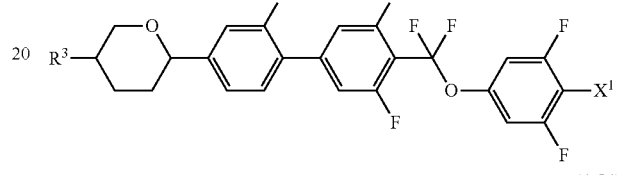

(4-54)
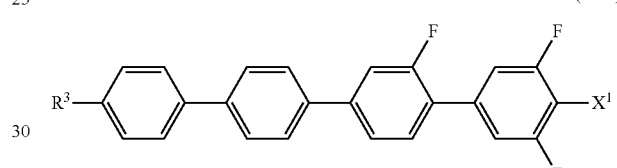

In the formulas, the definitions of $R^3$ and $X^1$ are just the same as those described previously.

The compounds (2) to (4), that is to say, the component B, is used in the preparation of the liquid crystal composition for use in a TFT mode and a PSA mode, since they have positive dielectric anisotropy ($\Delta\epsilon$) and an particularly excellent thermal or chemical stability. The content of the component B in the liquid crystal composition of the invention is suitably in the range of 1% to 99% by weight, preferably in the range of 10% to 97% by weight, and more preferably 40% to 95% by weight based on the total weight of the liquid crystal composition. The viscosity can be adjusted by a further addition of the compounds (12) to (14), that is to say, the component E.

Desirable examples of the compound (5) described above, that is to say, the component C, include the compounds (5-1) to (5-64).

(5-1)
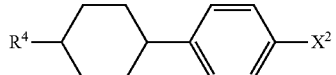

(5-2)
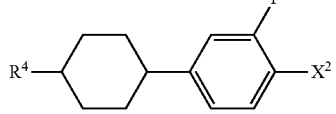

(5-3)
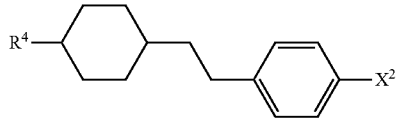

(5-4) 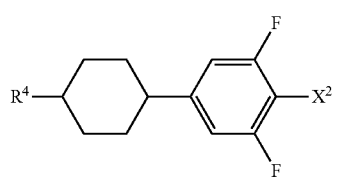
(5-5) 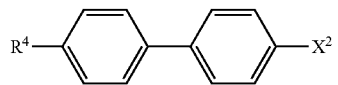
(5-6) 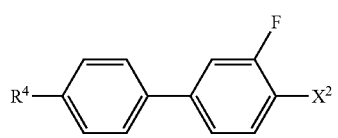
(5-7) 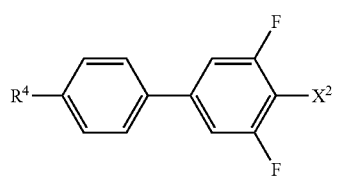
(5-8) 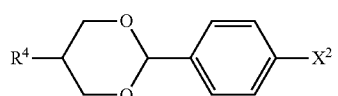
(5-9) 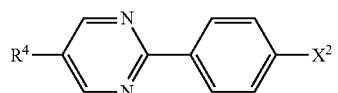
(5-10) 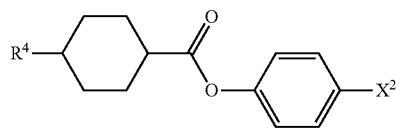
(5-11) 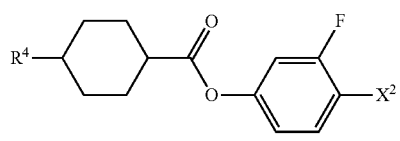
(5-12) 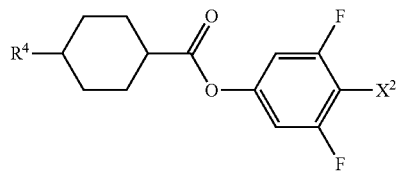
(5-13) 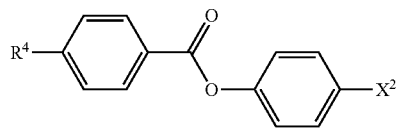
(5-14) 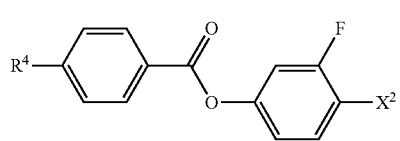

-continued
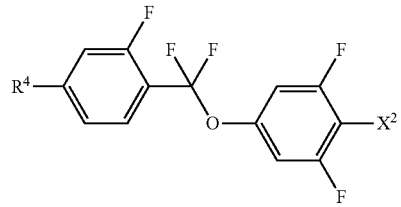
(5-24)
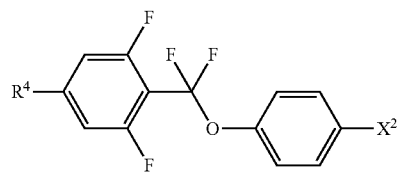
(5-25)
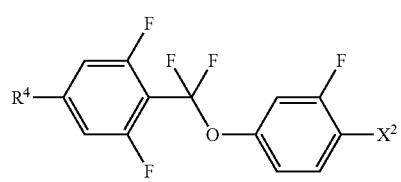
(5-26)
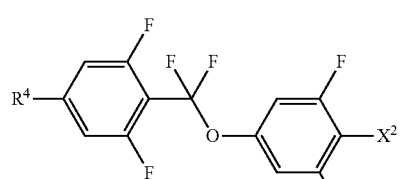
(5-27)
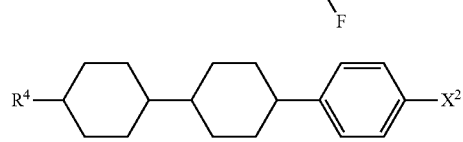
(5-28)
(5-29)
(5-30)
(5-31)
(5-32)
(5-33)
-continued
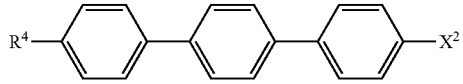
(5-34)
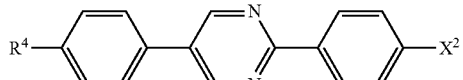
(5-35)
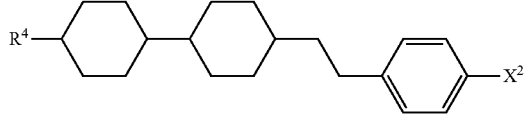
(5-36)
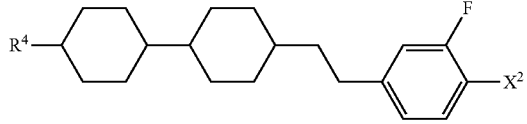
(5-37)
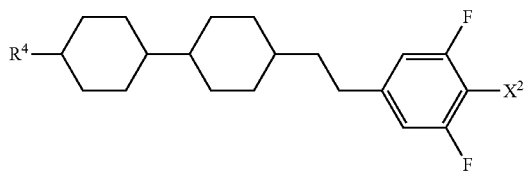
(5-38)
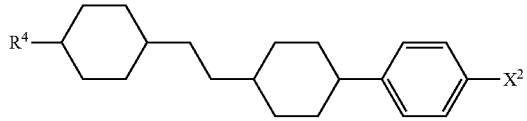
(5-39)
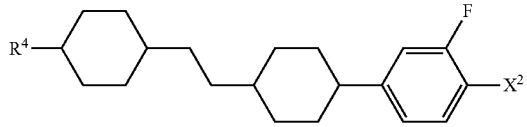
(5-40)
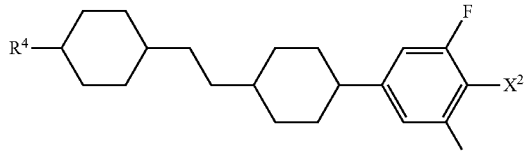
(5-41)
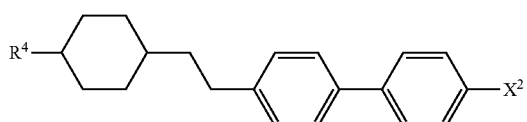
(5-42)
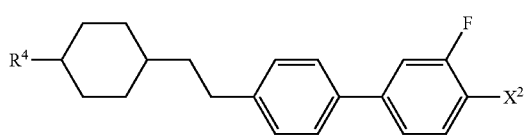
(5-43)

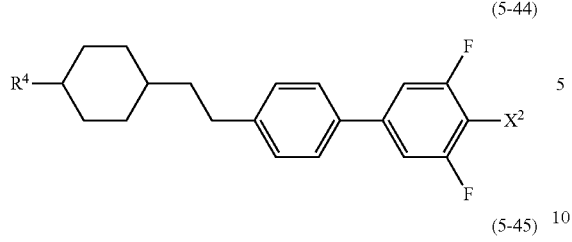
(5-44)
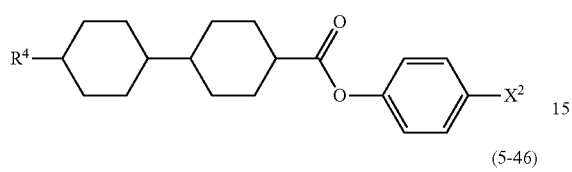
(5-45)
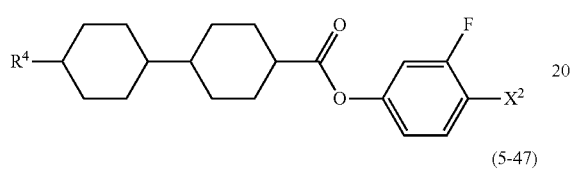
(5-46)
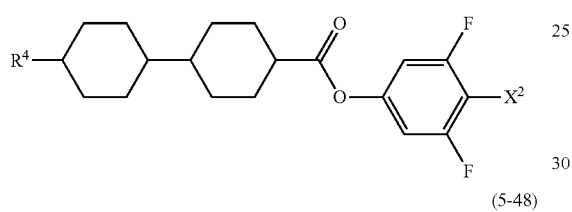
(5-47)
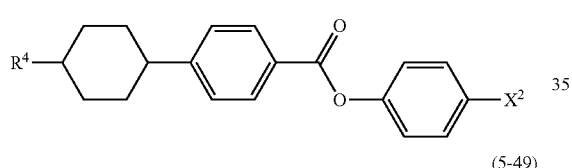
(5-48)
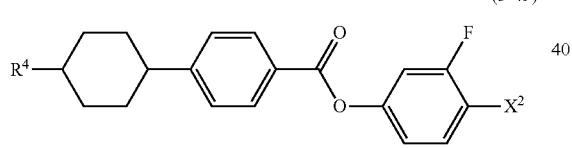
(5-49)
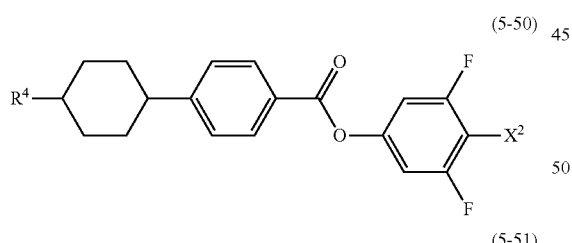
(5-50)
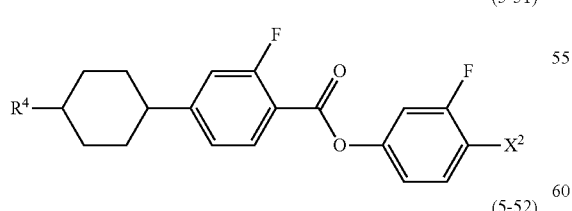
(5-51)
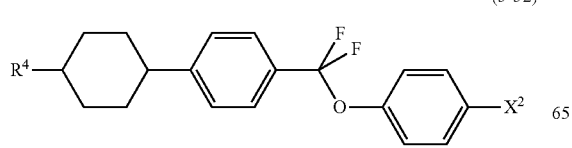
(5-52)
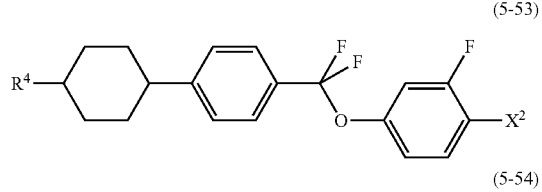
(5-53)
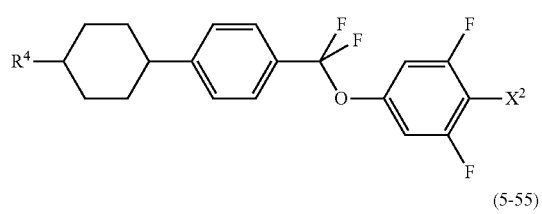
(5-54)
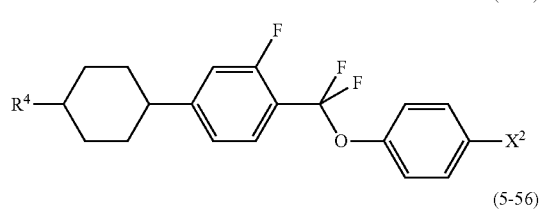
(5-55)
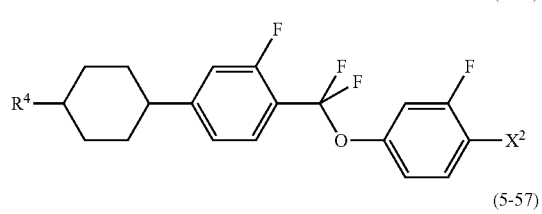
(5-56)
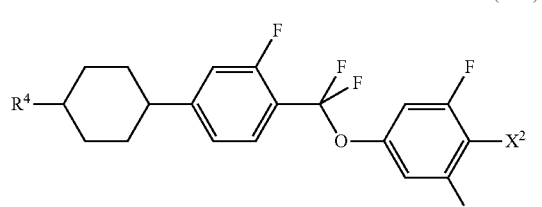
(5-57)
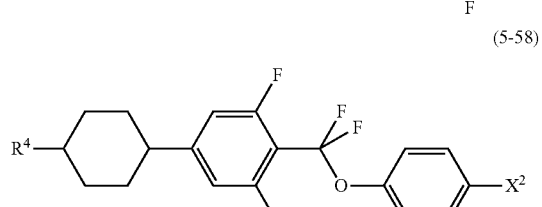
(5-58)
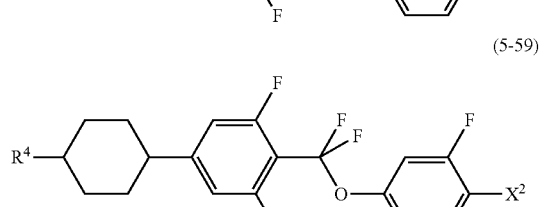
(5-59)
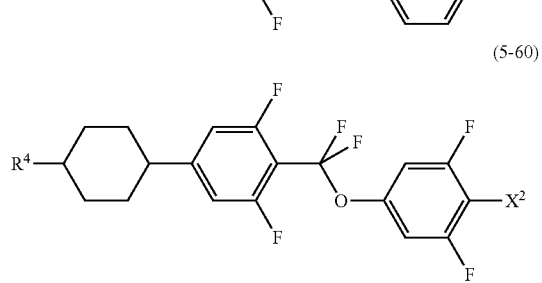
(5-60)

(5-61)
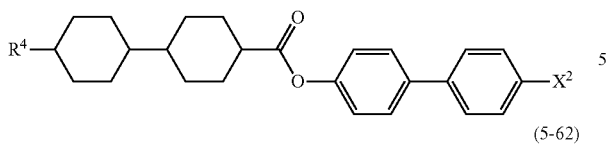

(5-62)
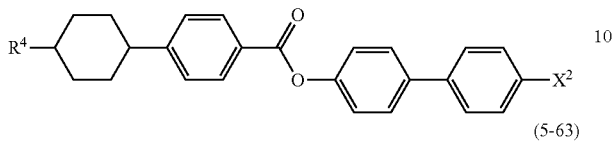

(5-63)
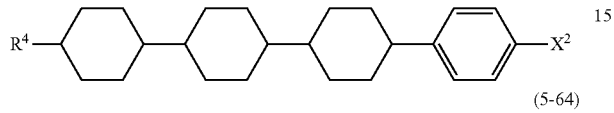

(5-64)
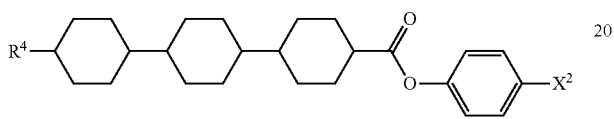

In the formulas, the definitions of $R^4$ and $X^2$ are just the same as those described previously.

The compound (5), that is to say the component C, is mainly used in the preparation of the liquid crystal composition for use in a STN mode, a TN mode and a PSA mode, since the dielectric anisotropy ($\Delta\epsilon$) is positive and the value is particularly large. The threshold voltage of the composition can be decreased by the addition of the component C. The viscosity can be adjusted, the refractive index anisotropy ($\Delta n$) can be adjusted, and the temperature range of a liquid crystal phase can be increased. Furthermore, the component C can also be utilized for an improvement of the steepness.

The content of the component C is suitably in the range of 0.1% to 99.9% by weight, preferably in the range of 10% to 97% by weight, and more preferably in the range of 40% to 95% by weight based on the total amount of the composition in the preparation of the liquid crystal composition for use in a STN mode or a TN mode. The threshold voltage, the temperature range of a liquid crystal phase, the refractive index anisotropy ($\Delta n$), the dielectric anisotropy ($\Delta\epsilon$), the viscosity and so forth can be adjusted by the addition of a component which will be described below.

The component D, that is to say, the compounds (6) to (11), are desirable in the preparation of the liquid crystal composition of the invention which has negative dielectric anisotropy ($\Delta\epsilon$) for use in a VA (vertical alignment) mode, a PSA (polymer sustained alignment) mode and so forth.

Desirable examples of the compounds (6) to (11), that is to say, the component D, include the compounds (6-1) to (6-6), the compounds (7-1) to (7-15), the compound (8-1), the compounds (9-1) to (9-3), the compounds (10-1) to (10-11) and the compounds (11-1) to (11-10).

(6-1)
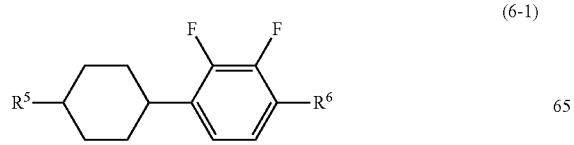

(6-2)
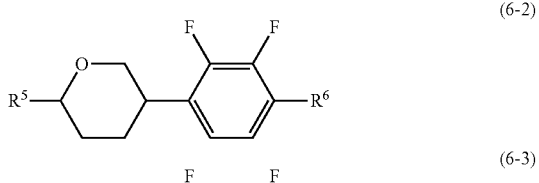

(6-3)
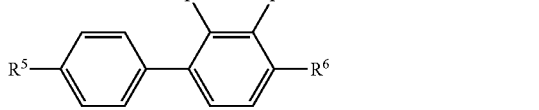

(6-4)
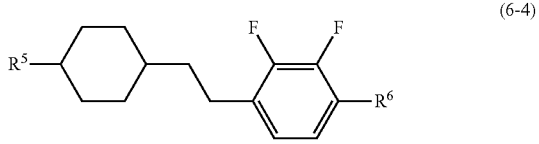

(6-5)
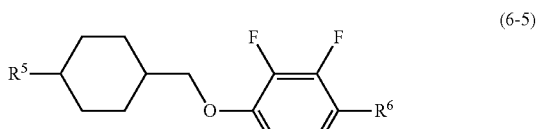

(6-6)
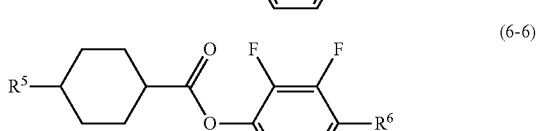

(7-1)
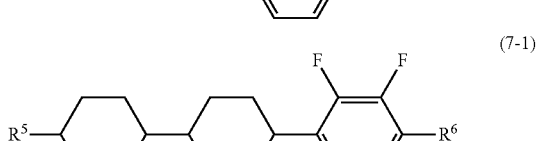

(7-2)
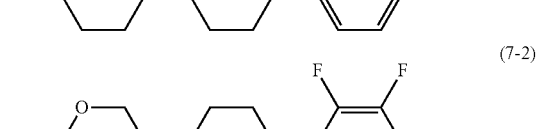

(7-3)
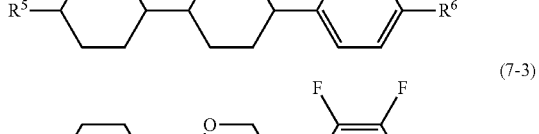

(7-4)
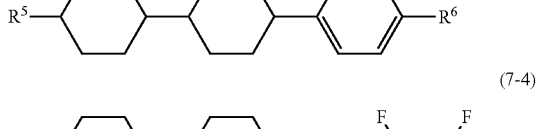

(7-5)
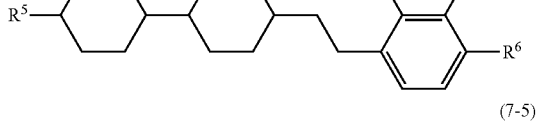

(7-6)
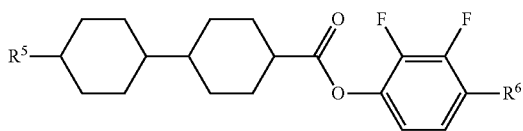

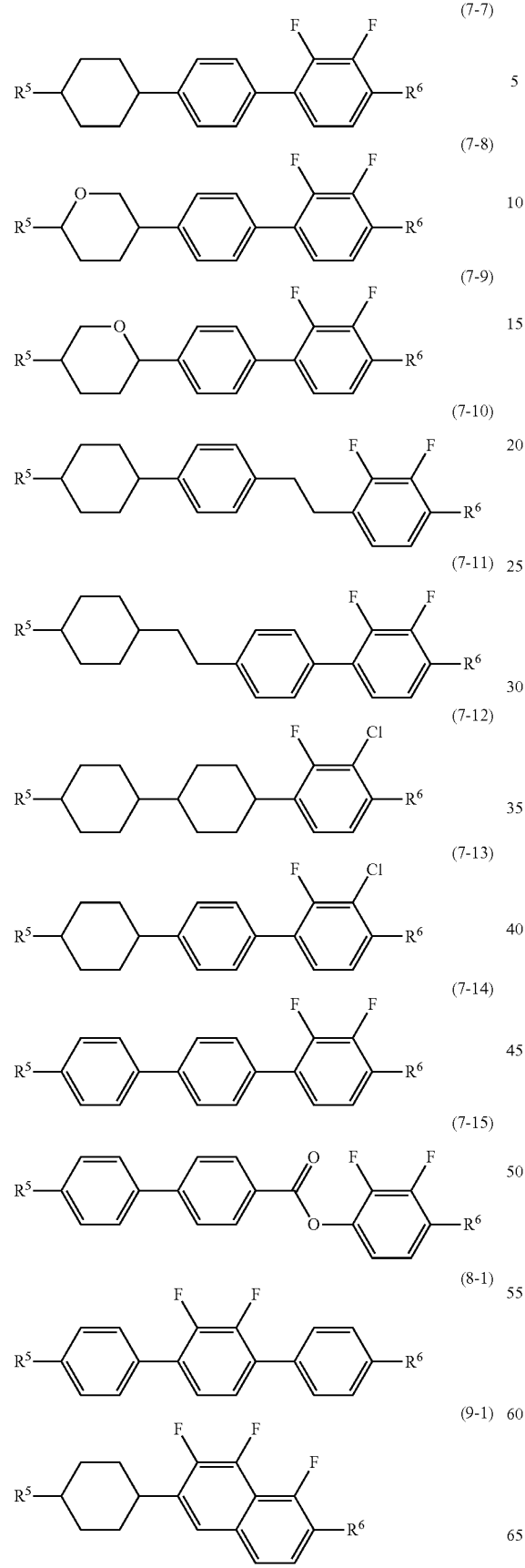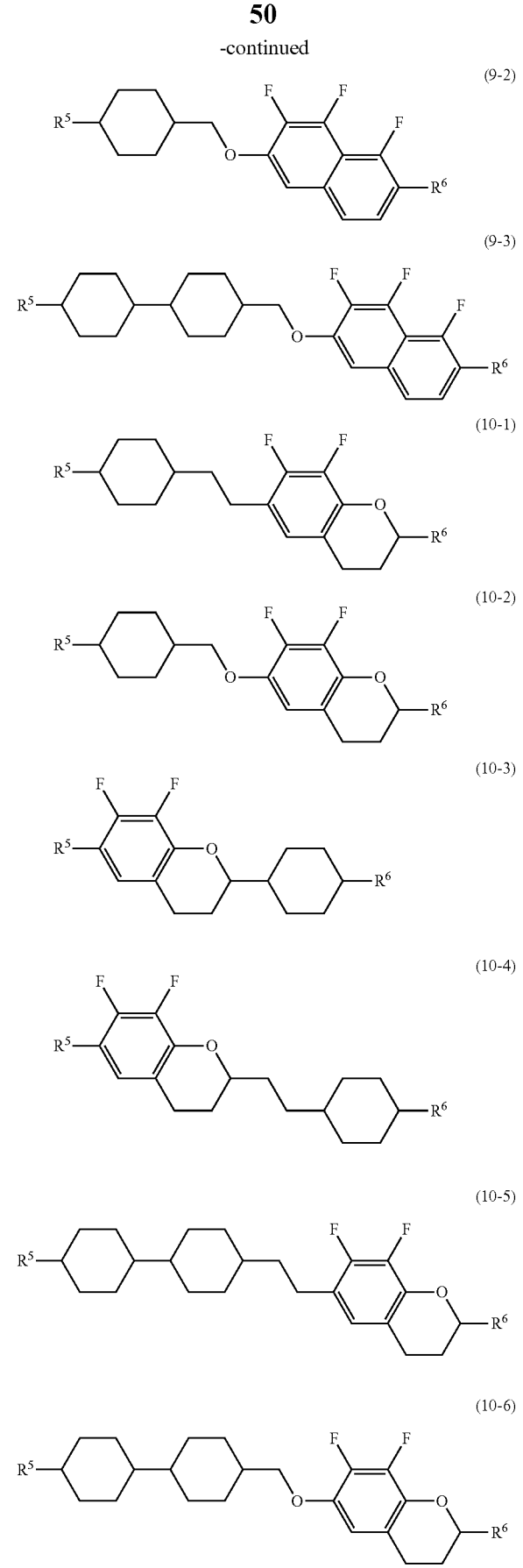

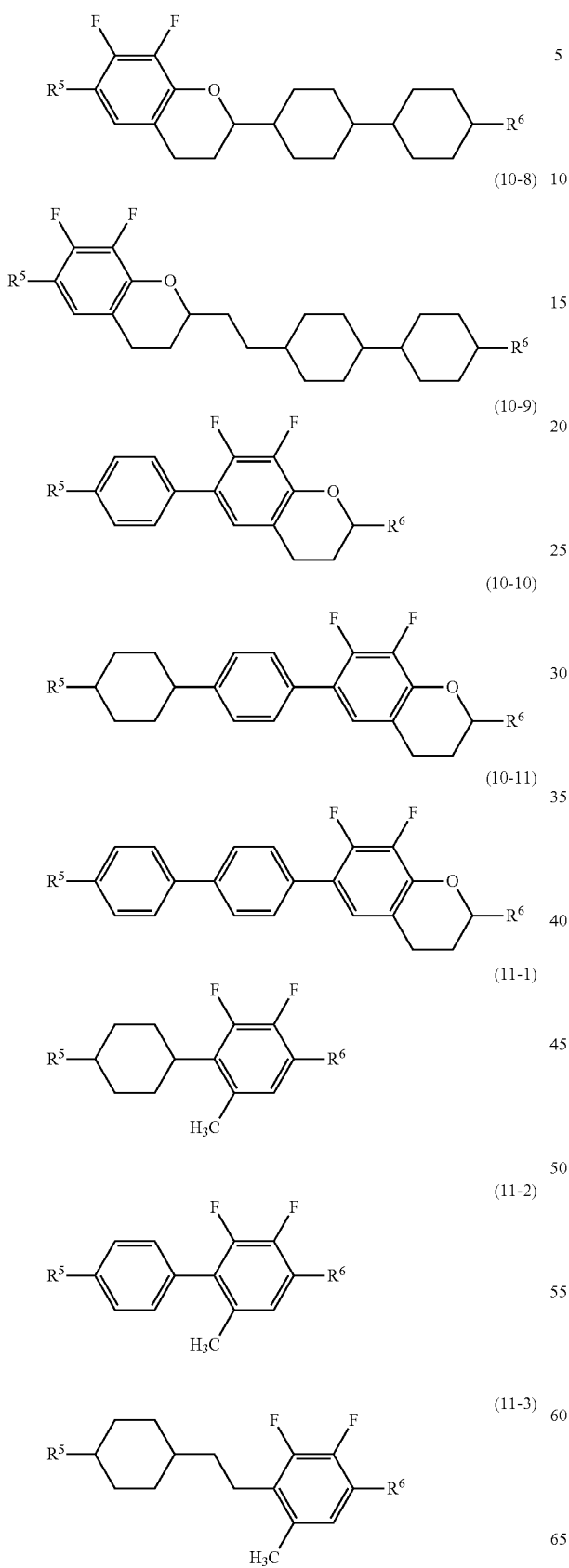
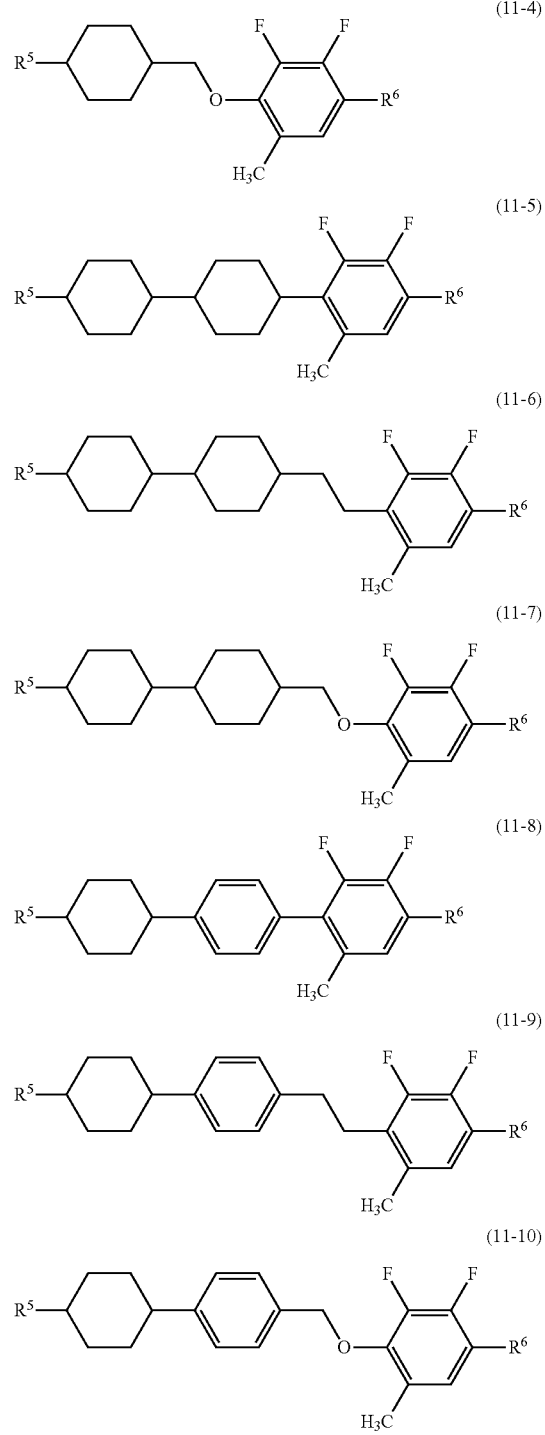

In the formulas, the definitions of $R^5$ and $R^6$ are just the same as those described previously.

The compounds of the component D are mainly used in the liquid crystal composition having negative dielectric anisotropy ($\Delta\epsilon$) for use in a VA mode and a PSA mode. As the content of the component D is increased, the threshold voltage of the composition decreases, however, the viscosity increases. Accordingly, it is desirable that the content of the component D should decrease as long as the required value of the threshold is satisfied. On the other hand, it is desirable that the content should be more than 40% by weight to attain a sufficient driving voltage, since the absolute value of the dielectric anisotropy (Δε) is about 5.

The compound (6) among the component D is effective mainly in adjusting the threshold voltage, adjusting the viscosity, or adjusting the refractive index anisotropy (Δn), since it is a two-ring compound. The compounds (7) and (8) are effective in increasing the clearing point, increasing the temperature range of a nematic phase, decreasing the threshold voltage or increasing the refractive index anisotropy (Δn) for instance, since it is a three-ring compound. The compounds (9), (10) and (11) are effective in decreasing the threshold voltage for instance.

The content of the component D is preferably 40% by weight or more, and more preferably in the range of 50% to 95% by weight based on the total amount of the composition, in the preparation of the composition for use in a VA mode and a PSA mode. The elastic constant can be adjusted and the voltage-transmission curve of the composition can be adjusted by the addition of the component D. It is desirable that the content of the component D should be 30% by weight or less based on the total amount of the composition when the component D is added to a composition having positive dielectric anisotropy (Δε).

Desirable examples of the compounds (12), (13) and (14), that is to say, the component E, include the compounds (12-1) to (12-11), the compounds (13-1) to (13-19) and the compounds (14-1) to (14-6), respectively.

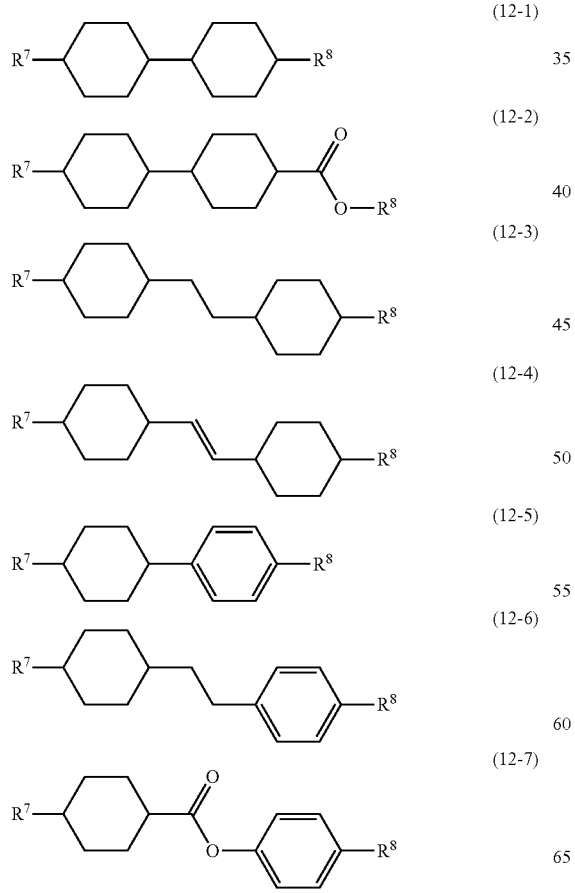

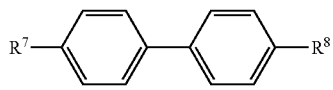
(12-8)

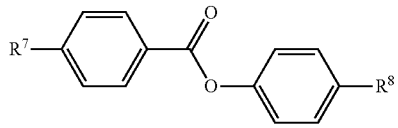
(12-9)

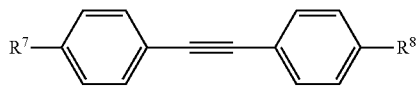
(12-10)

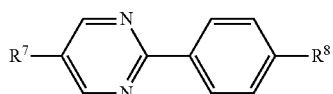
(12-11)

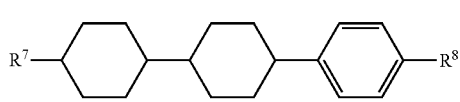
(13-1)

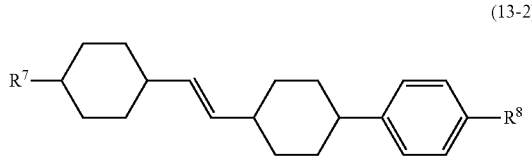
(13-2)

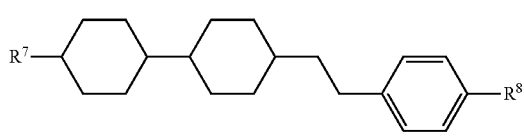
(13-3)

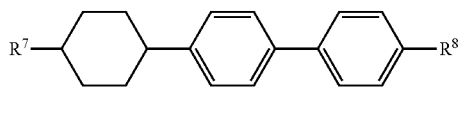
(13-4)

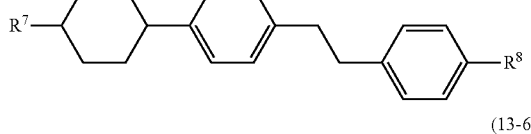
(13-5)

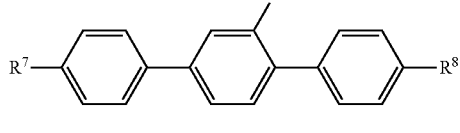
(13-6)

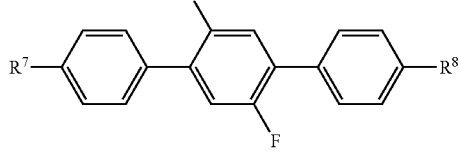
(13-7)

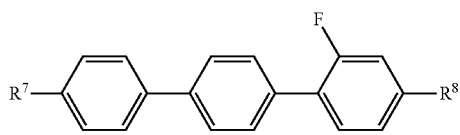
(13-8)

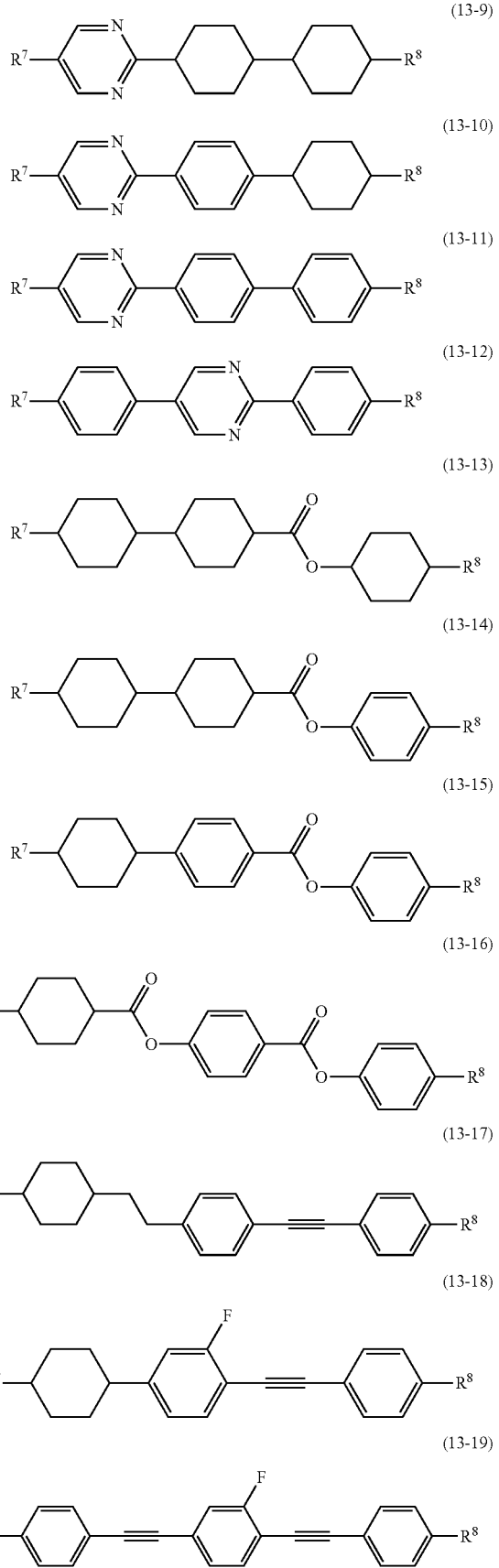

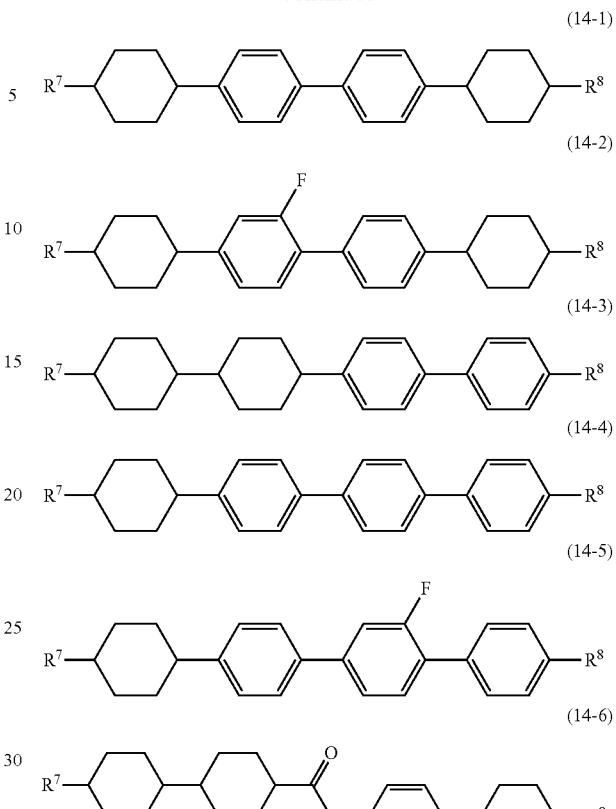

In the formulas, the definitions of $R^7$ and $R^8$ are just the same as those described previously.

The compounds (12) to (14), that is to say, the component E, is close to neutral, since the absolute value of the dielectric anisotropy ($\Delta\epsilon$) is small. The compound (12) is effective mainly in adjusting the viscosity or adjusting the refractive index anisotropy ($\Delta n$). The compounds (13) and (14) are effective in increasing the temperature range of a nematic phase, which is caused by an increase in the clearing point for instance, or adjusting the refractive index anisotropy ($\Delta n$).

As the content of the compound included in the component E is increased, the threshold voltage of the liquid crystal composition increases and the viscosity decreases. Accordingly, it is desirable that the content should increase as long as the required value of the threshold voltage of the liquid crystal composition is satisfied. The content of the component E is preferably 30% by weight or more, and more preferably 50% by weight or more based on the total amount of the composition, in the preparation of the liquid crystal composition for use in a TFT mode or a PSA mode. The content of the component E is preferably 30% by weight or more, and more preferably 40% by weight or more based on the total amount of the composition, in the preparation of the liquid crystal composition for use in a TN mode, a STN mode or a PSA mode.

It is desirable that the liquid crystal composition of the invention should include at least one of the compounds (1-1) and (1-2) in the range of 0.1% to 99% by weight for exhibiting excellent characteristics.

The liquid crystal composition of the invention is generally prepared according to known methods such as the mutual dissolution of necessary components at a high temperature, for example. An additive that is well-known to a person skilled in the art may be added to the composition depending on its intended use. For example, a liquid crystal composition including an optically active compound, or including a polymerizable compound and a polymerization initiator, those of which will be described below, or a liquid crystal composition for use in a GH mode, to which a dye is added, can be prepared. The additive is generally well known to a person skilled in the art, and is described in the literature and so forth in detail.

In the liquid crystal composition of the invention, one or more optically active compounds may be added to the liquid crystal composition of the invention descried above.

A known chiral dopant is added as an optically active compound. The chiral dopant is effective in inducing a helical structure in liquid crystals, adjusting a necessary twist angle and thus preventing a reverse twist. Examples of the chiral dopant include the following optically active compounds (Op-1) to (Op-13).

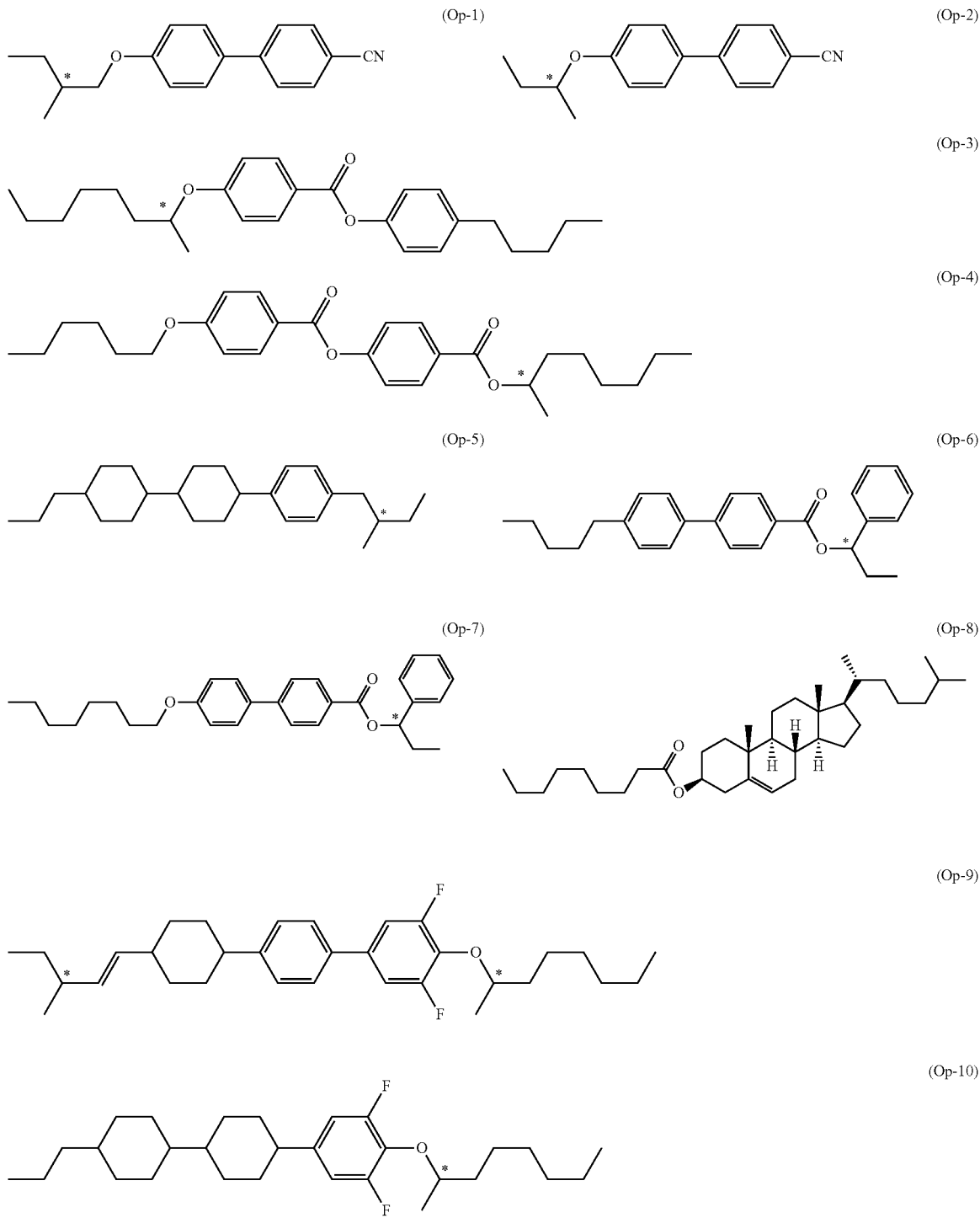

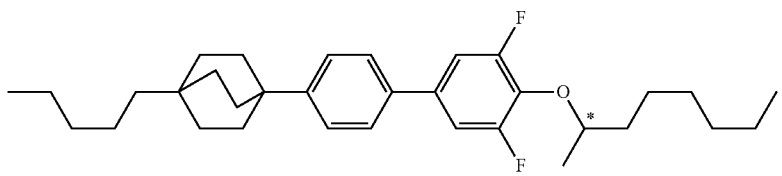

(Op-11)

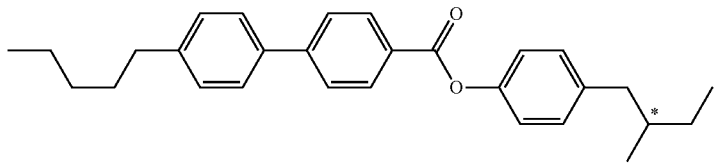

(Op-12)

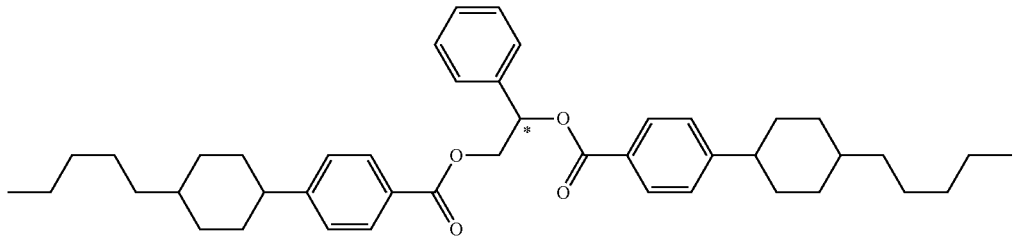

(Op-13)

A helical pitch can be adjusted by the addition of this optically active compound to the liquid crystal composition of the invention. It is desirable to adjust the helical pitch to the range of 40 micrometers to 200 micrometers in a liquid crystal composition for use in a TFT mode and a TN mode. It is desirable to adjust the helical pitch to the range of 6 micrometers to 20 micrometers in a liquid crystal composition for use in a STN mode. It is desirable to adjust the helical pitch to the range of 1.5 micrometers to 4 micrometers for use in a BTN (bistable twisted nematic) mode. Two or more optically active compounds may be added for the purpose of adjusting the temperature dependence of the helical pitch.

The liquid crystal composition of the invention can be used for a liquid crystal composition having a GH mode by the addition of a dichroic dye such as a merocyanine, styryl, azo, azomethine, azoxy, quinophthalone, anthraquinone or tetrazine compound.

The liquid crystal composition of the invention can be used as a liquid crystal composition for a NCAP-device prepared by micro-encapsulating nematic liquid crystals, and for a polymer-distributed liquid crystal display device (PDLCD) prepared by forming a three-dimensional network polymer in liquid crystals, such as a polymer network liquid crystal display device (PNLCD), and also for use in an ECB (electrically controlled birefringence) mode or a DS mode.

The liquid crystal composition of the invention can be used as a liquid crystal composition for use in a PSA (polymer sustained alignment) mode by the addition of a polymerizable compound. Examples of the polymerizable compound include compounds having polymerizable groups such as acrylates, methacrylates, vinyl compounds, vinyloxy compounds, propenyl ethers, epoxy compounds, vinyl ketones and oxetanes. The polymerizable compound is polymerized on irradiation with ultraviolet light or the like, preferably in the presence of a suitable initiator such as a photopolymerization initiator. Suitable conditions for the polymerization, and a suitable type and a suitable amount of the initiator are known to a person skilled in the art and are described in the literature. For example, Irgacure 651 (registered trademark), Irgacure 184 (registered trademark) or Darocure 1173 (registered trademark) (Ciba Japan K.K.), each of which is a photo-initiator, is suitable for radical polymerization.

The invention will be explained below in more detail by way of examples. In each example, the symbols C, SA, SB, SX, N and I stand for crystals, a smectic A phase, a smectic B phase, a smectic phase which the phase structure is not yet analyzed, a nematic phase and an isotropic phase, respectively. The degree Celsius (° C.) was used for the unit of the phase transition temperature.

EXAMPLES

The invention will be explained below in more detail based on examples, and the invention is not limited to the examples at the same time. The term "%" means "% by weight," unless otherwise noted.

Analytical methods will be explained first, since the resulting compounds herein were identified on the basis of nuclear magnetic resonance spectra obtained by means of $^1$H-NMR analysis, gas chromatograms obtained by means of gas chromatography (GC) analysis and so forth.

$^1$H-NMR Analysis:

A model DRX-500 apparatus (made by Bruker BioSpin Corporation) was used for measurement. Samples prepared in the examples and so forth were dissolved in deuterated solvents such as $CDCl_3$ in which the samples were soluble, and the measurement was carried out under the conditions of room temperature, twenty-four times of accumulation and 500 MHz. Tetramethylsilane (TMS) was used as the standard reference material for the zero point of the chemical shift (δ values).

GC Analysis

A Gas Chromatograph Model GC-14B made by Shimadzu Corporation was used for measurement. A capillary column CBP1-M25-025 (length 25 m, bore 0.22 mm, film thickness 0.25 micrometer; dimethylpolysiloxane as a stationary liquid phase; non-polar) made by Shimadzu Corporation was used. Helium was used as a carrier gas, and its flow rate was adjusted to 1 ml per minute. The temperature of the sample injector was set at 280° C. and the temperature of the detector (FID) was set at 280° C.

A sample was dissolved in toluene to give a 1% by weight solution, and then 1 microliter of the resulting solution was injected into the sample injector.

Chromatopac Model C-R6A made by Shimadzu Corporation or its equivalent was used as a recorder. The resulting gas chromatogram showed the retention time of the peaks and the values of the peak areas corresponding to the component compounds.

Incidentally, chloroform or hexane, for example, may also be used as a solvent for diluting the sample. The following capillary columns may also be used: DB-1 (length 30 m, bore 0.32 mm, film thickness 0.25 micrometer) made by Agilent Technologies Inc., HP-1 (length 30 m, bore 0.32 mm, film thickness 0.25 micrometer) made by Agilent Technologies Inc., Rtx-1 (length 30 m, bore 0.32 mm, film thickness 0.25 micrometer) made by Restek Corporation, BP-1 (length 30 m, bore 0.32 mm, film thickness 0.25 micrometer) made by SGE International Pty. Ltd, and so forth.

The ratio of the peak areas in the gas chromatogram corresponds to the ratio of component compounds. In general, the percentage by weight of each component compound in an analytical sample is not completely the same as the percentage of each peak area in the analytical sample. In the invention, however, the percentage by weight of the component compound in the analytical sample corresponds substantially to the percentage of the peak area in the analytical sample, because the correction coefficient is essentially 1 (one) when the columns described above are used.

Samples for the Measurement of the Physical Properties of Liquid Crystal Compounds and so Forth Two kinds of samples are used for measuring the physical properties of a liquid crystal compound: one is the compound itself, and the other is a mixture of the compound and mother liquid crystals.

In the latter case using a sample in which the compound is mixed with mother liquid crystals, the measurement is carried out according to the following method. First, the sample is prepared by mixing 15% by weight of the liquid crystal compound obtained and 85% by weight of the mother liquid crystals. Then, extrapolated values are calculated from the measured values of the resulting sample by applying the following formula (extrapolation method). The extrapolated values are regarded as the physical properties of this compound.

[Extrapolated value]=(100×[Measured value of sample]−[by weight of mother liquid crystals]×[Measured value of mother liquid crystals])/[% by weight of liquid crystal compound]

When a smectic phase appears at 25° C. or crystals deposit at 25° C. in the sample described above, the ratio of the liquid crystal compound to the mother liquid crystals is changed in the order of (10% by weight: 90% by weight), (5% by weight: 95% by weight) and (1% by weight: 99% by weight). The physical properties of the sample are measured at the ratio in which the smectic phase does not appear at 25° C. or the crystals does not deposit at 25° C. Extrapolated values are determined according to the above equation, and are regarded as the physical properties of the liquid crystal compound.

There are a variety of mother liquid crystals used for measurement and, for example, each component (% by weight) of the mother liquid crystals (A) is shown below.

Mother liquid crystals (A):

$C_3H_7$—⬡—COO—⌬—$OC_2H_5$    17.2%

$C_3H_7$—⬡—COO—⌬—$OC_4H_9$    27.6%

$C_4H_9$—⬡—COO—⌬—$OC_2H_5$    20.7%

$C_5H_{11}$—⬡—COO—⌬—$OCH_3$    20.7%

$C_5H_{11}$—⬡—COO—⌬—$OC_2H_5$    13.8%

Incidentally, in the case where the physical properties of a liquid crystal composition were measured, the liquid crystal composition itself was used as a sample.

Methods for Measurements of the Physical Properties of Liquid Crystal Compounds and so Forth The physical properties of compounds were measured according to the following methods. Most are measurement methods described in the Standard of Electronic Industries Association of Japan, EIAJ•ED-2521A, or the modified methods. No TFT was attached to a TN device or a VA device used for measurement.

In measured values, when a liquid crystal compound itself or a liquid crystal composition itself was employed as a sample, a measured value itself was described here as experimental data. When a sample was prepared by mixing the compound with mother liquid crystals, values calculated from measured values according to the extrapolation method was described here as extrapolated values.

Phase Structure and Transition Temperature (° C.)

Measurements were carried out according to the following methods (1) and (2).

(1) A compound was placed on a hot plate of a melting point apparatus (Hot Stage Model FP-52 made by Mettler Toledo International Inc.) equipped with a polarizing microscope, and the phase conditions and their changes were observed with the polarizing microscope, specifying the kind of phase while the compound was heated at the rate of 3° C. per minute.

(2) A sample was heated and then cooled at the rate of 3° C. per minute using a Perkin-Elmer differential scanning calorimeter, a DSC-7 System or a Diamond DSC System. The starting point of an endothermic peak or an exothermic peak caused by the phase change of the sample was obtained by means of the extrapolation, and thus the phase transition temperature was determined.

Hereinafter, the symbol C stood for crystals, which were expressed as $C_1$ or $C_2$ when the kind of crystals was distinguishable. The symbols S and N stood for a smectic phase and a nematic phase, respectively. The symbol Iso stood for a liquid (isotropic). When a smectic B phase or a smectic A were distinguishable in the smectic phases, they were expressed as $S_B$ and $S_A$, respectively. Phase-transition temperatures were expressed as, for example, "C 50.0 N 100.0 Iso", which means that the phase-transition temperature from crystals to a nematic phase (CN) is 50.0° C., and the phase-transition temperature from the nematic phase to a liquid (NI) is 100.0° C. The same applied to the other transition temperatures.

Maximum Temperature of a Nematic Phase ($T_{NI}$; ° C.):

A sample (a liquid crystal composition, or a mixture of a liquid crystal compound and mother liquid crystals) was placed on a hot plate of a melting point apparatus (Hot Stage Model FP-52 made by Mettler Toledo International Inc.) equipped with a polarizing microscope, and was observed with the polarizing microscope while being heated at the rate of 1° C. per minute. A maximum temperature meant a temperature measured when part of the sample began to change from a nematic phase to an isotropic liquid. Hereinafter, the maximum temperature of a nematic phase may simply be abbreviated to "the maximum temperature."

Compatibility at Low Temperatures:

Samples were prepared by mixing a liquid crystal compound with mother liquid crystals so that the amount of the liquid crystal compound became 20% by weight, 15% by weight, 10% by weight, 5% by weight, 3% by weight and 1% by weight, and were placed in glass vials. After these glass vials had been kept in a freezer at −10° C. or −20° C. for a certain period of time, they were observed as to whether or not crystals or a smectic phase had been deposited.

Viscosity (Bulk Viscosity; η; Measured at 20° C.; mPa·s)

It is characterized that as viscosity is decreased, response time decreases.

An E-type viscometer was used for measurement.

Viscosity (Rotational Viscosity; γ1; Measured at 25° C.; mPa·s)

It is characterized that as rotational viscosity is decreased, response time decreases.

Rotational viscosity was measured according to the method described in M. Imai, et al., Molecular Crystals and Liquid Crystals, Vol. 259, p. 37 (1995). A sample (a liquid crystal composition, or a mixture of a liquid crystal compound and mother liquid crystals) was poured into a VA device in which the distance between the two glass substrates (cell gap) was 20 micrometers. A voltage in the range of 30 V to 50 V was applied stepwise with an increment of 1 volt to the device. After a period of 0.2 second with no voltage, a voltage was applied repeatedly under the conditions of only one rectangular wave (rectangular pulse; 0.2 second) and no voltage (2 seconds). The peak current and the peak time of the transient current generated by the applied voltage were measured. The value of rotational viscosity was obtained from the measured values and the calculating equation (8) on page 40 of the paper presented by M. Imai, et al. Incidentally, the value of the dielectric anisotropy (Δε) necessary for the present calculation was obtained by the method described below under the heading "Dielectric Anisotropy."

Refractive Index Anisotropy (Δn; Measured at 25° C.)

Measurement was carried out using an Abbe refractometer with a polarizing plate attached to the ocular, on irradiation with light at a wavelength of 589 nm at a temperature of 25° C. The surface of the main prism was rubbed in one direction, and then a sample (a liquid crystal composition, or a mixture of a liquid crystal compound and mother liquid crystals) was dropped onto the main prism. The refractive index (n∥) was measured when the direction of the polarized light was parallel to that of the rubbing. The refractive index (n⊥) was measured when the direction of polarized light was perpendicular to that of the rubbing. The value of the refractive index anisotropy was calculated from the equation: $\Delta n = n\| - n\perp$.

Dielectric Anisotropy (Δε; Measured at 25° C.)

An ethanol (20 mL) solution of octadecyltriethoxysilane (0.16 mL) was applied to a well-washed glass substrate. The glass substrate was rotated with a spinner, and then heated at 150° C. for 1 hour. A VA device in which the distance (cell gap) was 20 micrometers was assembled from the two glass substrates.

A polyimide alignment film was prepared on glass substrates in a similar manner. After a rubbing-treatment to the alignment film formed on the glass substrates, a TN device in which the distance between the two glass substrates was 9 micrometers and the twist angle was 80 degrees was assembled.

A sample (a liquid crystal composition, or a mixture of a liquid crystal compound and mother liquid crystals) was poured into the resulting VA device, a voltage of 0.5 V (1 kHz, sine waves) was applied to the sample, and then the dielectric constant (ε∥) in the major axis direction of the liquid crystal molecules was measured.

The sample (the liquid crystal composition, or the mixture of the liquid crystal compound and the mother liquid crystals) was poured into the resulting TN device, a voltage of 0.5 V (1 kHz, sine waves) was applied to the sample, and then the dielectric constant (ε⊥) in the minor axis direction of the liquid crystal molecules was measured.

The value of the dielectric anisotropy was calculated from the equation of $\Delta\varepsilon = \varepsilon\| - \varepsilon\perp$.

Example 1

Preparation of trans-5-(4-ethoxy-2,3-difluorophenyl)-2-(trans-4'-propylbi(cyclohexane)-trans-4-yl)tetrahydro-2H-pyran (No. 1)

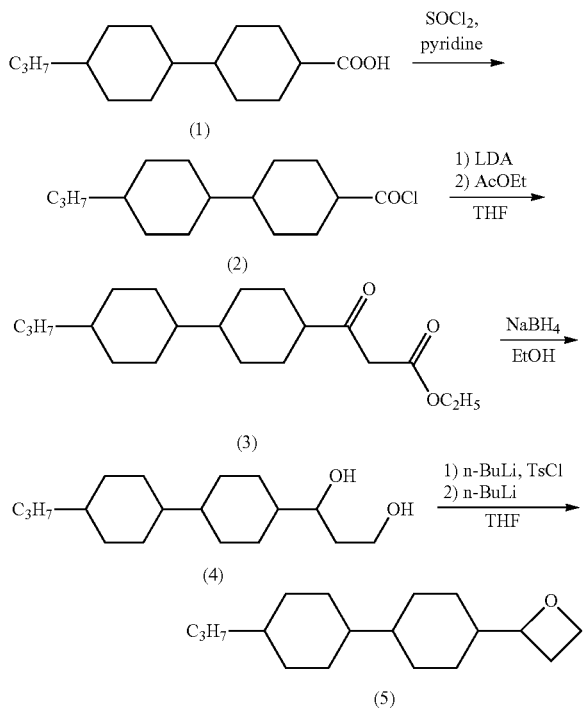

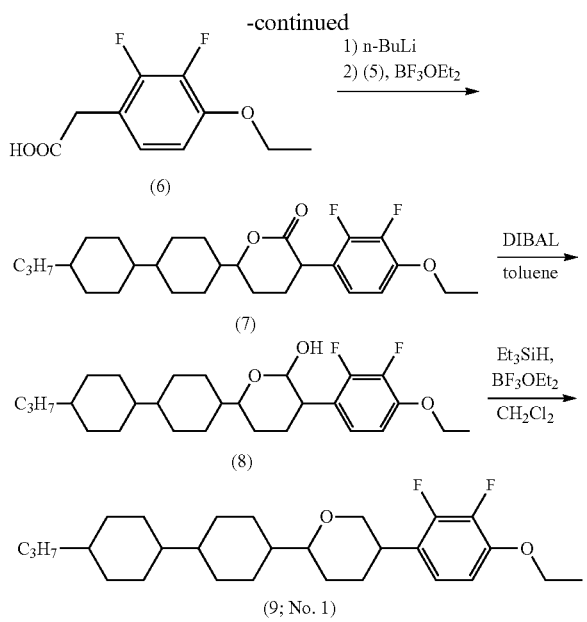

(6)

(7)

(8)

(9; No. 1)

First Step:

trans-4'-Propylbi(cyclohexane)-trans-4-carboxylic acid (1) (30.0 g; 0.119 mmol) in a toluene (200 ml) solution was heated at 50° C. in a reaction vessel under an atmosphere of nitrogen. Pyridine (0.05 ml) and thionyl chloride (14.9 g; 0.125 mmol) were added, and the mixture was stirred for 3 hours. The unreacted thionyl chloride was distilled off at ordinary pressure, and then the solvent was distilled off under reduced pressure to give trans-4'-propylbi(cyclohexane)-trans-4-carboxylic acid chloride (2). The compound was used in the following reaction without further purification.

Second Step:

Lithium diisopropylamide (1.08M in tetrahydrofuran solution; 198 ml; 0.202 mmol) was added to tetrahydrofuran (300 ml) in a reaction vessel under an atmosphere of nitrogen, and the solution was cooled to −65° C. or less. Ethyl acetate (18.2 g; 0.207 mmol), and then a tetrahydrofuran (100 ml) solution of trans-4'-propylbi(cyclohexane)-trans-4-carboxylic acid chloride (2) (32.0 g; 0.119 mmol) obtained in the first step were added dropwise. The reaction mixture was slowly warmed up to room temperature with stirring, and then it was quenched with a saturated aqueous solution of ammonium chloride. Water (500 ml) was added to give two layers. The aqueous layer was extracted with toluene (300 ml) three times. The combined organic layers were washed with water, and dried over anhydrous magnesium sulfate. The solvent was distilled off under reduced pressure. The residue was purified by silica gel column chromatography (silica gel: 100 g; eluent toluene) to give (3-oxo-3-(trans-4'-propylbi(cyclohexane)-trans-4-yl)propion ic acid ethyl ester (3) (34.5 g; 90% yield).

Third Step:

A tetrahydrofuran (100 ml) solution of (3-oxo-3-(trans-4'-propylbi(cyclohexane)-trans-4-yl)propionic acid ethyl ester (3) (34.5 g; 0.107 mmol) obtained in the second step was added dropwise to sodium borohydride (12.1 g; 0.321 mmol) in a ethanol (100 ml) suspension in a reaction vessel at 50° C. or less under an atmosphere of nitrogen, and the mixture was reacted at room temperature for 5 hours. The reaction mixture was quenched with water (500 ml), and ethyl acetate (200 ml) was added to give two layers. The aqueous layer was extracted with ethyl acetate (100 ml) twice. The combined organic layers were washed with water, and dried over anhydrous magnesium sulfate. The solvent was distilled off under reduced pressure. The residue was purified by silica gel column chromatography (silica gel: 100 g; eluent heptane/ethyl acetate=50/50 by volume) to give 1-(trans-4'-propylbi(cyclohexane)-trans-4-yl) propane-1,3-diol (4) (22.7 g; 74% yield).

Fourth Step:

Tetrahydrofuran (100 ml) was added to 1-(trans-4'-propylbi(cyclohexane)-trans-4-yl)propane-1,3-diol (4) (9.4 g; 33.3 mmol) obtained in the third step in a reaction vessel under an atmosphere of nitrogen. n-Butyllithium (1.66 M in n-hexane solution; 20.0 ml; 33.2 mmol) was added dropwise to the solution at temperatures of around −5° C. After 30 minutes of stirring, p-toluenesulfonyl chloride (6.34 g; 33.3 mmol) in a tetrahydrofuran (50 ml) solution was added dropwise. After the reaction mixture had been stirred for 30 minutes, n-butyllithium (1.66M in n-hexane solution; 20.0 ml; 33.2 mmol) was added dropwise at temperatures of around −5° C. The reaction mixture was slowly heated to the refluxing temperature. After the evolution of gas had ceased, the reaction mixture was cooled to room temperature, and quenched with a saturated aqueous solution of ammonium chloride. Water (200 ml) was added to give two layers. The aqueous layer was extracted with toluene (100 ml) twice. The combined organic layers were washed with water, and dried over anhydrous magnesium sulfate. The solvent was distilled off under reduced pressure. The residue was purified by silica gel column chromatography (silica gel: 100 g; eluent toluene) to give 2-(trans-4'-propylbi(cyclohexane)-trans-4-yl)oxetane (5) (6.2 g; 70% yield).

Fifth Step:

n-Butyllithium (1.66 M in n-hexane solution; 33.9 ml; 56.25 mmol) was added dropwise to a THF (100 ml) solution of 2-(4-ethoxy-2,3-difluorophenyl)acetic acid (6) (6.08 g; 28.13 mmol), which was prepared by a general method, in a reaction vessel at −5° C. under an atmosphere of nitrogen. The reaction mixture was then returned to room temperature, and the stirring was continued for another 30 minutes. The solution was cooled to −65° C., and a tetrahydrofuran (30 ml) solution of 2-(trans-4'-propylbi(cyclohexane)-trans-4-yl)oxetane (5) (6.2 g; 23.44 mmol) obtained in the fourth step and a boron trifluoride-diethyl ether complex (3.66 g; 25.79 mmol) were added dropwise. The reaction mixture was returned to room temperature, and it was reacted for 3 hours. A 10% aqueous solution of formic acid (100 ml) was added to the reaction mixture to give two layers. The aqueous layer was extracted with toluene (20 ml) three times. The combined organic layers were washed with water, and dried over anhydrous magnesium sulfate. The solvent was distilled off under reduced pressure. The residue was purified by silica gel column chromatography (silica gel: 50 g; eluent heptane/ethyl acetate=80/20 by volume) to give 3-(4-ethoxy-2,3,-difluorophenyl)-6-(trans-4'-propylbi(cyclohexane)-trans-4-yl)tetrahydro-2H-pyran-2-one (7) (9.35 g; 86.2% yield).

Sixth Step:

Diisobutylaluminum hydride (0.99M in toluene solution; 40.8 ml; 40.4 mmol) was added dropwise to a tetrahydrofuran (100 ml) solution of 3-(4-ethoxy-2,3,-difluorophenyl)-6-(trans-4'-propylbi(cyclohexane)-trans-4-yl)tetrahydro-2H-pyran-2-one (7) (9.35 g; 20.2 mmol) obtained in the fifth step in a reaction vessel at −50° C. or less under an atmosphere of nitrogen, and the mixture was reacted for 3 hours. The reaction mixture was poured into a 10% aqueous solution of formic acid (50 ml) to give two layers. The aqueous layer was extracted with toluene (100 ml) twice. The combined organic layers were washed with water, and dried over anhydrous magnesium sulfate. The solvent was distilled off under reduced pressure to give 3-(4-ethoxy-2, 3-difluorophenyl)-6-(4'-propylbi(cyclohexane)-4-yl)tetrahydro-2H-pyran-2-ol (8) (9.36 g; 99% yield).

Seventh Step:

Triethylsilane (1.93 g) and a boron trifluoride-ethyl ether complex (2.37 g) were added dropwise at −30° C. to a dichloromethane (30 ml) solution of 3-(4'-ethoxy-2,2',3,3'-tetrafluorobiphenyl-4-yl)-6-(4-propylcyclohexyl)tetrahydro-2H-pyran-2-ol (8) (11.0 g; 23.7 mmol) obtained in the sixth step. The reaction mixture was returned to room temperature, and the stirring was continued for another 3 hours. Water (30 ml) was added to give two layers. The organic layer was washed with water, and dried over anhydrous magnesium sulfate. The solvent was distilled off under reduced pressure. The residue was purified by silica gel column chromatography (silica gel: 100 g; eluent: heptane/ ethyl acetate=80/20 by volume) and then by recrystallization (heptane/ethyl acetate=80/20 by volume) to give trans-5-(4-ethoxy-2,3-difluorophenyl)-2-(trans-4'-propylbi(cyclohexane)-trans-4-yl)tetrahydro-2H-pyran (9) (the compound No. 1; 3.1 g; 29% yield).

The chemical shift (δ, ppm) in ¹H-NMR analysis was described below, and the resulting compound was identified as trans-5-(4-ethoxy-2,3-difluorophenyl)-2-(trans-4'-propyl bi(cyclohexane)-trans-4-yl)tetrahydro-2H-pyran(9). The solvent for measurement was CDCl₃.

Chemical shift (δ ppm): 6.80 (dt, 1H), 6.67 (dt, 1H), 4.19 (q, 2H), 4.02-3.97 (m, 1H), 3.37 (t, 1H), 3.07-3.00 (m, 2H), 2.03-1.95 (m, 2H), 1.83-1.67 (m, 10H), 1.46-0.90 (m, 17H) and 0.90-0.75 (m, 5H)

The phase transition temperature of the resulting compound (9), that is to say, the compound No. 1 was as follows.

Transition temperature: C 83.6 SB 250.3 N 310.1 Iso.

Example 2

Preparation of trans-5-(trans-4-(4-ethoxy-2,3-difluorophenyl)cyclohexyl)-2-(trans-4-pentylcyclohexyl) tetrahydro-2H-pyran (No. 41)

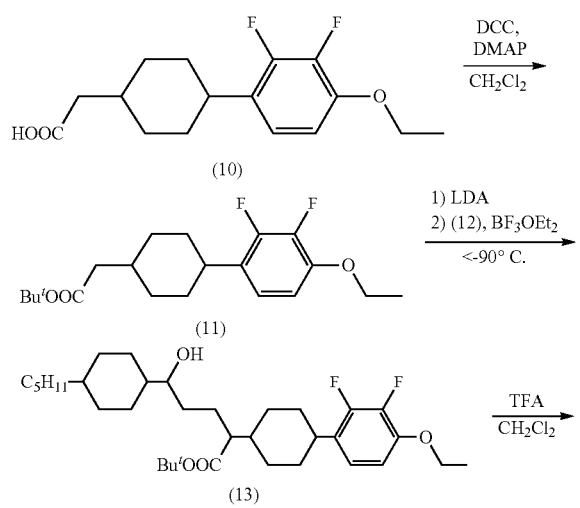

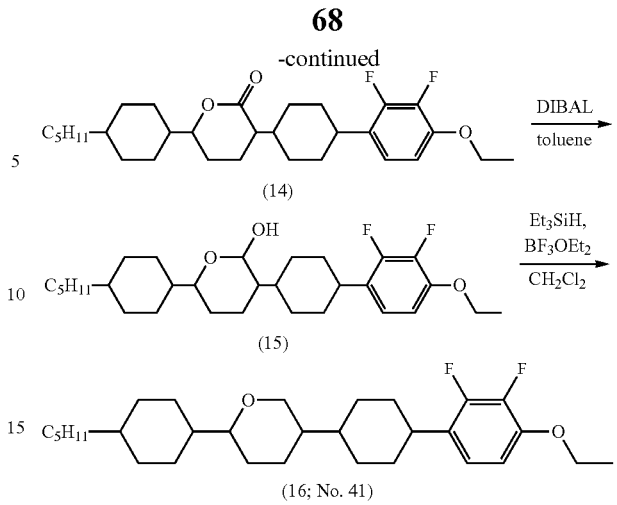

First Step:

N,N'-Dicyclohexylcarbodiimide (DCC; 24.8 g; 0.12 mol) was added to a dichloromethane (300 ml) solution of 2-(trans-4-(4-ethoxy-2,3-difluorophenyl)cyclohexyl)acetic acid (10) (29.8 g; 0.10 mol), 4-di(methylamino)pyridine (DMAP; 1.22 g; 0.01 mol) and t-butanol (8.88 g; 0.12 mol) in a reaction vessel with ice-cooling under an atmosphere of nitrogen. After 8 hours of stirring at room temperature, insoluble matters deposited were filtered off, and water (300 ml) was added to the filtrate to give two layers. The organic layer was washed with water, and dried over anhydrous magnesium sulfate. The solvent was distilled off under reduced pressure. The residue was purified by silica gel column chromatography (silica gel: 100 g; eluent toluene) to give 2-(trans-4-(4-ethoxy-2,3-difluorophenyl)cyclohexyl) acetic acid t-butyl ester (11) (18.3 g; 52% yield).

Second Step:

Lithium diisopropylamide(LDA; 1.98M in tetrahydrofuran solution; 52 ml; 0.103 mol) was added dropwise at −60° C. to a tetrahydrofuran (200 ml) solution of 2-(trans-4-(4-ethoxy-2,3-difluorophenyl)cyclohexyl)acetic acid t-butyl ester (11) (18.3 g; 51.7 mmol) obtained in the first step, and the mixture was stirred at the same temperature for 1 hour. The reaction mixture was cooled to −90° C. or less. A tetrahydrofuran (10 ml) solution of 2-(trans-4-pentylcyclohexyl)oxetane (12) (9.05 g; 43.1 mmol) which was prepared by a general method and a boron trifluoride-ethyl ether complex (6.12 g; 43.1 mmol) were added dropwise. After 3 hours of stirring at −70° C. or less, a saturated aqueous solution of ammonium chloride was added to give two layers. The aqueous layer was extracted with toluene (50 ml) three times. The combined organic layers were washed with water, and dried over anhydrous magnesium sulfate. The solvent was distilled off under reduced pressure. The residue was purified by silica gel column chromatography (silica gel: 100 g; eluent heptane/ethyl acetate=80/20 by volume) to give 2-(trans-4-(4-ethoxy-2,3-difluorophenyl)cyclohexyl)-5-hydroxy-5-(trans-4-pentylcyclohexyl)pentanoic acid t-butyl ester (13) (15.4 g; 63% yield).

Third Step:

Trifluoroacetic acid (TFA; 13.2 ml; 135.5 mmol) was added dropwise to a dichloromethane (100 ml) solution of 2-(trans-4-(4-ethoxy-2,3-difluorophenyl)cyclohexyl)-5-hydroxy-5-(trans-4-pentylcyclohexyl)pentanoic acid t-butyl ester (13) (15.4 g; 27.1 mmol) obtained in the second step with ice-cooling, and the mixture was reacted at room temperature for 5 hours. The reaction mixture was poured into 100 ml to give two layers. The resulting organic layer was washed with water, and dried over anhydrous magnesium sulfate. The solvent was distilled off under reduced pressure. The residue was purified by silica gel column chromatography (silica gel: 100 g; eluent heptane/ethyl acetate=90/10 by volume) to give 3-(trans-4-(4-ethoxy-2,3-difluorophenyl)cyclohexyl)-6-(trans-4-pentylcyclohexyl)tetrahydro-2H-pyran-2-one (14) (12.1 g; 91% yield).

Fourth Step:

Diisobutylaluminum hydride (0.99M in toluene solution; 69 ml; 68.2 mmol) was added dropwise to a tetrahydrofuran (200 ml) solution of 3-(trans-4-(4-ethoxy-2,3-difluorophenyl)cyclohexyl)-6-(trans-4-pentylcyclohexyl)tetrahydro-2H-pyran-2-one (14) (15.2 g; 31.0 mmol) obtained in the third step in a reaction vessel at −50° C. or less under an atmosphere of nitrogen, and the mixture was reacted for 3 hours. The reaction mixture was poured into a 10% aqueous solution of formic acid (200 ml) to give two layers. The aqueous layer was extracted with toluene (100 ml) twice. The combined organic layers were washed with water, and dried over anhydrous magnesium sulfate. The solvent was distilled off under reduced pressure to give 3-(trans-4-(4-ethoxy-2,3-difluorophenyl)cyclohexyl)-6-(trans-4-pentylcyclohexyl)tetrahydro-2H-pyran-2-ol (15) (15.2 g; 99% yield).

Fifth Step:

Triethylsilane (7.17 g; 61.8 mmol) and a boron trifluoride-ethyl ether complex (8.78 g; 61.8 mmol) were added dropwise at −30° C. to a dichloromethane (100 ml) solution of 3-(trans-4-(4-ethoxy-2,3-difluorophenyl)cyclohexyl)-6-(trans-4-pentylcyclohexyl)tetrahydro-2H-pyran-2-ol (15) (15.2 g; 30.9 mmol) obtained in the fourth step. The reaction mixture was returned to room temperature, and it was reacted for 3 hours. Water (100 ml) was added to the reaction mixture to give two layers. The organic layer was washed with water, and dried over anhydrous magnesium sulfate. The solvent was distilled off under reduced pressure. The residue was purified by silica gel column chromatography (silica gel: 200 g; eluent: heptane/ethyl acetate=80/20 by volume) and then by recrystallization (heptane/ethyl acetate=90/10 by volume) to give trans-5-(trans-4-(4-ethoxy-2,3-difluorophenyl)cyclohexyl)-2-(trans-4-pentylcyclohexyl)tetrahydro-2H-pyran (16) (the compound No. 41; 4.6 g; 31% yield).

The chemical shift (δ, ppm) in $^1$H-NMR analysis was described below, and the resulting compound was identified as trans-5-(trans-4-(4-ethoxy-2,3-difluorophenyl)cyclohexyl)-2-(trans-4-pentylcyclohexyl)tetrahydro-2H-pyran (16). The solvent for measurement was CDCl$_3$.

Chemical shift (δ ppm): 6.81 (dt, 1H), 6.56 (dt, 1H), 4.16-4.02 (m, 3H), 3.13 (t, 1H), 2.91 (qd, 1H), 2.72 (tt, 1H), 1.97-1.64 (m, 10H) and 1.50-0.79 (m, 28H)

The phase transition temperature of the resulting compound (16), that is to say, the compound No. 41 was as follows.

Transition temperature: C 82.2 SB 257.2 N 298.1 Iso.

Example 3

Preparation of trans-5-(trans-4'-(4-ethoxy-2,3-difluorophenyl)bi(cyclohexane)-trans-4-yl)-2-pentyltetrahydro-2H-pyran (No. 109)

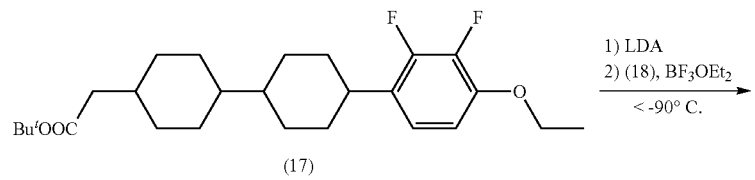

(17)

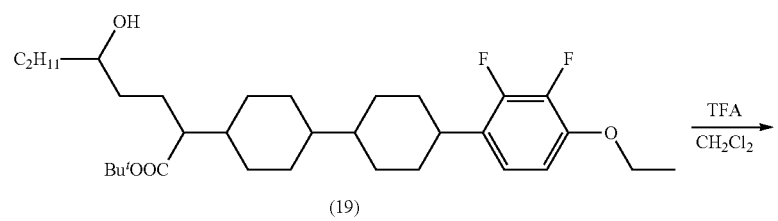

(19)

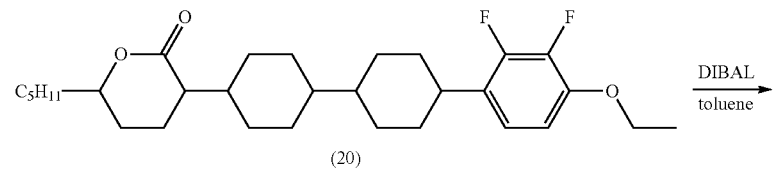

(20)

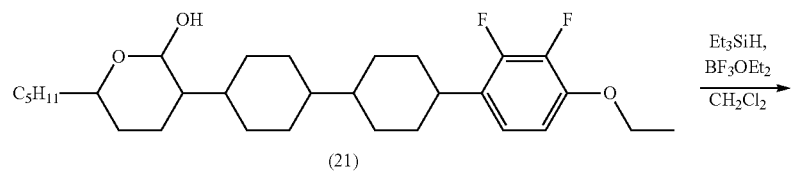

(21)

-continued

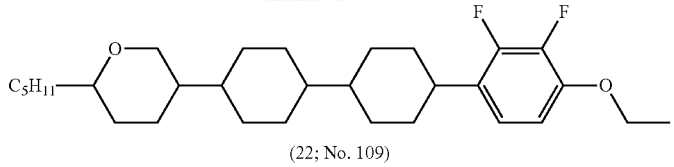

(22; No. 109)

First Step:

Lithium diisopropylamide (1.98M in tetrahydrofuran solution; LDA; 35 ml; 69.7 mmol) was added dropwise at −60° C. to a tetrahydrofuran (200 ml) solution of 2-(trans-4'-(4-ethoxy-2,3-difluorophenyl)bi(cyclohexane)-trans-4-yl)acetic acid t-butyl ester (17) (15.2 g; 34.9 mmol) prepared in a method similar to that in the compound (11), and the mixture was reacted at the same temperature for 1 hour. The reaction mixture was cooled to −90° C. or less, and a tetrahydrofuran (5 ml) solution of 2-pentyloxetane (18) (3.72 g; 29.1 mmol) prepared by the generally known method and a boron trifluoride-ethyl ether complex (2.37 g) were added dropwise. After 3 hours of stirring at temperatures of −70° C. or less, a saturated aqueous solution of ammonium chloride was added to give two layers. The aqueous layer was extracted with toluene (100 ml) three times. The combined organic layers were washed with water, and dried over anhydrous magnesium sulfate. The solvent was distilled off under reduced pressure. The residue was purified by silica gel column chromatography (silica gel: 200 g; eluent: heptane/ethyl acetate=80/20 by volume) to give 2-(trans-4'-(4-ethoxy-2,3-difluorophenyl)bi(cyclohexane)-trans-4-yl)-5-hydroxydecanoic acid t-butyl ester (19) (10.8 g; 66% yield).

Second Step:

Trifluoroacetic acid (TFA; 7.4 ml; 96.6 mmol) was added dropwise to a dichloromethane (100 ml) solution of 2-(trans-4'-(4-ethoxy-2,3-difluorophenyl)bi(cyclohexane)-trans-4-yl)-5-hydroxydecanoic acid t-butyl ester (19) (10.8 g; 19.1 mmol) obtained in the first step with ice-cooling, and the mixture was reacted at room temperature for 5 hours. The reaction mixture was poured into water (100 ml) to give two layers. The resulting organic layer was washed with water, and dried over anhydrous magnesium sulfate. The solvent was distilled off under reduced pressure. The residue was purified by silica gel column chromatography (silica gel: 100 g; eluent heptane/ethyl acetate=80/20 by volume) to give 3-(trans-4'-(4-ethoxy-2,3-difluorophenyl)cyclohexyl)-6-(trans-4-pentylcyclohexyl)tetrahydro-2H-pyran-2-one (20) (8.0 g; 85% yield).

Third Step:

A toluene solution of diisobutylaluminum hydride (0.99M; 36 ml; 35.6 mmol) was added dropwise to a tetrahydrofuran (100 ml) solution of 3-(trans-4'-(4-ethoxy-2,3-difluorophenyl)cyclohexyl)-6-(trans-4-pentylcyclohexyl)tetrahydro-2H-pyran-2-one (20) (8.0 g; 16.3 mmol) obtained in the second step in a reaction vessel at temperatures of −50° C. or less under an atmosphere of nitrogen, and the mixture was reacted for 3 hours. The reaction mixture was poured into a 10% aqueous solution of formic acid (50 ml) to give two layers. The aqueous layer was extracted with toluene (20 ml) twice. The combined organic layers were washed with water, and dried over anhydrous magnesium sulfate. The solvent was distilled off under reduced pressure to give 3-(trans-4'-(4-ethoxy-2,3-difluorophenyl)bi(cyclohexane)-trans-4-yl)-6-pentyltetrahydro-2H-pyran-2-ol (21) (6.9 g; 86% yield).

Fourth Step:

Triethylsilane (3.25 g; 28.0 mmol) and a boron trifluoride-ethyl ether complex (3.98 g; 28.0 mmol) were added dropwise at −30° C. to a dichloromethane (50 ml) solution of 3-(trans-4-(4-ethoxy-2,3-difluorophenyl)cyclohexyl)-6-(trans-4-pentylcyclohexyl)tetrahydro-2H-pyran-2-ol (21) (6.9 g; 14.0 mmol) obtained in the third step. The reaction mixture was returned to room temperature, and the stirring was continued for another 3 hours. Water (50 ml) was added to the reaction mixture to give two layers. The organic layer was washed with water, and dried over anhydrous magnesium sulfate. The solvent was distilled off under reduced pressure. The residue was purified by silica gel column chromatography (silica gel: 100 g; eluent heptane/ethyl acetate=80/20 by volume) and then by recrystallization (heptane/ethyl acetate=90/10 by volume) to give trans-5-(trans-4'-(4-ethoxy-2,3-difluorophenyl)bi(cyclohexane)-trans-4-yl)-2-pentyltetrahydro-2H-pyran (22) (the compound No. 109; 1.2 g; 18% yield).

The chemical shift (δ, ppm) in $^1$H-NMR analysis was described below, and the resulting compound was identified as trans-5-(trans-4'-(4-ethoxy-2,3-difluorophenyl)bi(cyclohexane)-trans-4-yl)-2-pentyltetrahydro-2H-pyran (22). The solvent for measurement was $CDCl_3$.

Chemical shift (δ ppm): 6.83 (dt, 1H), 6.66 (dt, 1H), 4.12-4.05 (q, 2H), 4.01 (dq, 1H), 3.20-3.08 (m, 2H), 2.71 (tt, 1H) and 1.91-0.84 (m, 38H)

The phase transition temperature of the resulting compound (22), that is to say, the compound No. 109 was as follows.

Transition temperature: C 70.7 SB 265.5 N 309 Iso.

Example 4

Preparation of trans-5-(trans-4-(4-ethoxy-2,3-difluorophenyl)cyclohexyl)-2-(trans-4-propylcyclohexyl)tetrahydro-2H-pyran (No. 44)

trans-5-(trans-4-(4-ethoxy-2,3-difluorophenyl)cyclohexyl)-2-(trans-4-propylcyclohexyl)tetrahydro-2H-pyran was prepared by a method similar to that described in Example 2, using 2-(trans-4-propylcyclohexyl)oxetane instead of 2-(trans-4-pentylcyclohexyl)oxetane in the second step of Example 2.

The chemical shift (δ, ppm) in $^1$H-NMR analysis was described below, and the resulting compound was identified as trans-5-(trans-4-(4-ethoxy-2,3-difluorophenyl)cyclohexyl)-2-(trans-4-propylcyclohexyl)tetrahydro-2H-pyran. The solvent for measurement was $CDCl_3$.

Chemical shift (δ ppm): 6.81 (dt, 1H), 6.66 (dt, 1H), 4.08 (q, 2H), 4.07-4.03 (m, 1H), 3.13 (t, 1H), 2.93-2.89 (m, 1H), 2.75-2.70 (m, 1H), 1.94-1.67 (m, 10H), 1.43 (t, 3H), 1.42-1.09 (m, 13H), 1.05-0.80 (m, 5H) and 0.87 (t, 3H).

The phase transition temperature of the resulting compound (the compound No. 44) was as follows.
Transition temperature: C 82.3 SB 233.2 N 299.8 Iso.

Example 5

Preparation of trans-5-(4'-ethoxy-2',3'-difluorobiphenyl-4-yl)-2-(trans-4-propylcyclohexyl)tetrahydro-2H-pyran (No. 40)

trans-5-(4'-Ethoxy-2',3'-difluorobiphenyl-4-yl)-2-(trans-4-propylcyclohexyl)tetrahydro-2H-pyran was prepared by a method similar to that described in Example 2, using 2-(4'-ethoxy-2',3'-difluorobiphenyl-4-yl)acetic acid t-butyl ester instead of 2-(trans-4-(4-ethoxy-2,3-difluorophenyl)cyclohexyl)acetic acid t-butyl ester in the second step of Example 2.

The chemical shift (δ, ppm) in $^1$H-NMR analysis was described below, and the resulting compound was identified as trans-5-(4'-ethoxy-2',3'-difluorobiphenyl-4-yl)-2-(trans-4-propylcyclohexyl)tetrahydro-2H-pyran. The solvent for measurement was $CDCl_3$.

Chemical shift (δ ppm): 7.43 (d, 2H), 7.29 (d, 2H), 7.07 (td, 1H), 6.79 (td, 1H), 4.15 (q, 2H), 4.06 (dq, 2H), 3.42 (t, 1H), 3.10 (dq, 1H), 2.84 (t, 1H), 2.09 (d, 1H), 1.97 (d, 1H), 1.81-1.72 (m, 5H), 1.57-1.45 (m, 1H), 1.47 (t, 3H), 1.35-1.29 (m, 3H), 1.22-1.11 (m, 3H), 1.05 (sex, 1H) 0.95-0.81 (m, 2H) and 0.87 (t, 3H).

The phase transition temperature of the resulting compound (the compound No. 40) was as follows.
Transition temperature: C 70.3 SB 158.8 SA 184.0 N 293.1 Iso.

Example 6

Preparation of trans-5-(trans-4'-(4-ethoxy-2,3-difluorophenyl)bi(cyclohexane)-trans-4-yl)-2-propyltetrahydro-2H-pyran (No. 108)

trans-5-(trans-4'-(4-Ethoxy-2,3-difluorophenyl)bi(cyclohexane)-trans-4-yl)-2-propyltetrahydro-2H-pyran was prepared by a method similar to that described in Example 3, using 2-propyloxetane instead of 2-pentyloxetane in the first step of Example 3.

The chemical shift (δ, ppm) in $^1$H-NMR analysis was described below, and the resulting compound was identified as trans-5-(trans-4'-(4-ethoxy-2,3-difluorophenyl)bi(cyclohexane)-trans-4-yl)-2-propyltetrahydro-2H-pyran. The solvent for measurement was $CDCl_3$.

Chemical shift (δ ppm): 6.82 (dt, 1H), 6.66 (dt, 1H), 4.08 (q, 2H), 4.03-3.99 (m, 1H), 3.17-3.10 (m, 1H), 3.12 (t, 1H), 2.74-2.69 (m, 1H), 1.89-1.63 (m, 10H), 1.51-1.30 (m, 7H), 1.43 (t, 3H), 1.27-0.92 (m, 11H) and 0.91 (t, 3H).

The phase transition temperature of the resulting compound (the compound No. 108) was as follows.
Transition temperature: C 99.0 SB 234.0 N 313.5 Iso.

Example 7

Preparation of trans-2-(trans-4-(4-ethoxy-2,3-difluorophenyl)cyclohexyl)-5-(4-pentylcyclohexyl)tetrahydro-2H-pyran (No. 75)

trans-2-(trans-4-(4-Ethoxy-2,3-difluorophenyl)cyclohexyl)-5-(4-pentylcyclohexyl)tetrahydro-2H-pyran was prepared was prepared by a method similar to that described in Example 2, using 2-(4-pentylcyclohexyl)acetic acid instead of 2-(trans-4-(4-ethoxy-2,3-difluorophenyl)cyclohexyl)acetic acid in the first step of Example 2, and using 2-(4-(4-ethoxy-2,3-difluorophenyl)cyclohexyl)oxetane instead of 2-(trans-4-pentylcyclohexyl)oxetane in the second step.

The chemical shift (δ, ppm) in $^1$H-NMR analysis was described below, and the resulting compound was identified as trans-2-(trans-4-(4-ethoxy-2,3-difluorophenyl)cyclohexyl)-5-(4-pentylcyclohexyl)tetrahydro-2H-pyran. The solvent for measurement was $CDCl_3$.

Chemical shift (δ ppm): 6.83 (t, 1H), 6.66 (t, 1H), 4.08 (q, 2H), 4.01-4.06 (m, 1H), 3.12 (t, 1H), 2.92-2.98 (m, 1H), 2.12-2.09 (m, 1H), 1.65-1.94 (m, 10H), 1.43 (t, 3H), 1.08-1.48 (m, 17H), 0.78-1.02 (m, 5H) and 0.88 (t, 3H).

The phase transition temperature of the resulting compound (the compound No. 75) was as follows.
Transition temperature: C 70.7 SB 261.5 N 301.4 Iso.

Example 8

Preparation of trans-2-(trans-4'-(4-ethoxy-2,3-difluorophenyl)-[1,1'-bi(cyclohexane)]-4-yl)-5-pentyltetrahydro-2H-pyran (No. 143)

trans-2-(trans-4'-(4-Ethoxy-2,3-difluorophenyl)-[1,1'-bi(cyclohexane)]-4-yl)-5-pentyltetrahydro-2H-pyran was prepared by a method similar to that described in Example 2, using enanthic acid instead of 2-(trans-4-(4-ethoxy-2,3-difluorophenyl)cyclohexyl)acetic acid in the first step of Example 2, and using 2-(4'-(4-ethoxy-2,3-difluorophenyl)-[1,1'-bi(cyclohexane)]-4-yl)oxetane instead of 2-(trans-4-pentylcyclohexyl)oxetane in the second step.

The chemical shift (δ, ppm) in $^1$H-NMR analysis was described below, and the resulting compound was identified as trans-2-(trans-4'-(4-ethoxy-2,3-difluorophenyl)-[1,1'-bi(cyclohexane)]-4-yl)-5-pentyltetrahydro-2H-pyran. The solvent for measurement was $CDCl_3$.

Chemical shift (δ ppm): 6.83 (t, 1H), 6.66 (t, 1H), 4.08 (q, 2H), 3.90-3.96 (m, 1H), 2.98 (t, 1H), 2.88-2.95 (m, 1H), 2.68-2.76 (m, 1H), 1.61-2.02 (m, 9H), 0.90-1.55 (m, 23H), 1.43 (t, 3H) and 0.88 (t, 3H).

The phase transition temperature of the resulting compound (the compound No. 75) was as follows.
Transition temperature: C 72.0 SB 290.5 N 313.6 Iso.

Example 9

Preparation of trans-2-(4'-ethoxy-2',3'-difluoro-[1,1'-biphenyl]-4-yl)-5-(4-propylcyclohexyl)tetrahydro-2H-pyran (No. 313)

trans-2-(4'-Ethoxy-2',3'-difluoro-[1,1'-biphenyl]-4-yl)-5-(4-propylcyclohexyl)tetrahydro-2H-pyran was prepared by a method similar to that described in Example 2, using 2-(4-pentylcyclohexyl)acetic acid instead of 2-(trans-4-(4-ethoxy-2,3-difluorophenyl)cyclohexyl)acetic acid in the first step of Example 2, and using 2-(4'-ethoxy-2',3'-difluoro-[1,1'-biphenyl]-4-yl)oxetane instead of 2-(trans-4-pentylcyclohexyl)oxetane in the second step.

The chemical shift (δ, ppm) in $^1$H-NMR analysis was described below, and the resulting compound was identified as trans-2-(4'-ethoxy-2',3'-difluoro-[1,1'-biphenyl]-4-yl)-5-(4-propylcyclohexyl)tetrahydro-2H-pyran. The solvent for measurement was $CDCl_3$.

Chemical shift (δ ppm): 7.467 (m, 2H), 7.408 (m, 2H), 7.077 (m, 1H), 6.781 (m, 1H), 4.295 (m, 1H), 4.192 (m, 1H), 4.170 (q, 2H), 3.346 (t, 1H), 2.050-1.980 (m, 1H), 1.960-1.900 (m, 1H), 1.825-1.710 (m, 4H), 1.665-1.570 (m, 1H), 1.530-1.430 (m, 4H), 1.420-1.265 (m, 3H), 1.230-0.950 (m, 6H) and 0.910-0.800 (m, 5H).

The phase transition temperature of the resulting compound (the compound No. 313) was as follows.
Transition temperature: C 97.8 N 312.1 Iso.

Example as a reference Preparation of trans-2-(4-ethoxy-2,3-difluorophenyl)-5-(4'-pentyl-[1,1'-bi(cyclohexane)]-4-yl)tetrahydro-2H-pyran (the compound (c))

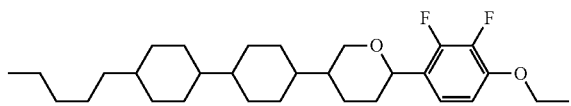 [SMILES: CCCCCC1CCC(C2CCC(C3CCC(c4ccc(OCC)c(F)c4F)OC3)CC2)CC1]

trans-2-(4-Ethoxy-2,3-difluorophenyl)-5-(4'-pentyl-[1,1'-bi(cyclohexane)]-4-yl)tetrahydro-2H-pyran was prepared by a method similar to that described in Example 2, using 2-(trans-4'-pentyl-[1,1'-bi(cyclohexane)]-4-yl)acetic acid instead of 2-(trans-4-(4-ethoxy-2,3-difluorophenyl)cyclohexyl)acetic acid in the first step of Example 2, and using 2-(4-ethoxy-2,3-difluorophenyl)oxetane instead of 2-(trans-4-pentylcyclohexyl)oxetane in the second step.

The chemical shift ($\delta$, ppm) in $^1$H-NMR analysis was described below, and the resulting compound was identified as trans-2-(4-ethoxy-2,3-difluorophenyl)-5-(4'-pentyl-[1,1'-bi(cyclohexane)]-4-yl)tetrahydro-2H-pyran. The solvent for measurement was CDCl$_3$.

Chemical shift ($\delta$ ppm): 7.095 (m, 1H), 6.714 (m, 1H), 4.485 (m, 1H), 4.148 (m, 1H), 4.112 (q, 2H), 3.333 (t, 1H), 2.005-1.840 (m, 2H), 1.830-1.645 (m, 8H) and 1.600-0.770 (m, 29H).

The phase transition temperature of the resulting compound (the compound (c)) was as follows.
Transition temperature: C 99.3 SB 267.1 N 312.9 Iso.

The following compounds can be prepared according to the methods described in Examples 1 to 9.

| No. | |
|---|---|
| 1 | (structure) |
| 2 | (structure) |
| 3 | (structure) |
| 4 | (structure) |
| 5 | (structure) |
| 6 | (structure) |
| 7 | (structure) |

-continued
| No. | |
|---|---|
| 8 | 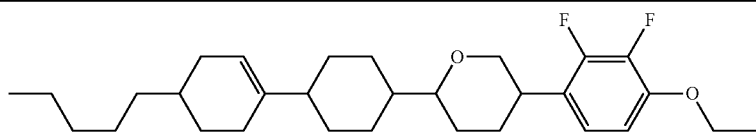 |
| 9 | 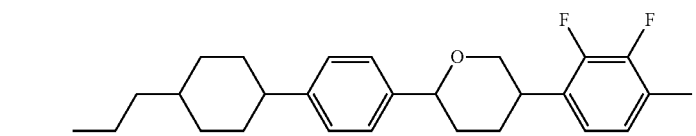 |
| 10 | 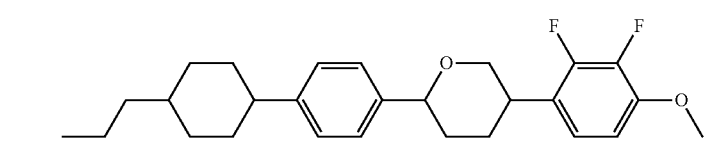 [SMILES: CCCC1CCC(c2ccc(C3CCC(c4ccc(OC)c(F)c4F)CO3)cc2)CC1] |
| 11 | 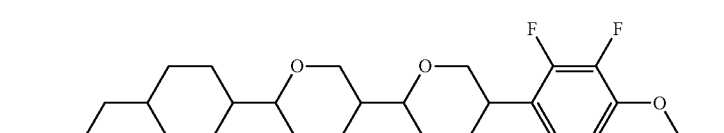 |
| 12 | 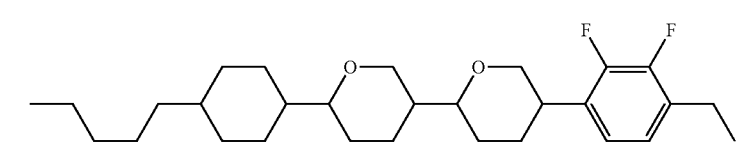 [SMILES: CCCCCC1CCC(C2CCC(C3CCC(c4ccc(CC)c(F)c4F)CO3)CO2)CC1] |
| 13 | 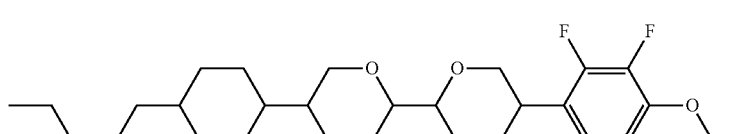 |
| 14 | 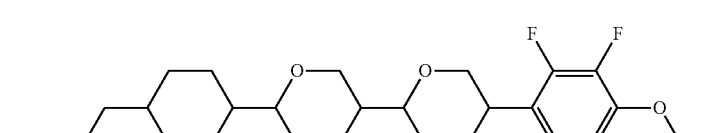 |
| 15 | 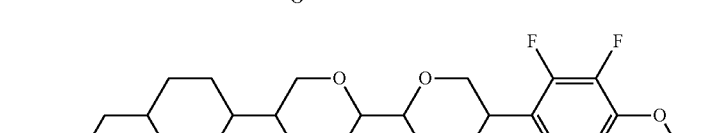 |
| 16 | 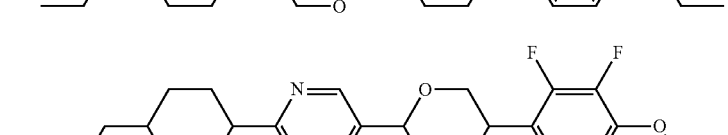 |
| 17 | 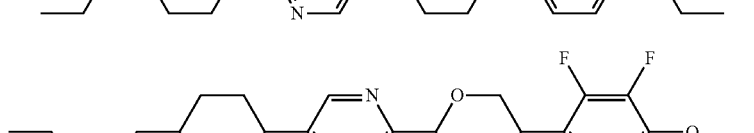 |
| 18 | 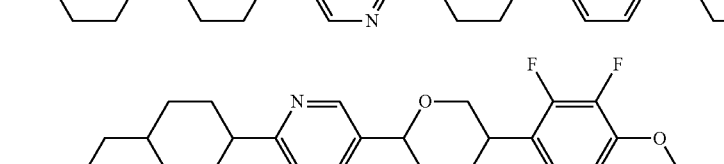 |

-continued
| No. | |
|---|---|
| 19 | 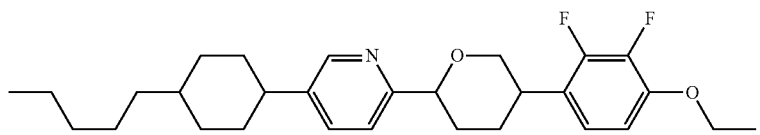 [SMILES: CCCCCC1CCC(c2ccc(C3CCC(c4ccc(OCC)c(F)c4F)CO3)nc2)CC1] |
| 20 | 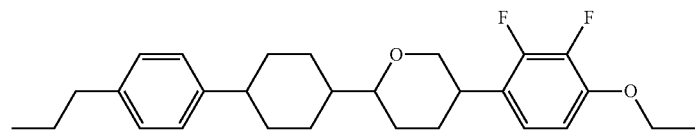 |
| 21 | 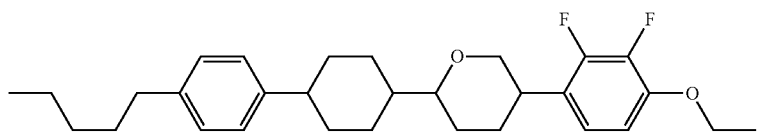 [SMILES: CCCCCc1ccc(C2CCC(C3CCC(c4ccc(OCC)c(F)c4F)CO3)CC2)cc1] |
| 22 | 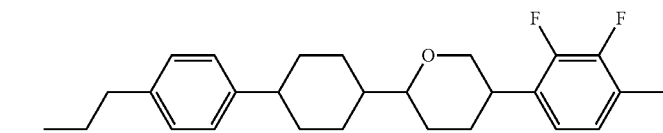 [SMILES: CCCc1ccc(C2CCC(C3CCC(c4ccc(C)c(F)c4F)CO3)CC2)cc1] |
| 23 | 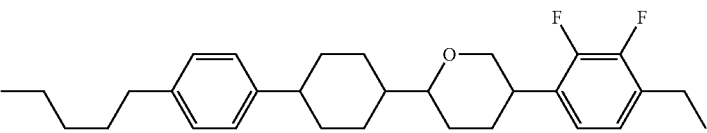 [SMILES: CCCCCc1ccc(C2CCC(C3CCC(c4ccc(CC)c(F)c4F)CO3)CC2)cc1] |
| 24 | 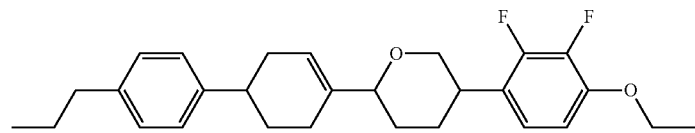 [SMILES: CCCc1ccc(C2CC=C(C3CCC(c4ccc(OCC)c(F)c4F)CO3)CC2)cc1] |
| 25 | 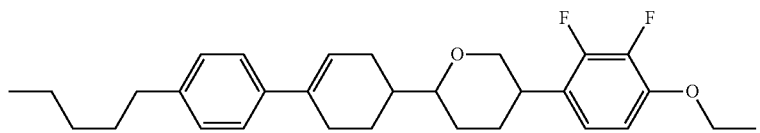 |
| 26 | 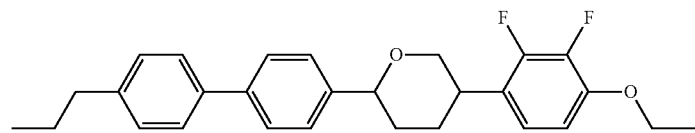 |
| 27 | 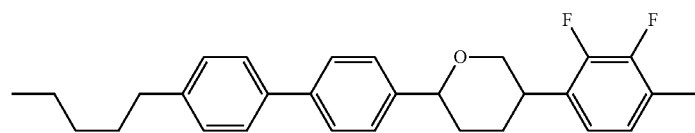 [SMILES: CCCCCc1ccc(-c2ccc(C3CCC(c4ccc(C)c(F)c4F)CO3)cc2)cc1] |
| 28 | 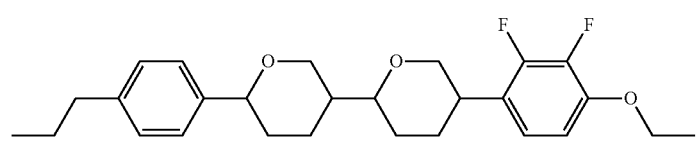 |
| 29 | 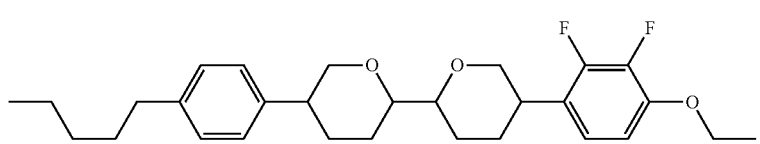 [SMILES: CCCCCc1ccc(C2CCC(C3CCC(c4ccc(OCC)c(F)c4F)CO3)OC2)cc1] |

| No. | |
|---|---|
| 30 | 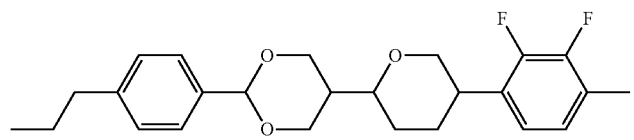 |
| 31 | 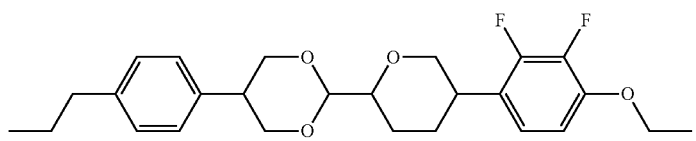 [SMILES: CCCc1ccc(C2COC(C3CCC(c4ccc(OCC)c(F)c4F)CO3)OC2)cc1] |
| 32 | 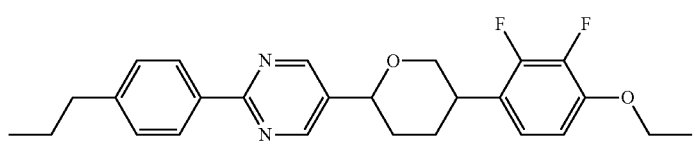 [SMILES: CCCc1ccc(-c2ncc(C3CCC(c4ccc(OCC)c(F)c4F)CO3)cn2)cc1] |
| 33 | 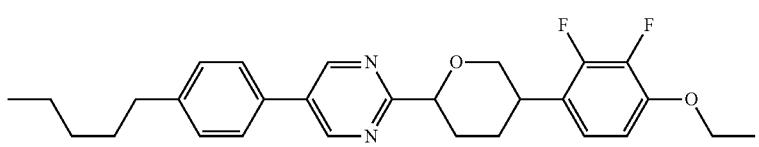 [SMILES: CCCCCc1ccc(-c2cnc(C3CCC(c4ccc(OCC)c(F)c4F)CO3)nc2)cc1] |
| 34 | 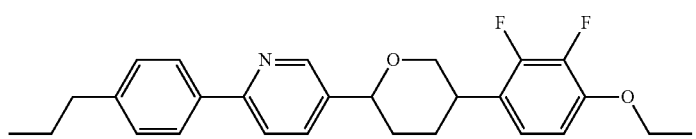 |
| 35 | 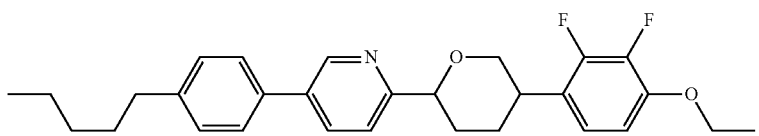 [SMILES: CCCCCc1ccc(-c2ccc(C3CCC(c4ccc(OCC)c(F)c4F)CO3)nc2)cc1] |
| 36 | 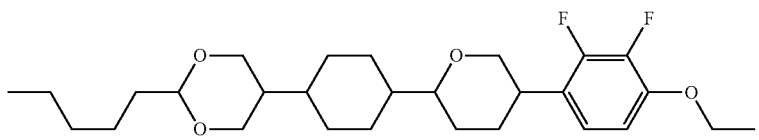 [SMILES: CCCCCC1OCC(C2CCC(C3CCC(c4ccc(OCC)c(F)c4F)CO3)CC2)CO1] |
| 37 | 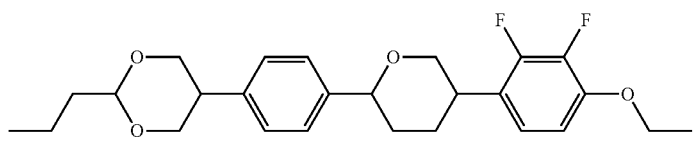 [SMILES: CCCC1OCC(c2ccc(C3CCC(c4ccc(OCC)c(F)c4F)CO3)cc2)CO1] |
| 38 | 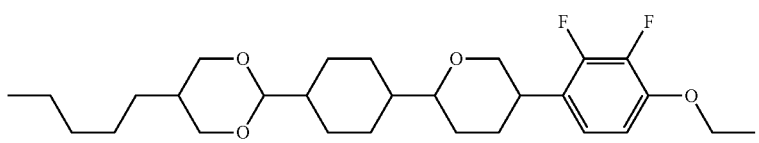 [SMILES: CCCCCC1COC(C2CCC(C3CCC(c4ccc(OCC)c(F)c4F)CO3)CC2)OC1] |
| 39 | 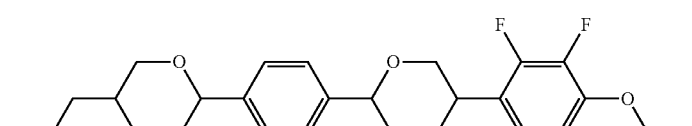 |
| 40 | 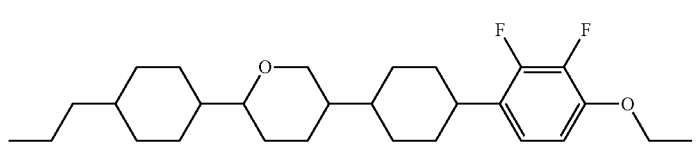 |

-continued
| No. |
|---|
| 41 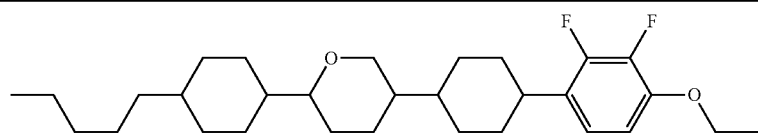 |
| 42 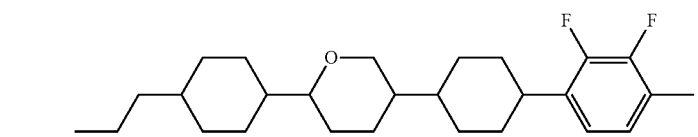 |
| 43 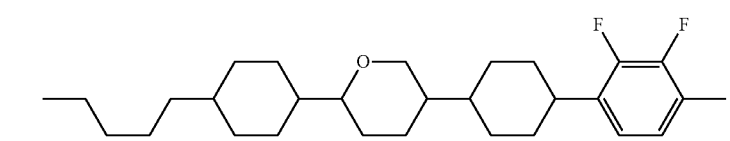 [SMILES: CCCCCC1CCC(C2CCC(C3CCC(c4ccc(C)c(F)c4F)CC3)CO2)CC1] |
| 44 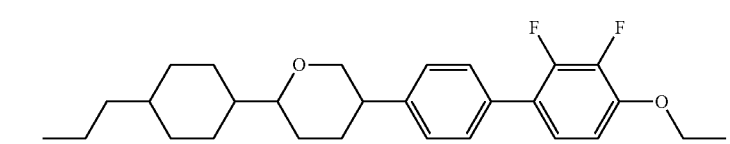 |
| 45 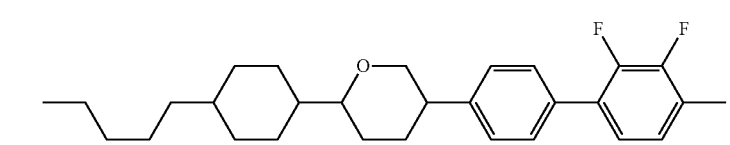 |
| 46 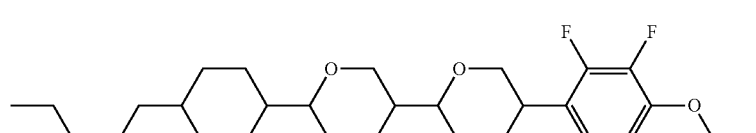 |
| 47 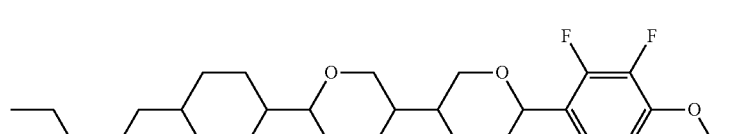 |
| 48 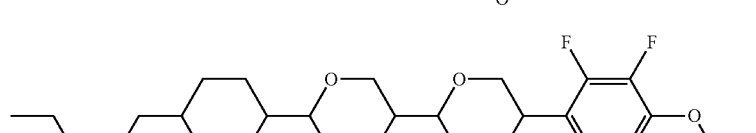 |
| 49 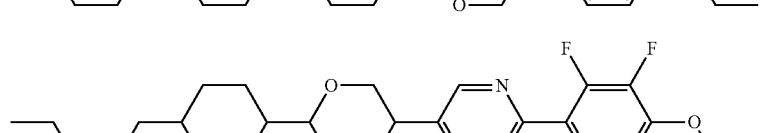 |
| 50 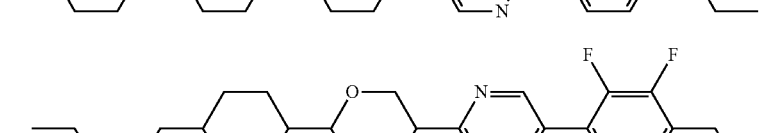 |
| 51 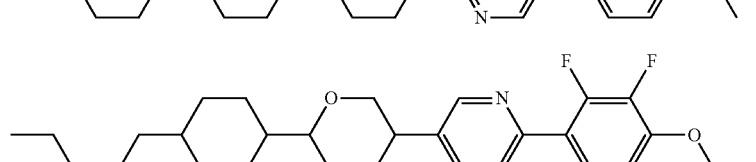 |

-continued
| No. | |
|---|---|
| 52 | 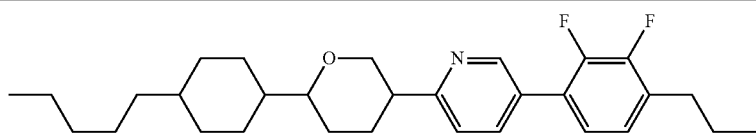 [SMILES: CCCCCC1CCC(C2CCC(c3ccc(-c4ccc(CCC)c(F)c4F)cn3)CO2)CC1] |
| 53 | 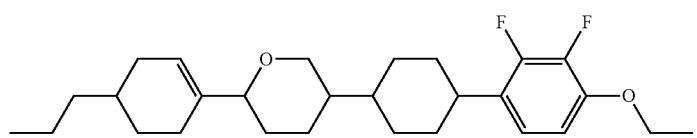 |
| 54 | 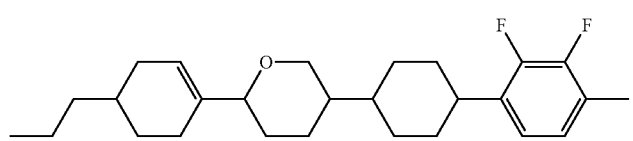 |
| 55 | 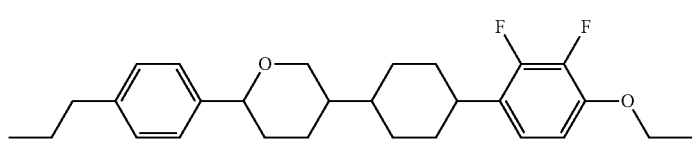 [SMILES: CCCc1ccc(C2CCC(C3CCC(c4ccc(OCC)c(F)c4F)CC3)CO2)cc1] |
| 56 | 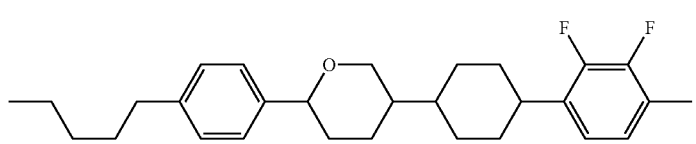 |
| 57 | 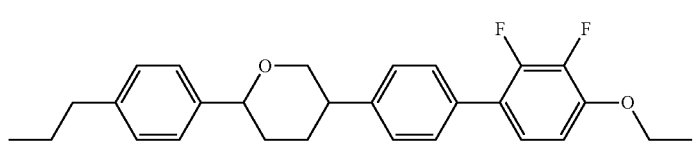 [SMILES: CCCc1ccc(C2CCC(c3ccc(-c4ccc(OCC)c(F)c4F)cc3)CO2)cc1] |
| 58 | 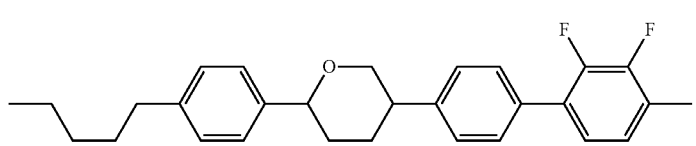 |
| 59 | 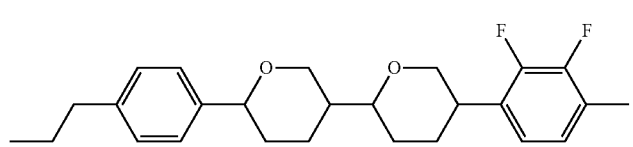 [SMILES: CCCc1ccc(C2CCC(C3CCC(c4ccc(C)c(F)c4F)CO3)CO2)cc1] |
| 60 | 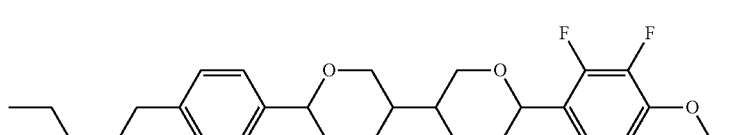 |
| 61 | 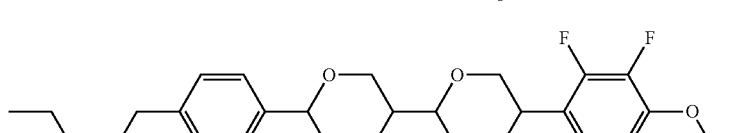 |
| 62 | 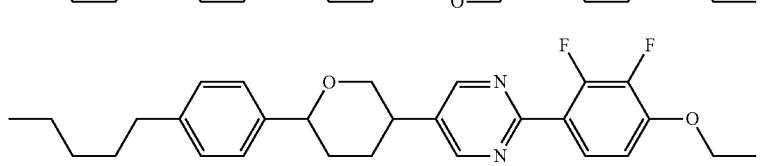 |

-continued
| No. | |
|---|---|
| 63 | 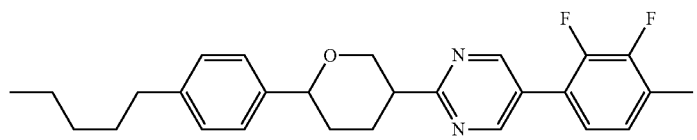 |
| 64 | 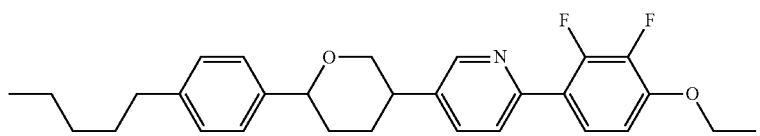 |
| 65 | 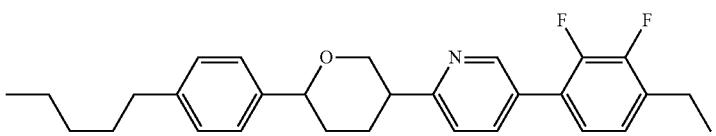 [SMILES: CCCCCc1ccc(C2CCC(c3ccc(-c4ccc(CC)c(F)c4F)cn3)CO2)cc1] |
| 66 | 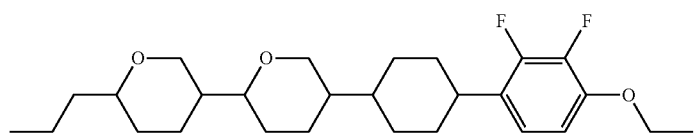 |
| 67 | 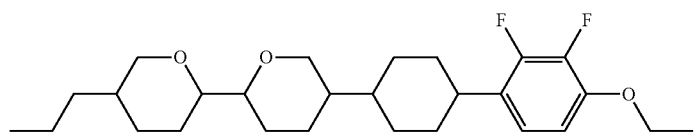 |
| 68 | 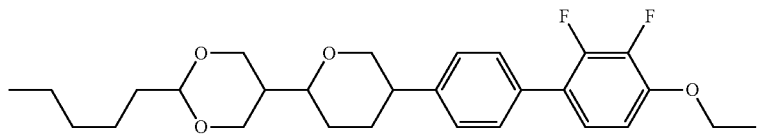 |
| 69 | 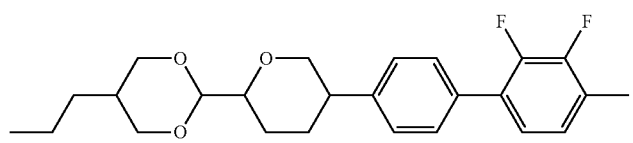 |
| 70 | 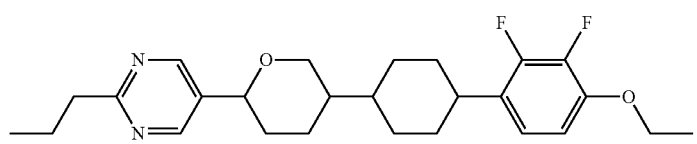 [SMILES: CCCc1ncc(C2CCC(C3CCC(c4ccc(OCC)c(F)c4F)CC3)CO2)cn1] |
| 71 | 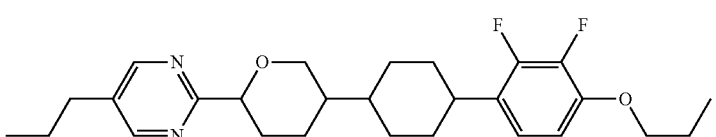 |
| 72 | 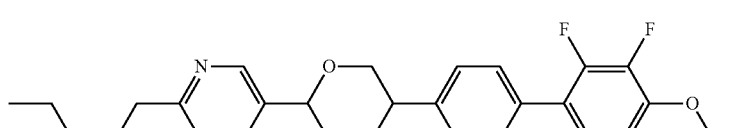 |
| 73 | 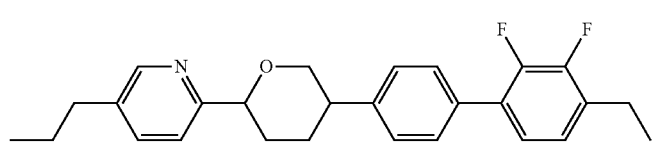 |

-continued
| No. | |
|---|---|
| 74 | 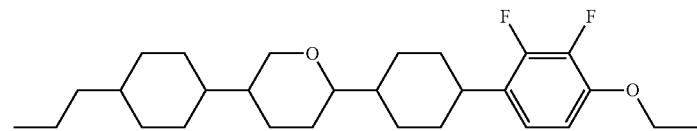 |
| 75 | 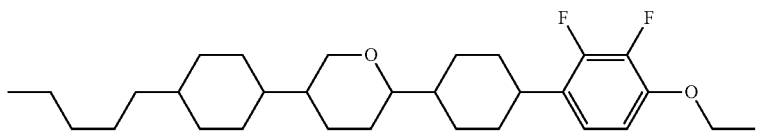 [SMILES: CCCCCC1CCC(C2CCC(C3CCC(c4ccc(OCC)c(F)c4F)CC3)OC2)CC1] |
| 76 | 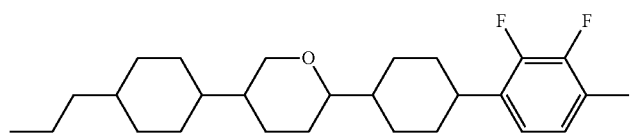 |
| 77 | 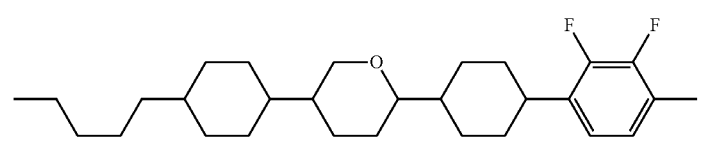 |
| 78 | 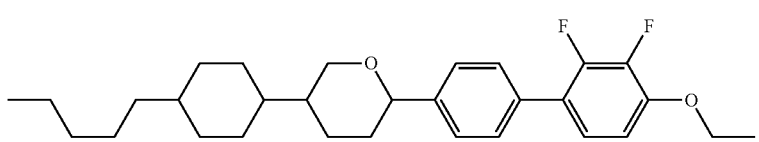 [SMILES: CCCCCC1CCC(C2CCC(c3ccc(-c4ccc(OCC)c(F)c4F)cc3)OC2)CC1] |
| 79 | 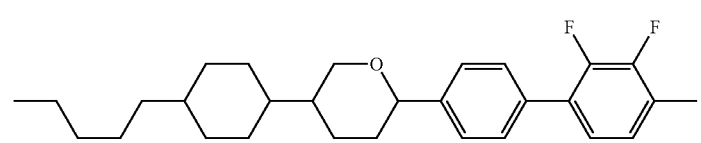 |
| 80 | 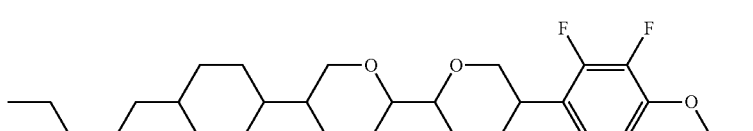 |
| 81 | 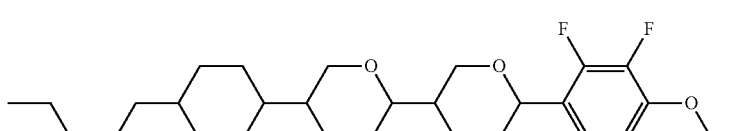 |
| 82 | 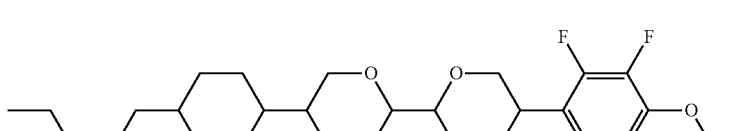 |
| 83 | 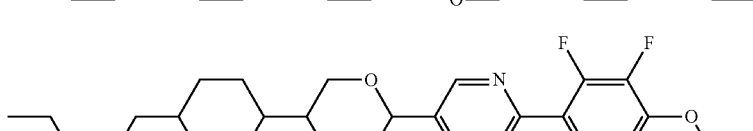 |
| 84 | 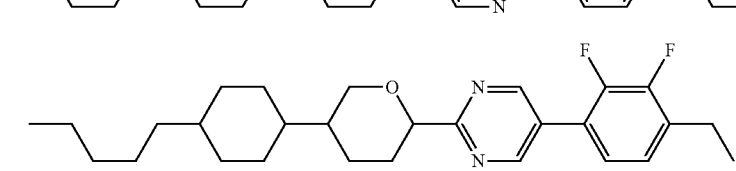 |

-continued
| No. | |
|---|---|
| 85 | 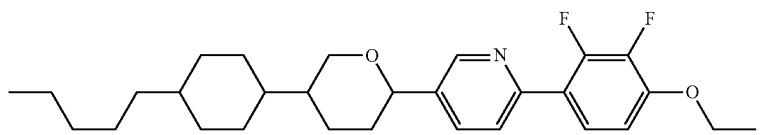 |
| 86 | 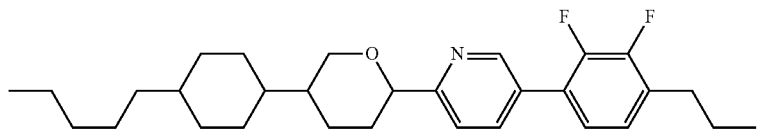 |
| 87 | 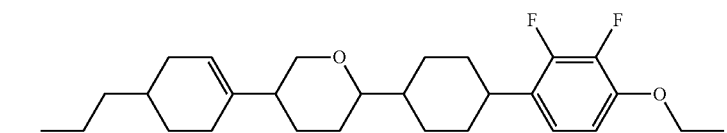 |
| 88 | 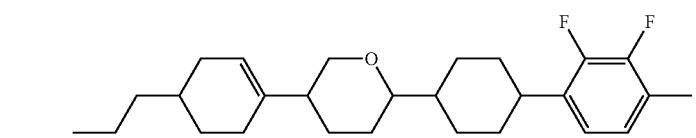 |
| 89 | 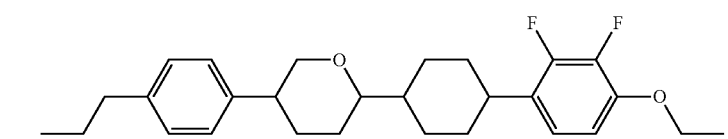 [SMILES: CCCc1ccc(C2CCC(C3CCC(c4ccc(OCC)c(F)c4F)CC3)OC2)cc1] |
| 90 | 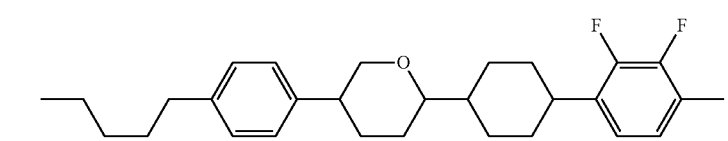 |
| 91 | 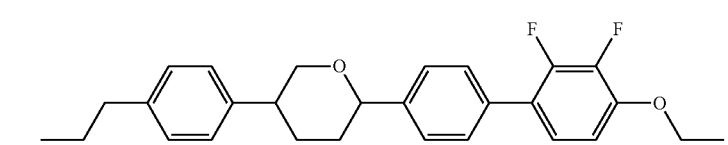 |
| 92 | 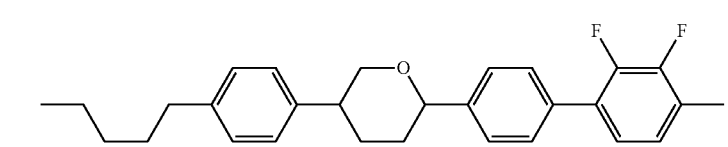 |
| 93 | 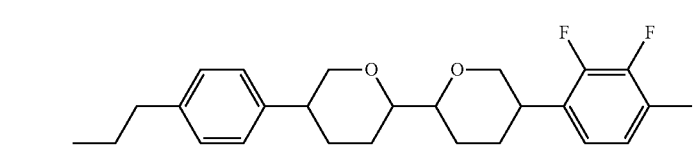 |
| 94 | 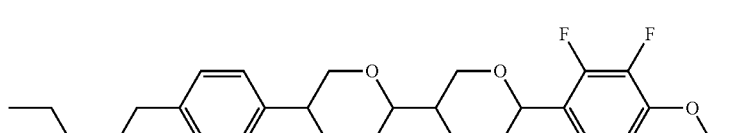 |
| 95 | 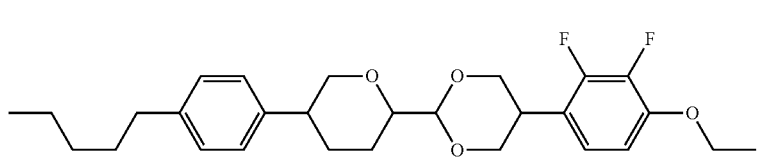 |

-continued
| No. | |
|---|---|
| 96 | 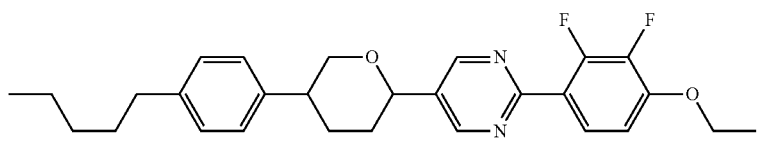 |
| 97 | 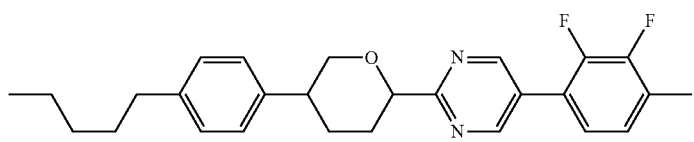 [SMILES: CCCCCc1ccc(C2CCC(c3ncc(-c4ccc(C)c(F)c4F)cn3)OC2)cc1] |
| 98 | 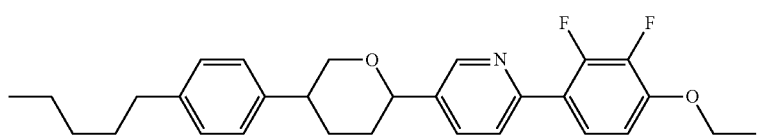 [SMILES: CCCCCc1ccc(C2CCC(c3ccc(-c4ccc(OCC)c(F)c4F)nc3)OC2)cc1] |
| 99 | 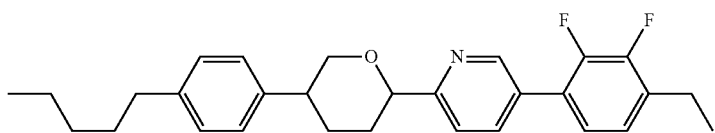 [SMILES: CCCCCc1ccc(C2CCC(c3ccc(-c4ccc(CC)c(F)c4F)cn3)OC2)cc1] |
| 100 | 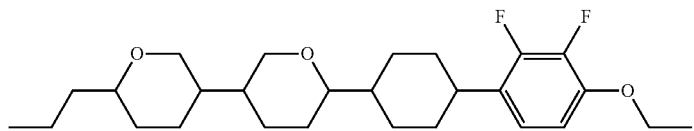 |
| 101 | 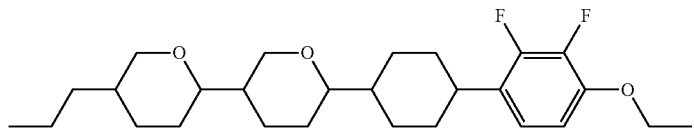 |
| 102 | 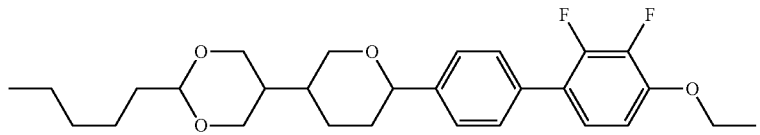 |
| 103 | 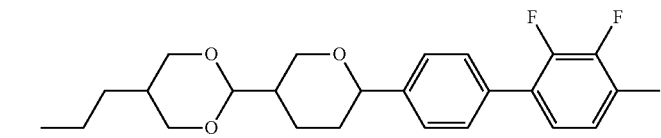 |
| 104 | 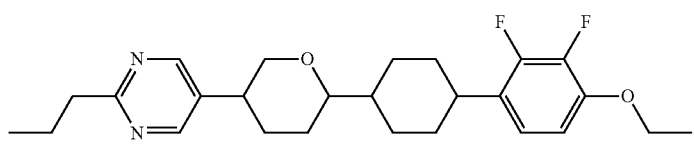 |
| 105 | 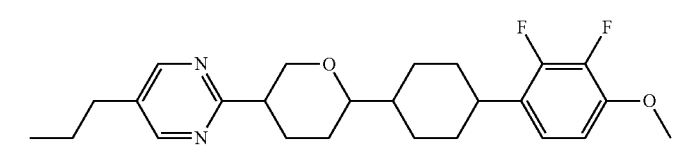 [SMILES: CCCc1cnc(C2CCC(C3CCC(c4ccc(OC)c(F)c4F)CC3)OC2)nc1] |
| 106 | 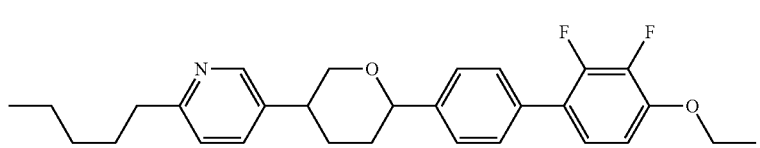 [SMILES: CCCCCc1ccc(C2CCC(c3ccc(-c4ccc(OCC)c(F)c4F)cc3)OC2)cn1] |

-continued
| No. |
|---|
| 107 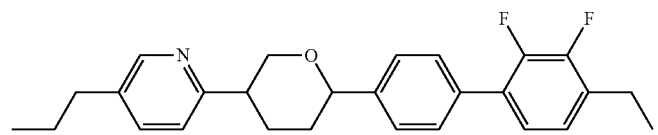 [SMILES: CCCc1ccc(C2CCC(c3ccc(-c4ccc(CC)c(F)c4F)cc3)OC2)nc1] |
| 108 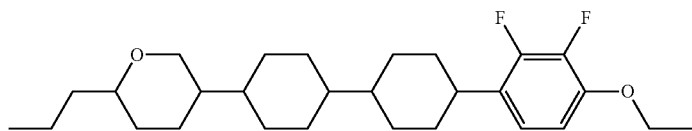 |
| 109 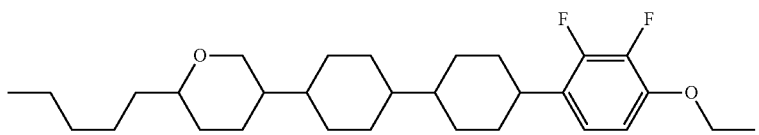 [SMILES: CCCCCC1CCC(C2CCC(C3CCC(c4ccc(OCC)c(F)c4F)CC3)CC2)CO1] |
| 110 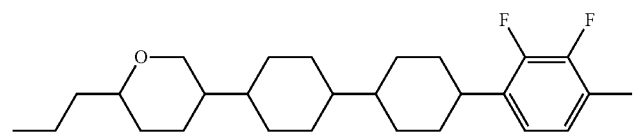 |
| 111 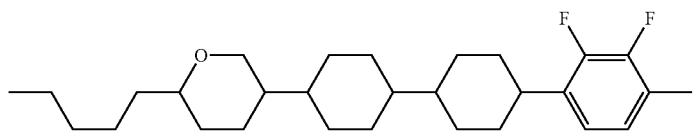 |
| 112 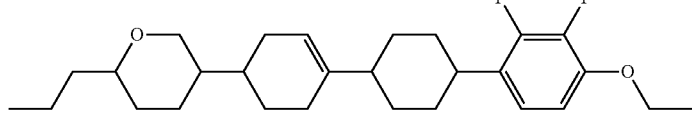 |
| 113 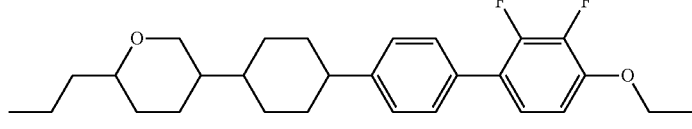 |
| 114 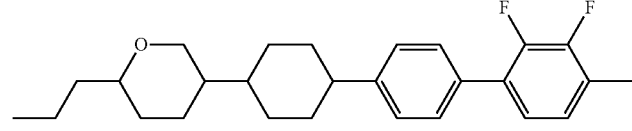 [SMILES: CCCC1CCC(C2CCC(c3ccc(-c4ccc(C)c(F)c4F)cc3)CC2)CO1] |
| 115 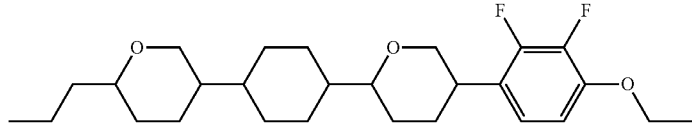 |
| 116 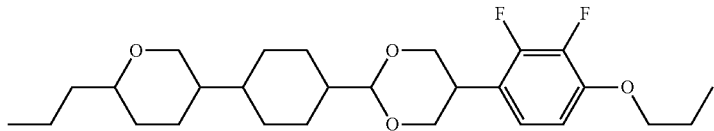 |
| 117 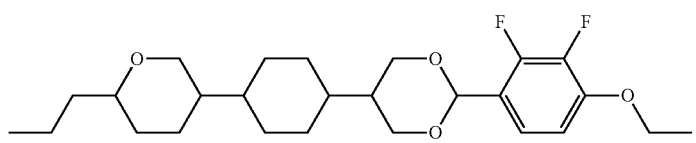 |

-continued
| No. | |
|---|---|
| 118 | 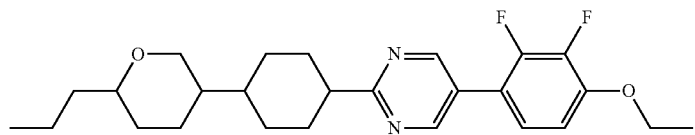 [SMILES: CCCC1CCC(C2CCC(c3ncc(-c4ccc(OCC)c(F)c4F)cn3)CC2)CO1] |
| 119 | 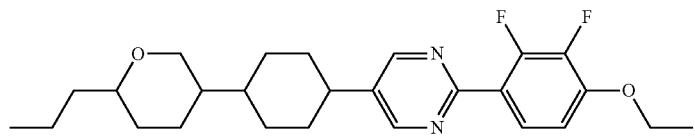 [SMILES: CCCC1CCC(C2CCC(c3cnc(-c4ccc(OCC)c(F)c4F)nc3)CC2)CO1] |
| 120 | 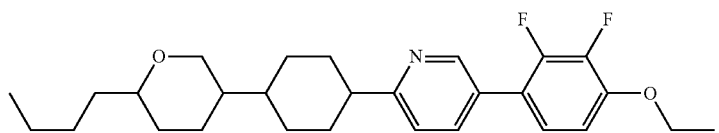 [SMILES: CCCCC1CCC(C2CCC(c3ccc(-c4ccc(OCC)c(F)c4F)cn3)CC2)CO1] |
| 121 | 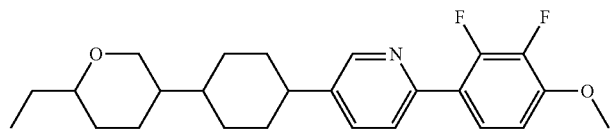 [SMILES: CCC1CCC(C2CCC(c3ccc(-c4ccc(OC)c(F)c4F)nc3)CC2)CO1] |
| 122 | 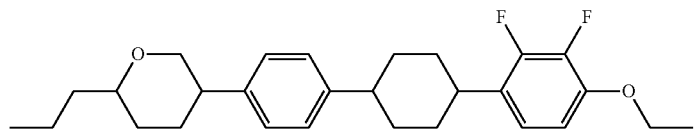 |
| 123 | 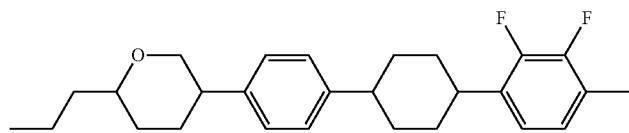 |
| 124 | 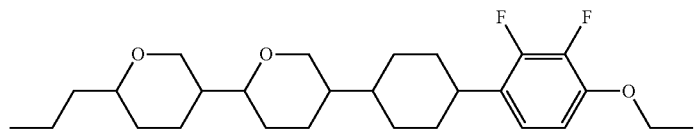 |
| 125 | 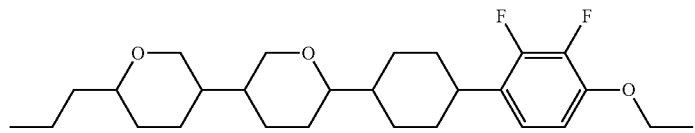 |
| 126 | 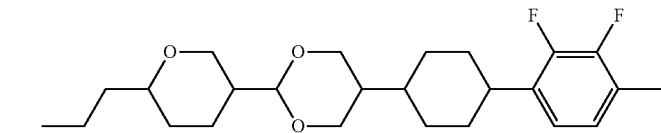 |
| 127 | 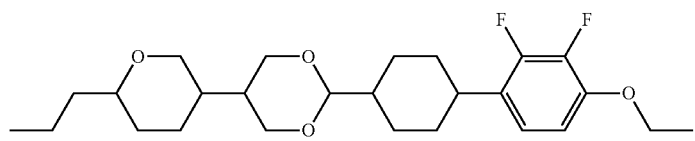 |
| 128 | 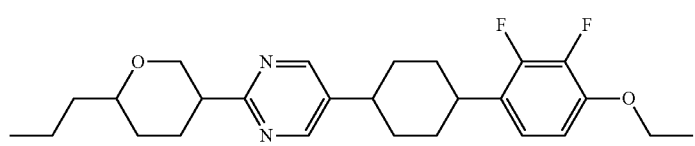 |

| No. | |
|---|---|
| 129 | 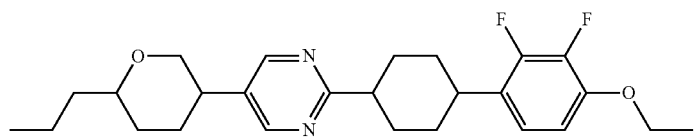 [SMILES: CCCC1CCC(c2cnc(C3CCC(c4ccc(OCC)c(F)c4F)CC3)nc2)CO1] |
| 130 | 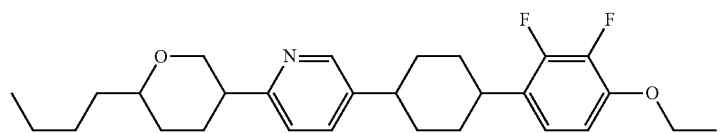 [SMILES: CCCCC1CCC(c2ccc(C3CCC(c4ccc(OCC)c(F)c4F)CC3)cn2)CO1] |
| 131 | 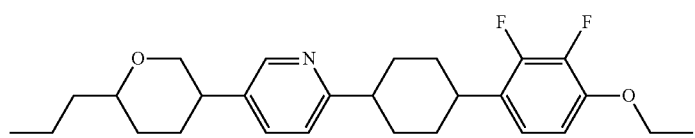 |
| 132 | 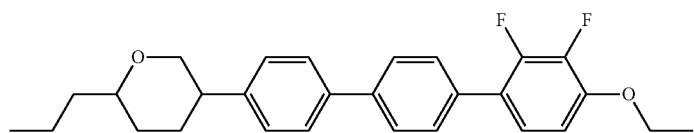 |
| 133 | 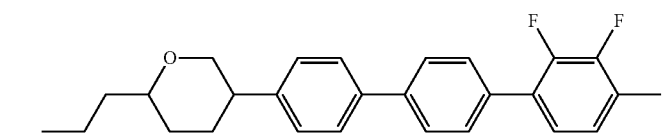 |
| 134 | 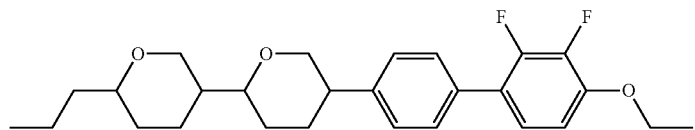 |
| 135 | 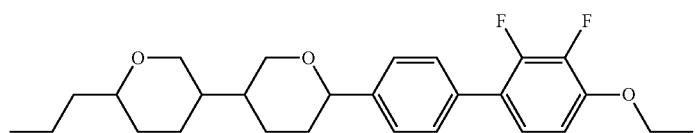 |
| 136 | 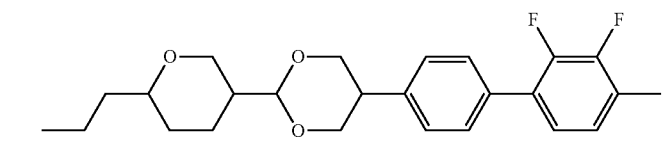 [SMILES: CCCC1CCC(C2OCC(c3ccc(-c4ccc(C)c(F)c4F)cc3)CO2)CO1] |
| 137 | 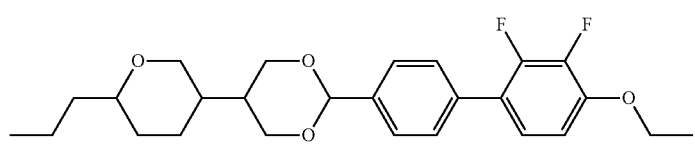 [SMILES: CCCC1CCC(C2COC(c3ccc(-c4ccc(OCC)c(F)c4F)cc3)OC2)CO1] |
| 138 | 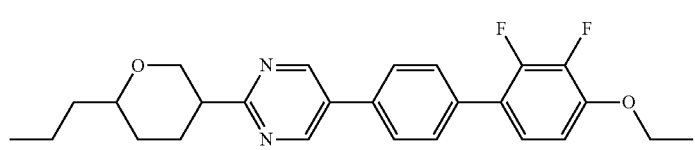 |
| 139 | 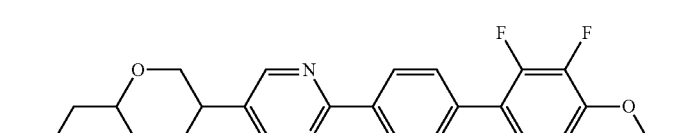 |

| No. | |
|---|---|
| 140 | 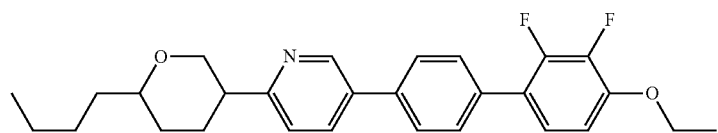 |
| 141 | 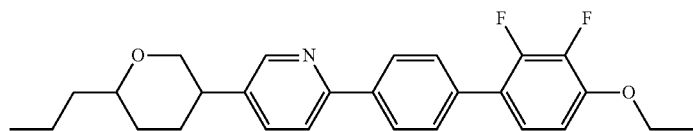 [SMILES: CCCC1CCC(c2ccc(-c3ccc(-c4ccc(OCC)c(F)c4F)cc3)nc2)CO1] |
| 142 | 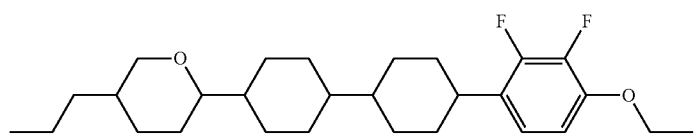 [SMILES: CCCC1CCC(C2CCC(C3CCC(c4ccc(OCC)c(F)c4F)CC3)CC2)OC1] |
| 143 | 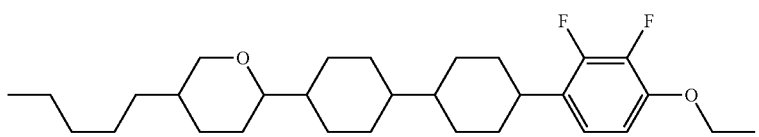 [SMILES: CCCCCC1CCC(C2CCC(C3CCC(c4ccc(OCC)c(F)c4F)CC3)CC2)OC1] |
| 144 | 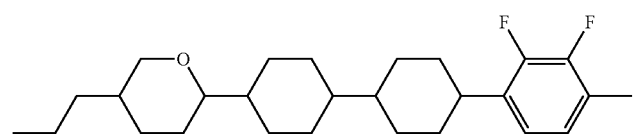 [SMILES: CCCC1CCC(C2CCC(C3CCC(c4ccc(C)c(F)c4F)CC3)CC2)OC1] |
| 145 | 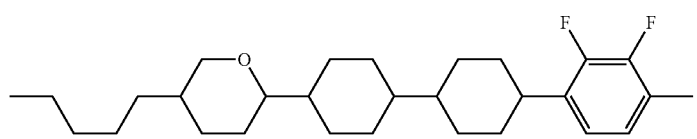 [SMILES: CCCCCC1CCC(C2CCC(C3CCC(c4ccc(C)c(F)c4F)CC3)CC2)OC1] |
| 146 | 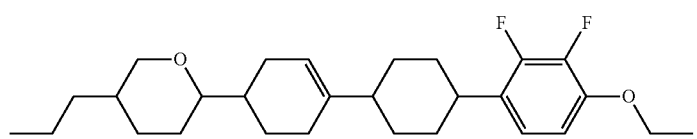 [SMILES: CCCC1CCC(C2CC=C(C3CCC(c4ccc(OCC)c(F)c4F)CC3)CC2)OC1] |
| 147 | 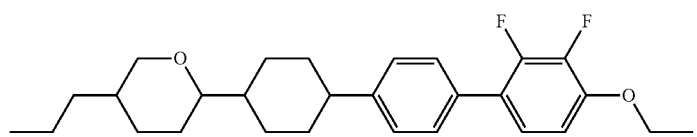 |
| 148 | 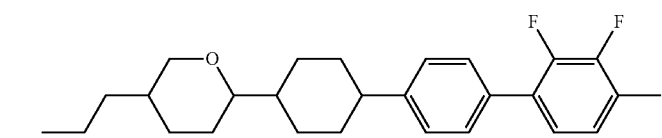 |
| 149 | 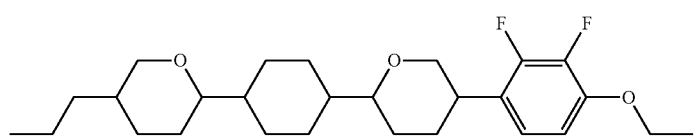 |
| 150 | 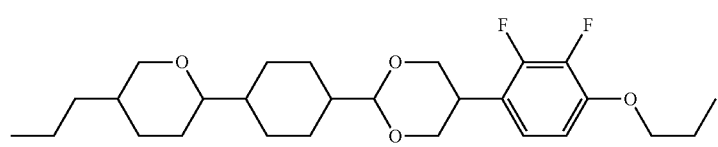 |

| No. |  |
|---|---|
| 151 | 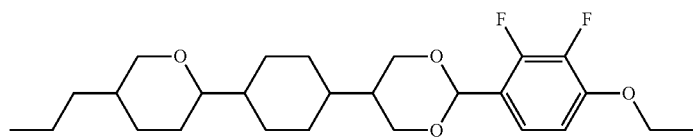 |
| 152 | 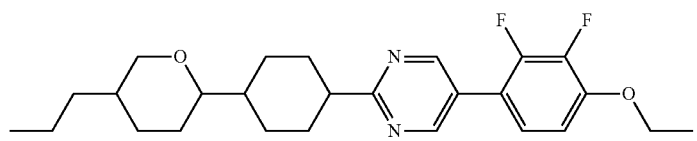 |
| 153 | 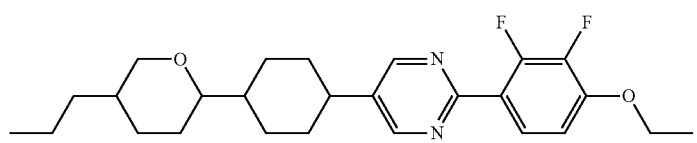 [SMILES: CCCC1CCC(C2CCC(c3cnc(-c4ccc(OCC)c(F)c4F)nc3)CC2)OC1] |
| 154 | 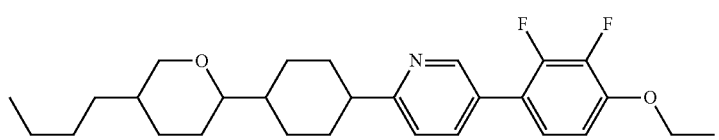 [SMILES: CCCCC1CCC(C2CCC(c3ccc(-c4ccc(OCC)c(F)c4F)cn3)CC2)OC1] |
| 155 | 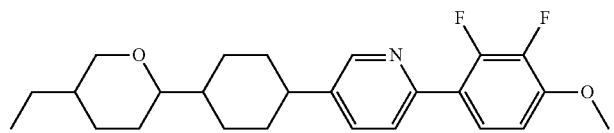 [SMILES: CCC1CCC(C2CCC(c3ccc(-c4ccc(OC)c(F)c4F)nc3)CC2)OC1] |
| 156 | 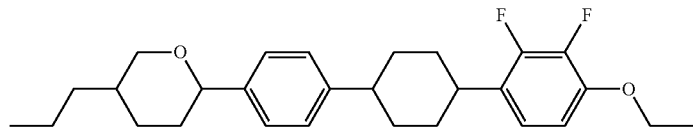 [SMILES: CCCC1CCC(c2ccc(C3CCC(c4ccc(OCC)c(F)c4F)CC3)cc2)OC1] |
| 157 | 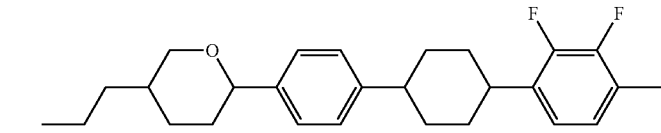 [SMILES: CCCC1CCC(c2ccc(C3CCC(c4ccc(C)c(F)c4F)CC3)cc2)OC1] |
| 158 | 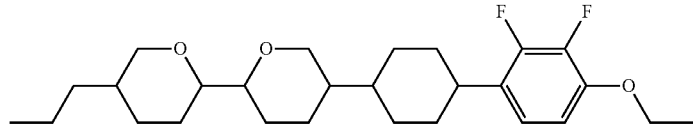 |
| 159 | 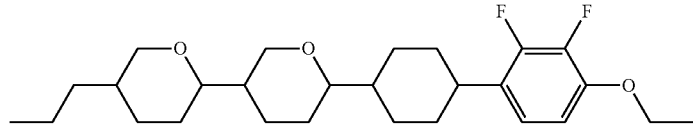 |
| 160 | 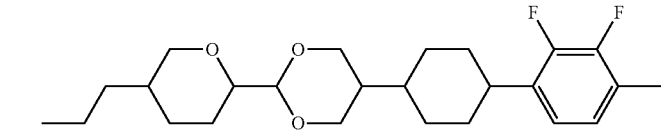 [SMILES: CCCC1CCC(C2OCC(C3CCC(c4ccc(C)c(F)c4F)CC3)CO2)OC1] |
| 161 | 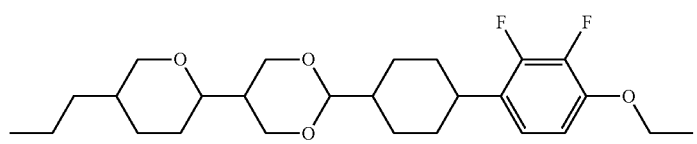 |

US 9,663,716 B2
-continued
| No. | |
|---|---|
| 162 | 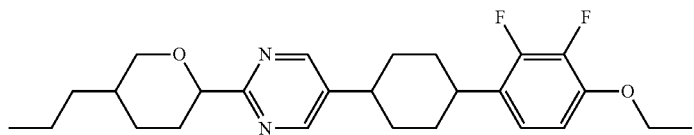 |
| 163 | 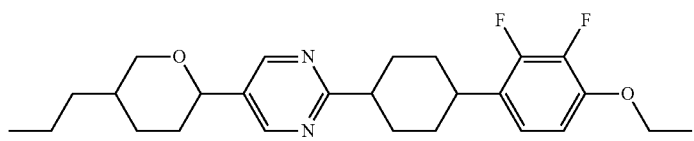 |
| 164 | 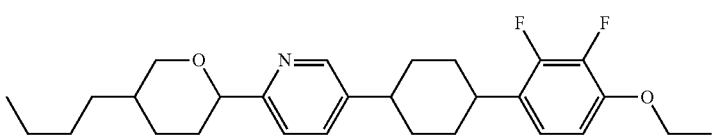 [SMILES: CCCCC1CCC(c2ccc(C3CCC(c4ccc(OCC)c(F)c4F)CC3)cn2)OC1] |
| 165 | 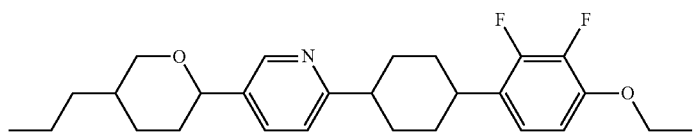 |
| 166 | 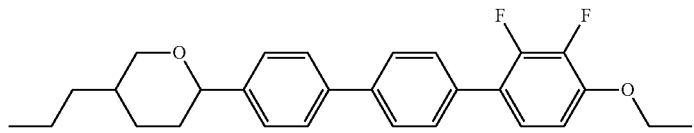 |
| 167 | 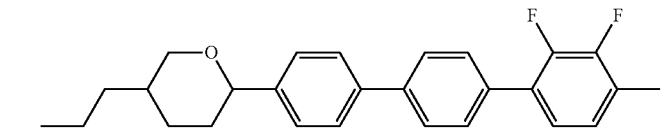 [SMILES: CCCC1CCC(c2ccc(-c3ccc(-c4ccc(C)c(F)c4F)cc3)cc2)OC1] |
| 168 | 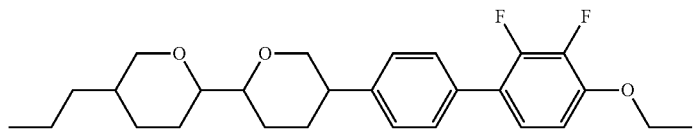 |
| 169 | 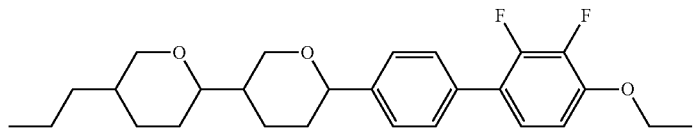 |
| 170 | 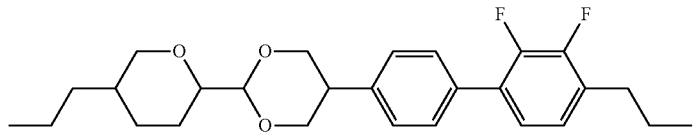 [SMILES: CCCc1ccc(-c2ccc(C3COC(C4CCC(CCC)CO4)OC3)cc2)c(F)c1F] |
| 171 | 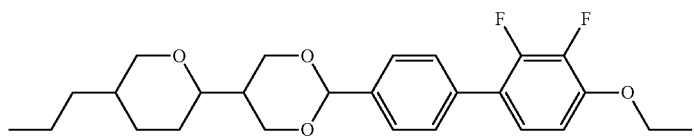 [SMILES: CCCC1CCC(C2COC(c3ccc(-c4ccc(OCC)c(F)c4F)cc3)OC2)OC1] |
| 172 | 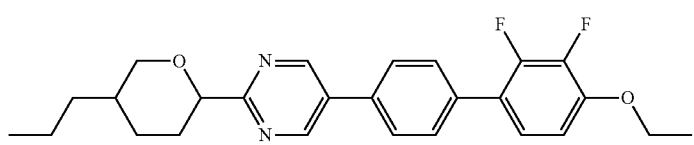 [SMILES: CCCC1CCC(c2ncc(-c3ccc(-c4ccc(OCC)c(F)c4F)cc3)cn2)OC1] |

-continued
| No. | |
|---|---|
| 173 | 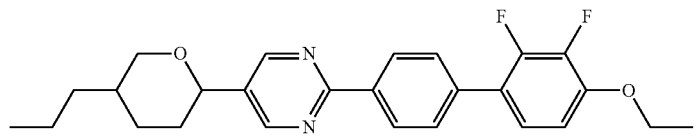 [SMILES: CCCC1CCC(c2cnc(-c3ccc(-c4ccc(OCC)c(F)c4F)cc3)nc2)OC1] |
| 174 | 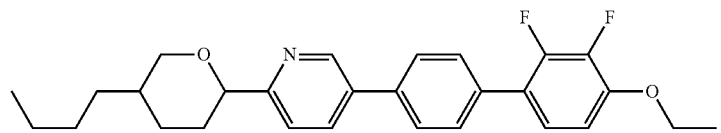 |
| 175 | 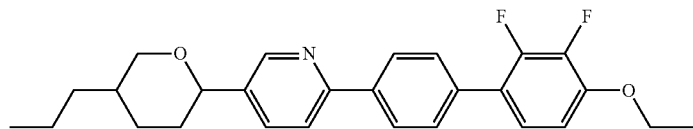 |
| 176 | 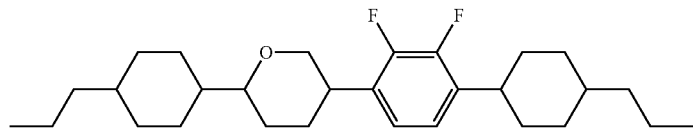 |
| 177 | 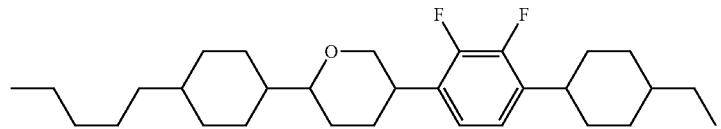 |
| 178 | 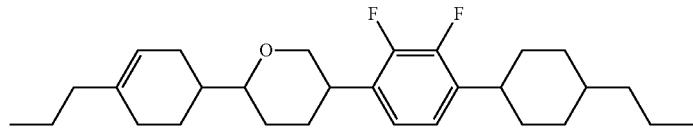 |
| 179 | 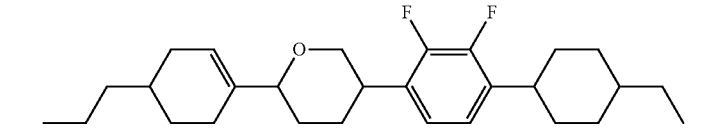 [SMILES: CCCC1CC=C(C2CCC(c3ccc(C4CCC(CC)CC4)c(F)c3F)CO2)CC1] |
| 180 | 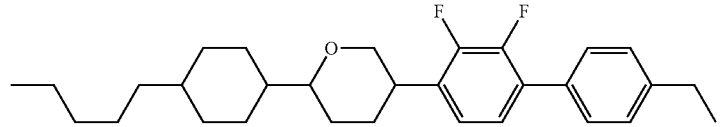 [SMILES: CCCCCC1CCC(C2CCC(c3ccc(-c4ccc(CC)cc4)c(F)c3F)CO2)CC1] |
| 181 | 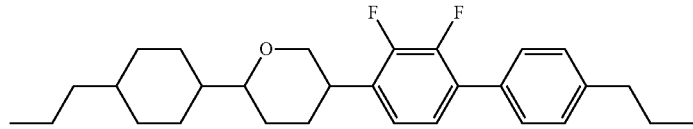 |
| 182 | 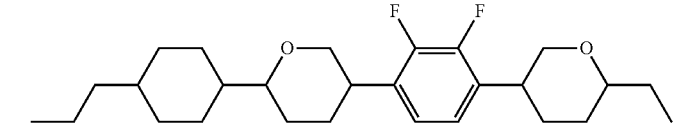 |
| 183 | 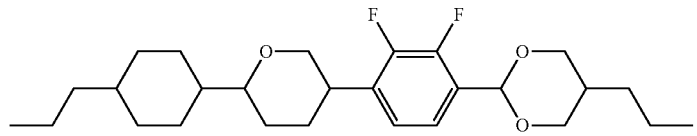 |

-continued
| No. | |
|---|---|
| 184 | 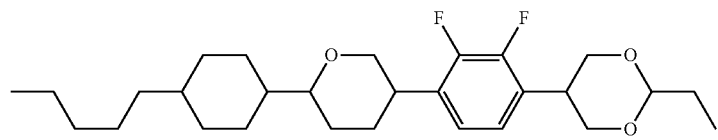 [SMILES: CCCCCC1CCC(C2CCC(c3ccc(C4COC(CC)OC4)c(F)c3F)CO2)CC1] |
| 185 | 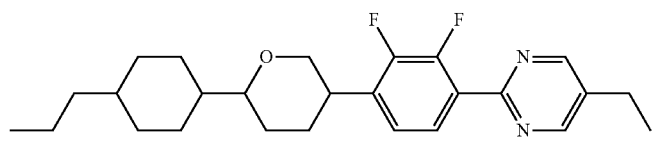 |
| 186 | 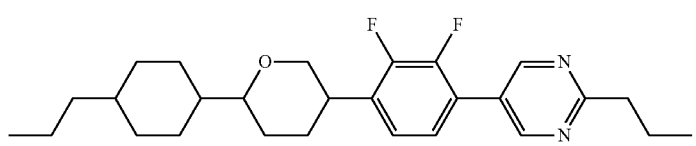 |
| 187 | 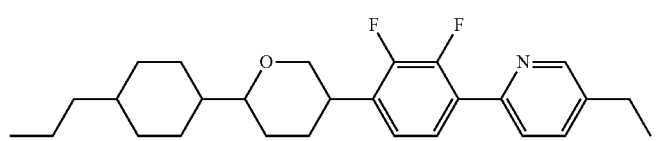 [SMILES: CCCC1CCC(C2CCC(c3ccc(-c4ccc(CC)cn4)c(F)c3F)CO2)CC1] |
| 188 | 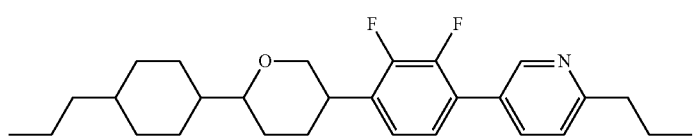 |
| 189 | 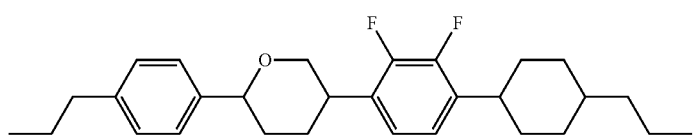 |
| 190 | 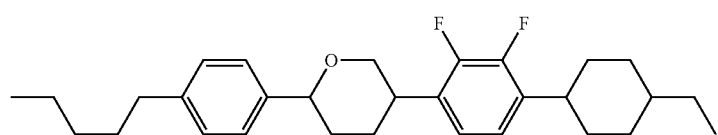 [SMILES: CCCCCc1ccc(C2CCC(c3ccc(C4CCC(CC)CC4)c(F)c3F)CO2)cc1] |
| 191 | 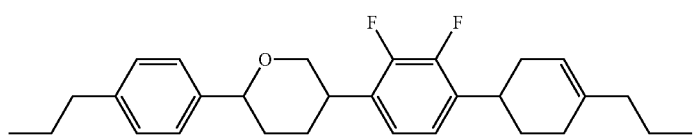 [SMILES: CCCC1=CCC(c2ccc(C3CCC(c4ccc(CCC)cc4)OC3)c(F)c2F)CC1] |
| 192 | 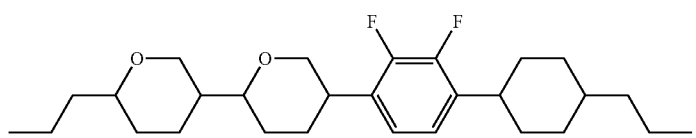 |
| 193 | 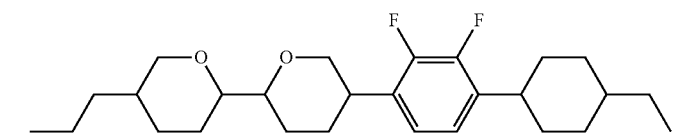 [SMILES: CCCC1CCC(C2CCC(c3ccc(C4CCC(CC)CC4)c(F)c3F)CO2)OC1] |
| 194 | 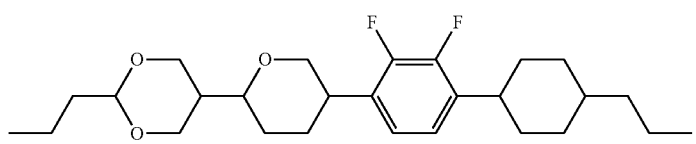 |

| No. | |
|---|---|
| 195 | 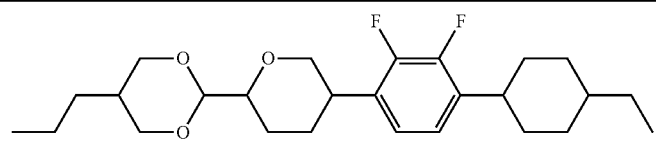 |
| 196 | 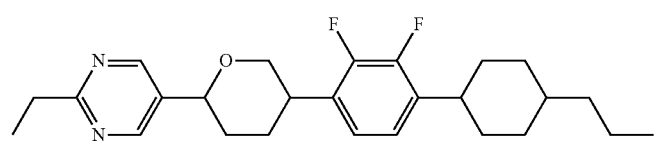 [SMILES: CCCC1CCC(c2ccc(C3CCC(c4cnc(CC)nc4)OC3)c(F)c2F)CC1] |
| 197 | 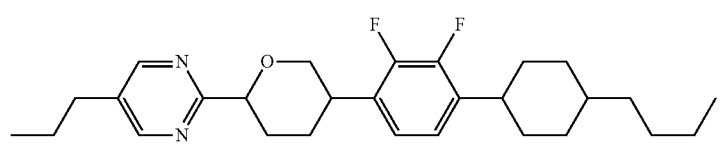 [SMILES: CCCCC1CCC(c2ccc(C3CCC(c4ncc(CCC)cn4)OC3)c(F)c2F)CC1] |
| 198 | 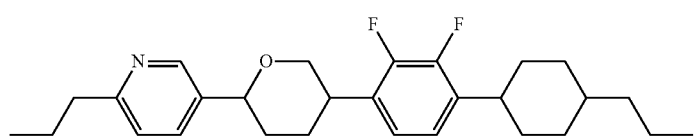 |
| 199 | 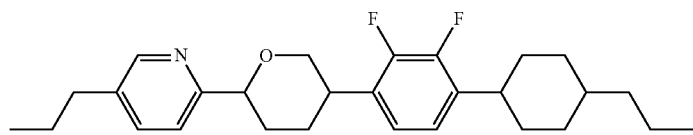 |
| 200 | 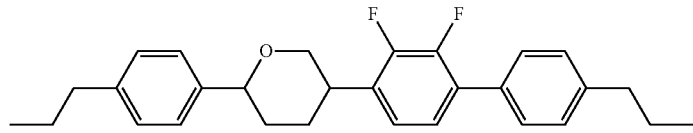 [SMILES: CCCc1ccc(-c2ccc(C3CCC(c4ccc(CCC)cc4)OC3)c(F)c2F)cc1] |
| 201 | 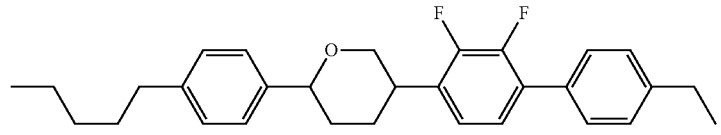 [SMILES: CCCCCc1ccc(C2CCC(c3ccc(-c4ccc(CC)cc4)c(F)c3F)CO2)cc1] |
| 202 | 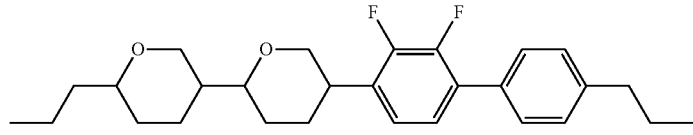 [SMILES: CCCc1ccc(-c2ccc(C3CCC(C4CCC(CCC)OC4)OC3)c(F)c2F)cc1] |
| 203 | 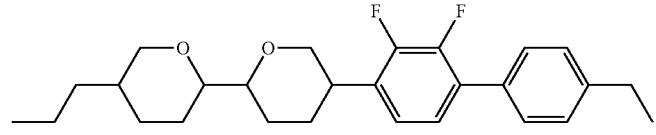 [SMILES: CCCC1CCC(C2CCC(c3ccc(-c4ccc(CC)cc4)c(F)c3F)CO2)OC1] |
| 204 | 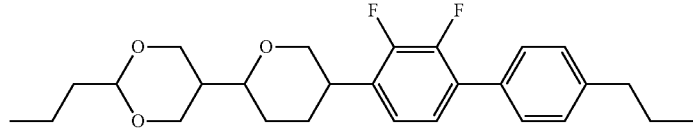 [SMILES: CCCc1ccc(-c2ccc(C3CCC(C4COC(CCC)OC4)OC3)c(F)c2F)cc1] |
| 205 | 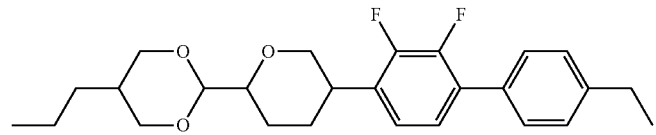 |

| No. | |
|---|---|
| 206 | 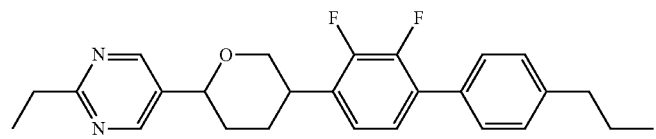 [SMILES: CCCc1ccc(-c2ccc(C3CCC(c4cnc(CC)nc4)OC3)c(F)c2F)cc1] |
| 207 | 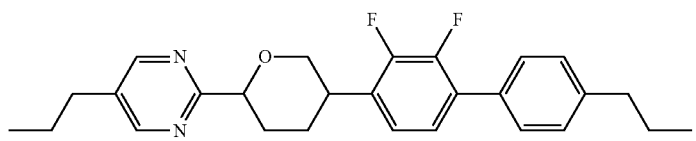 [SMILES: CCCc1ccc(-c2ccc(C3CCC(c4ncc(CCC)cn4)OC3)c(F)c2F)cc1] |
| 208 | 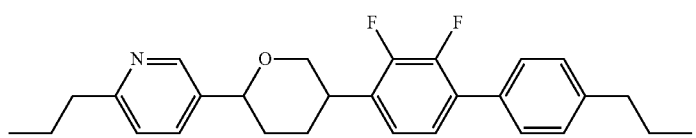 |
| 209 | 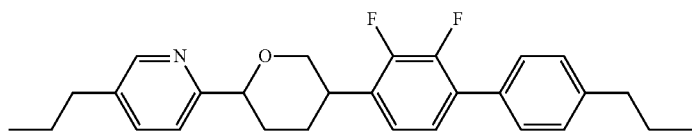 [SMILES: CCCc1ccc(-c2ccc(C3CCC(c4ccc(CCC)cn4)OC3)c(F)c2F)cc1] |
| 210 | 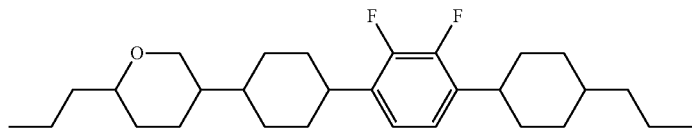 |
| 211 | 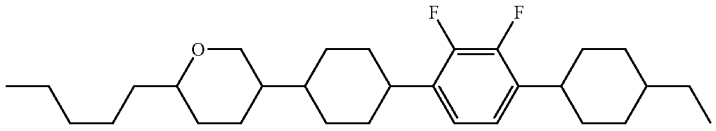 |
| 212 | 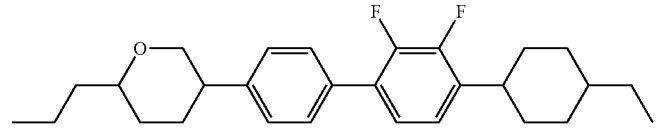 |
| 213 | 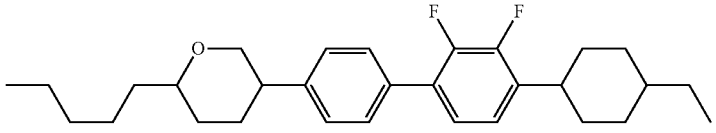 |
| 214 | 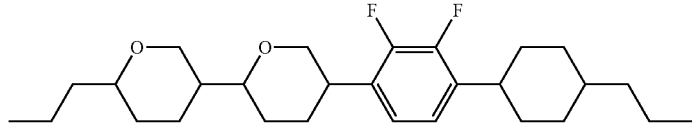 [SMILES: CCCC1CCC(c2ccc(C3CCC(C4CCC(CCC)OC4)OC3)c(F)c2F)CC1] |
| 215 | 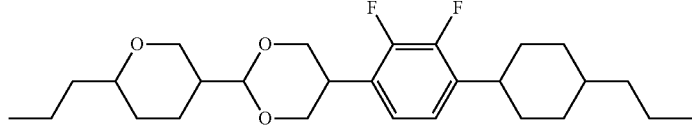 |
| 216 | 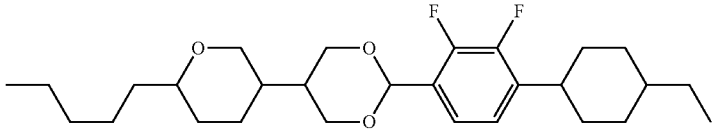 [SMILES: CCCCCC1CCC(C2COC(c3ccc(C4CCC(CC)CC4)c(F)c3F)OC2)CO1] |

-continued
| No. | |
|---|---|
| 217 | 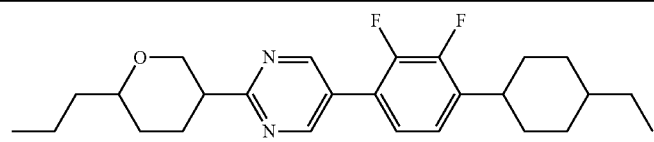 |
| 218 | 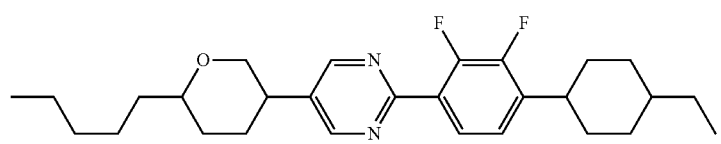 |
| 219 | 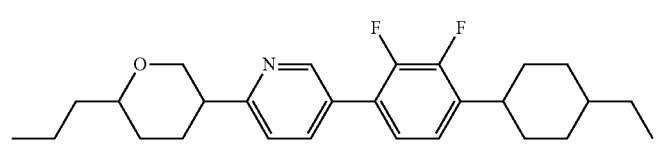 [SMILES: CCCC1CCC(c2ccc(-c3ccc(C4CCC(CC)CC4)c(F)c3F)cn2)CO1] |
| 220 | 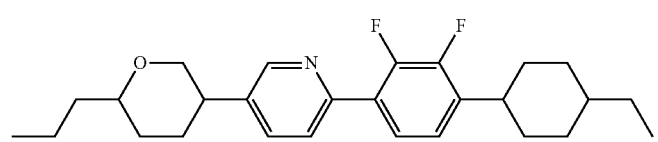 |
| 221 | 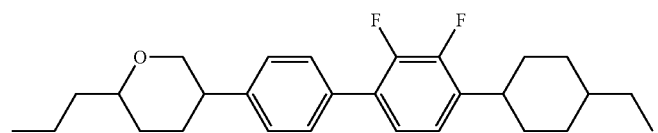 [SMILES: CCCC1CCC(c2ccc(-c3ccc(C4CCC(CC)CC4)c(F)c3F)cc2)CO1] |
| 222 | 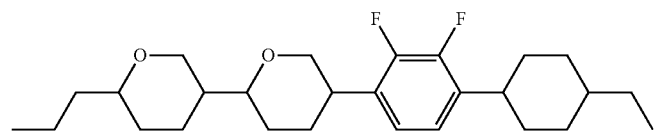 [SMILES: CCCC1CCC(C2CCC(c3ccc(C4CCC(CC)CC4)c(F)c3F)CO2)CO1] |
| 223 | 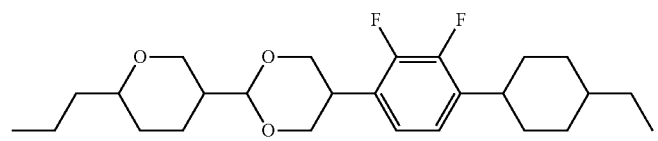 |
| 224 | 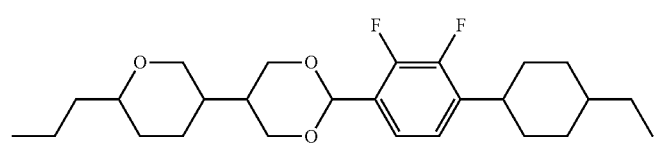 |
| 225 | 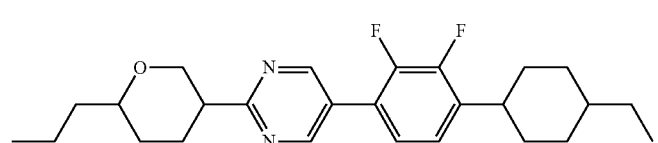 |
| 226 | 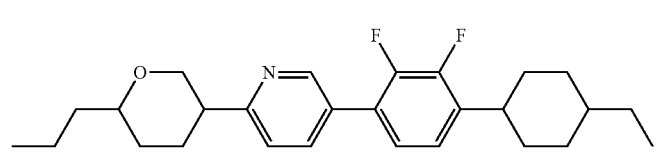 [SMILES: CCCC1CCC(c2ccc(-c3ccc(C4CCC(CC)CC4)c(F)c3F)cn2)CO1] |
| 227 | 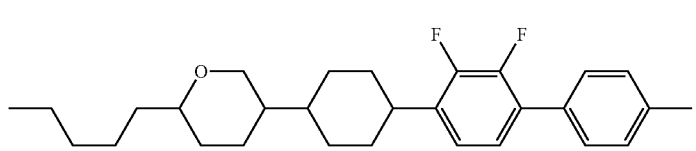 |

-continued
| No. | |
|---|---|
| 228 | 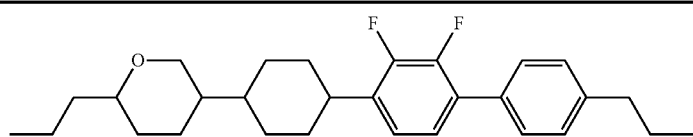 |
| 229 | 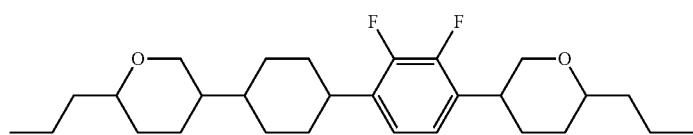 |
| 230 | 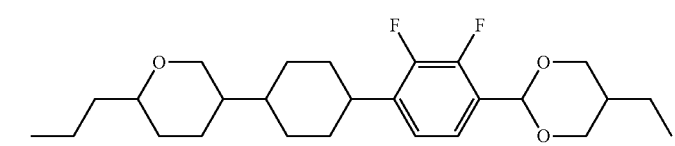 |
| 231 | 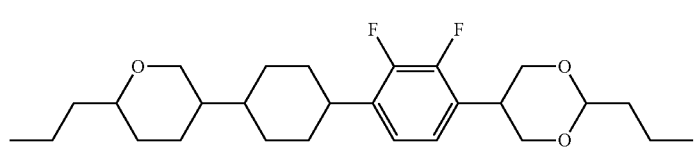 |
| 232 | 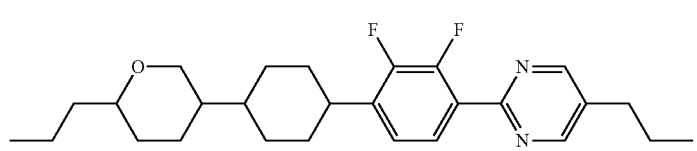 |
| 233 | 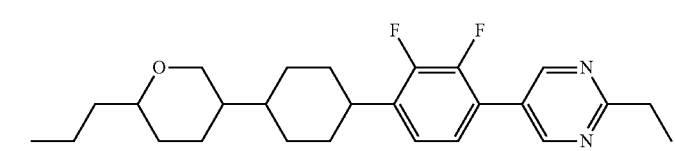 [SMILES: CCCC1CCC(C2CCC(c3ccc(-c4cnc(CC)nc4)c(F)c3F)CC2)CO1] |
| 234 | 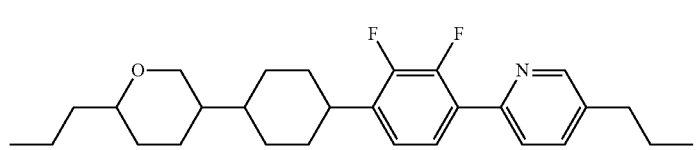 |
| 235 | 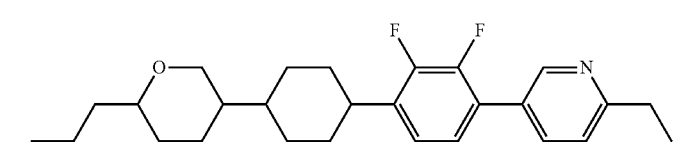 |
| 236 | 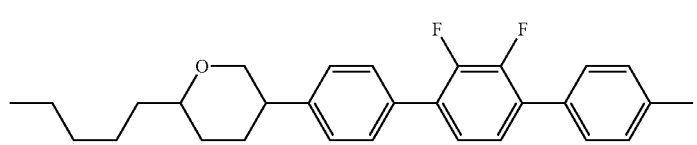 |
| 237 | 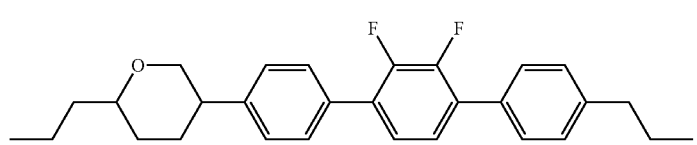 |
| 238 | 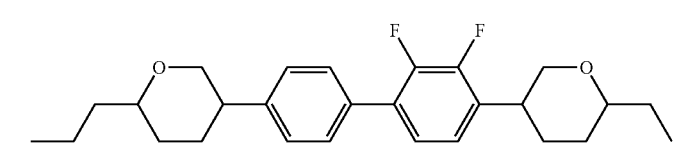 |

-continued
| No. | |
|---|---|
| 239 | 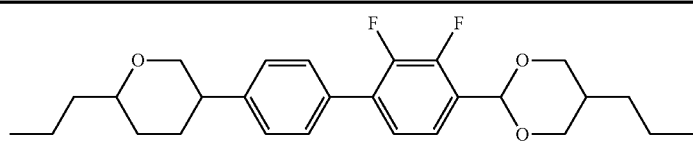 |
| 240 | 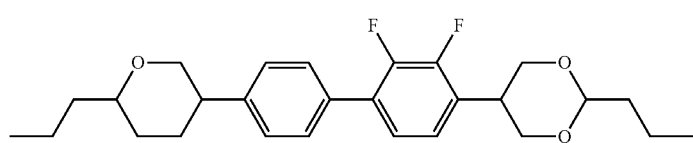 |
| 241 | 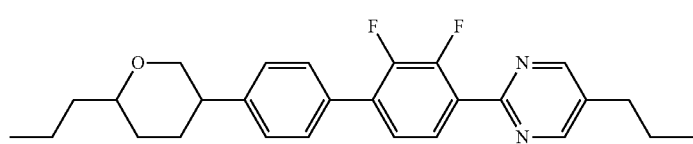 |
| 242 | 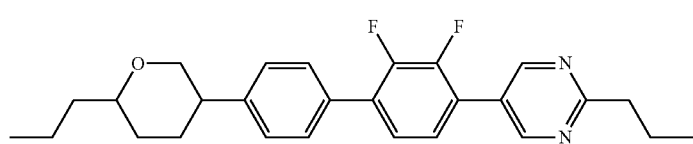 |
| 243 | 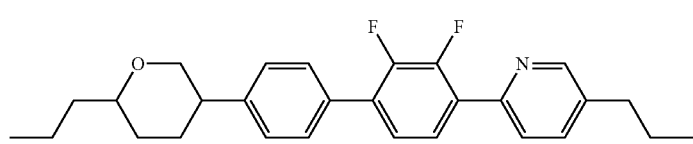 |
| 244 | 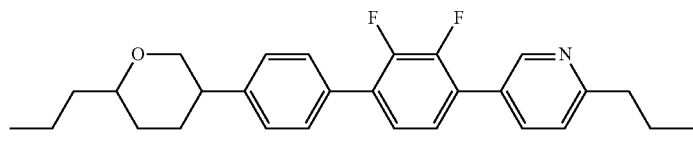 |
| 245 | 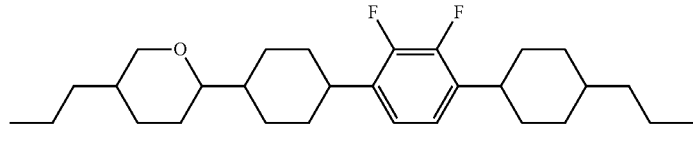 |
| 246 | 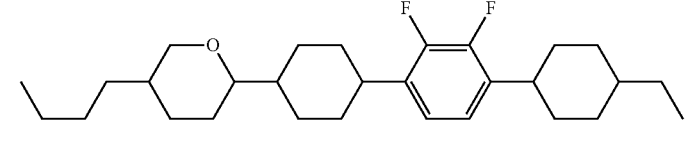 [SMILES: CCCCC1CCC(C2CCC(c3ccc(C4CCC(CC)CC4)c(F)c3F)CC2)OC1] |
| 247 | 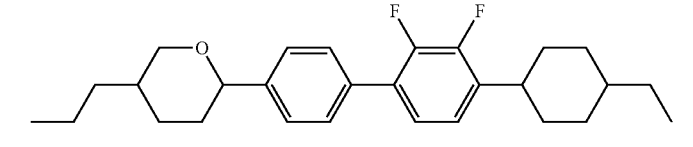 |
| 248 | 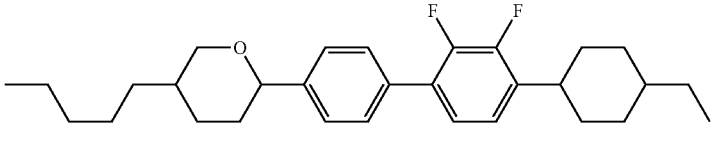 |
| 249 | 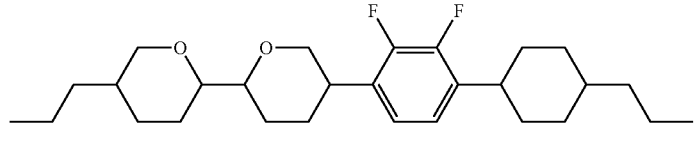 |

| No. | |
|---|---|
| 250 | 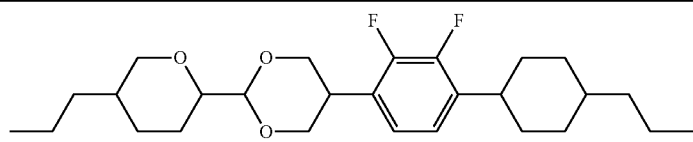 |
| 251 | 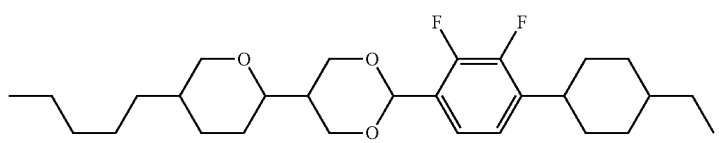 [SMILES: CCCCCC1CCC(C2COC(c3ccc(C4CCC(CC)CC4)c(F)c3F)OC2)OC1] |
| 252 | 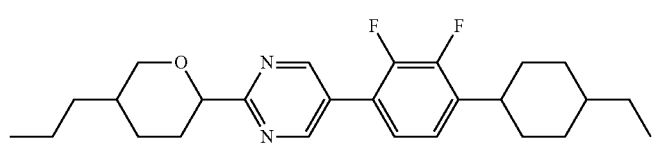 |
| 253 | 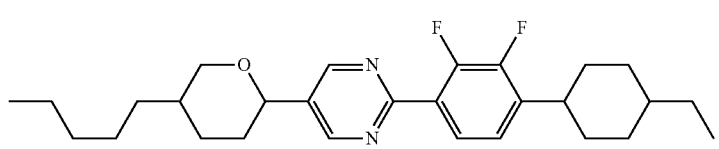 |
| 254 | 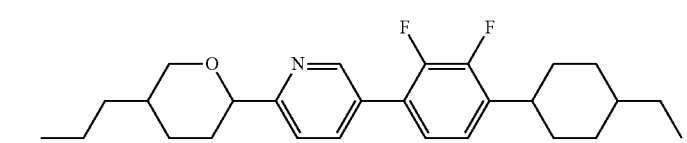 |
| 255 | 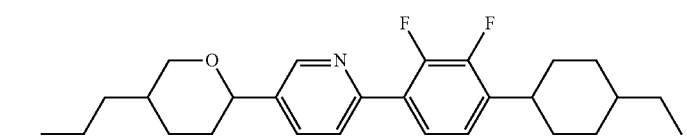 |
| 256 | 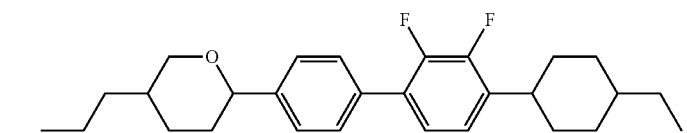 |
| 257 | 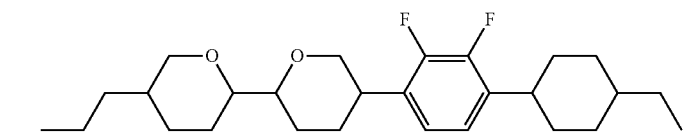 |
| 258 | 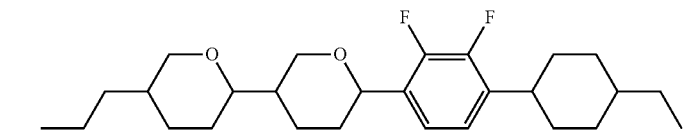 |
| 259 | 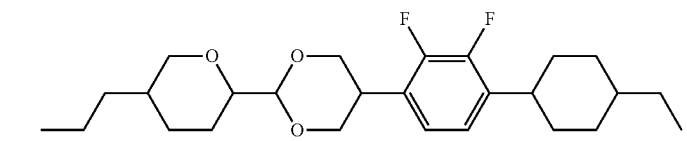 |
| 260 | 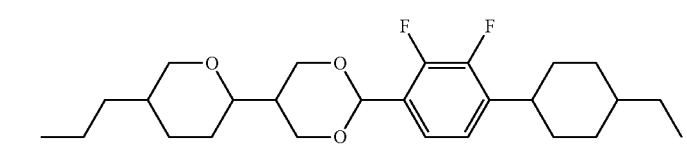 [SMILES: CCCC1CCC(C2COC(c3ccc(C4CCC(CC)CC4)c(F)c3F)OC2)OC1] |

| No. | |
|---|---|
| 261 | 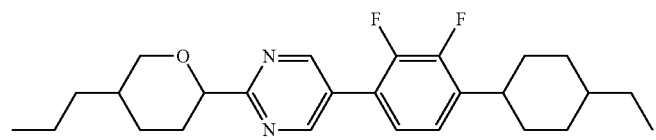 |
| 262 | 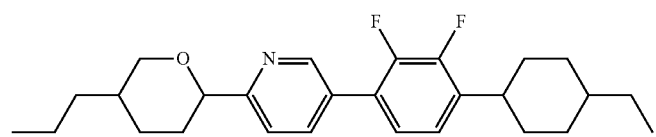 |
| 263 | 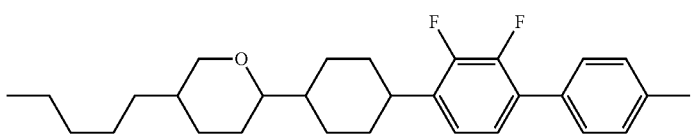 [SMILES: CCCCCC1CCC(C2CCC(c3ccc(-c4ccc(C)cc4)c(F)c3F)CC2)OC1] |
| 264 | 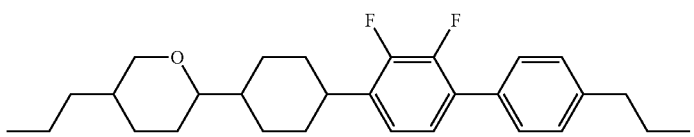 [SMILES: CCCc1ccc(-c2ccc(C3CCC(C4CCC(CCC)CO4)CC3)c(F)c2F)cc1] |
| 265 | 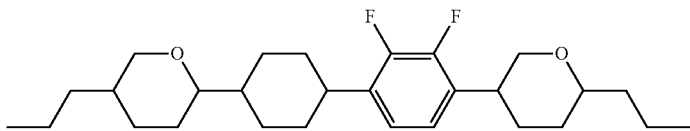 |
| 266 | 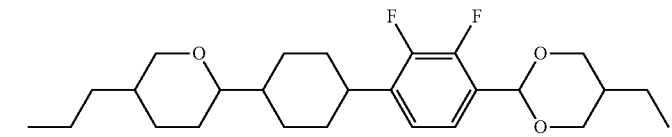 [SMILES: CCCC1CCC(C2CCC(c3ccc(C4OCC(CC)CO4)c(F)c3F)CC2)OC1] |
| 267 | 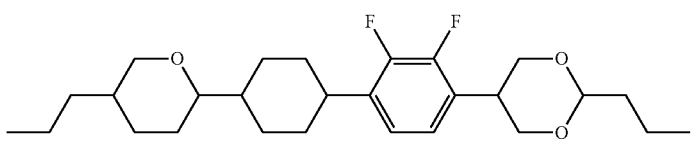 |
| 268 | 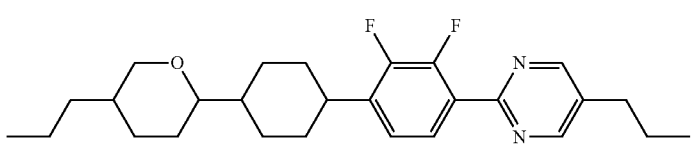 |
| 269 | 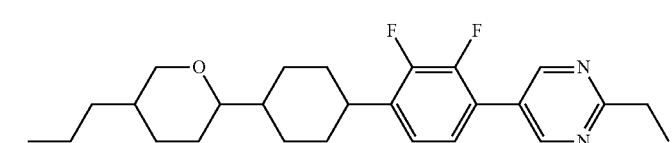 |
| 270 | 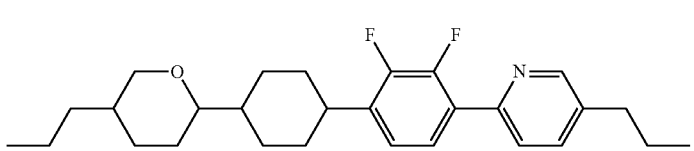 [SMILES: CCCc1ccc(-c2ccc(C3CCC(C4CCC(CCC)CO4)CC3)c(F)c2F)nc1] |
| 271 | 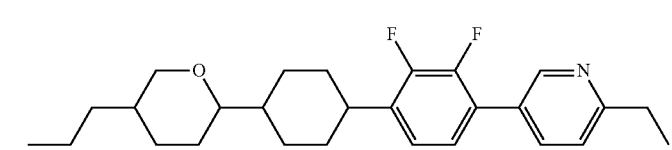 [SMILES: CCCC1CCC(C2CCC(c3ccc(-c4ccc(CC)nc4)c(F)c3F)CC2)OC1] |

| No. |
|---|
| 272 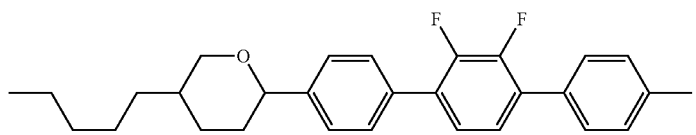 [SMILES: CCCCCC1CCC(c2ccc(-c3ccc(-c4ccc(C)cc4)c(F)c3F)cc2)OC1] |
| 273 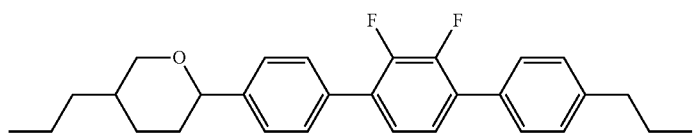 |
| 274 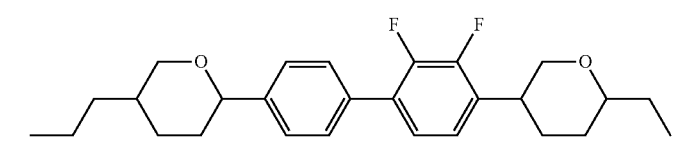 |
| 275 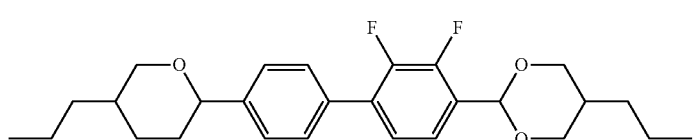 |
| 276 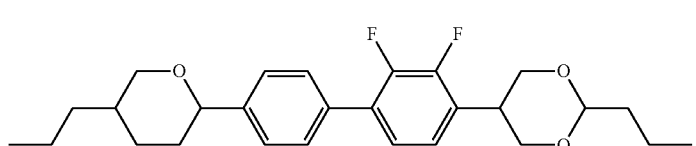 |
| 277 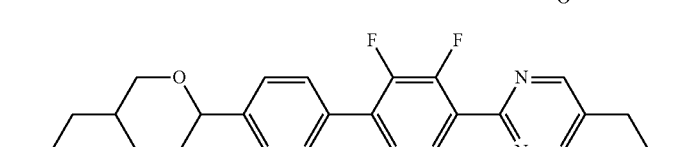 |
| 278 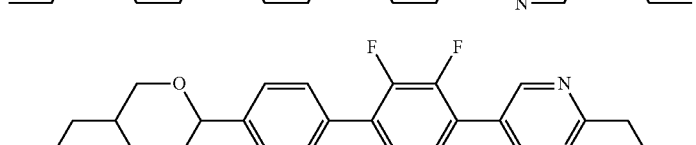 |
| 279 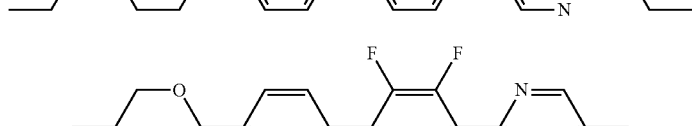 |
| 280 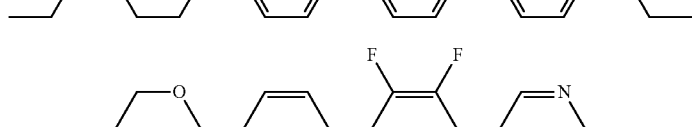 |
| 281 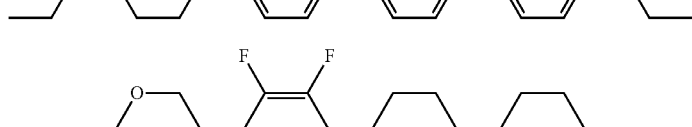 |
| 282 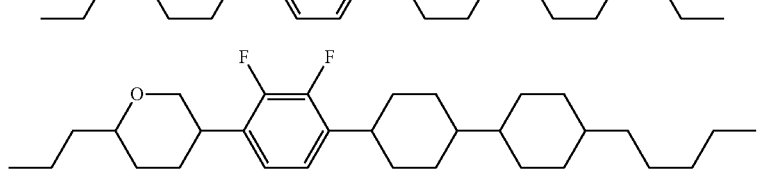 |

| No. |
|---|
| 283 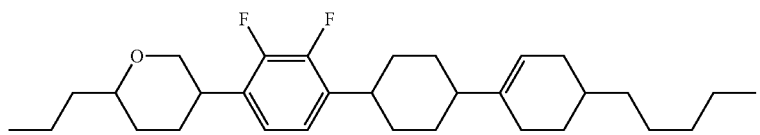 [SMILES: CCCCCC1CC=C(C2CCC(c3ccc(C4CCC(CCC)OC4)c(F)c3F)CC2)CC1] |
| 284 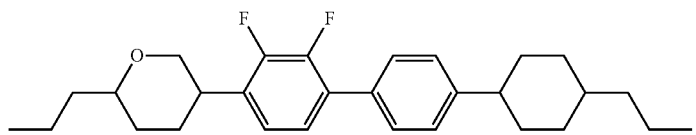 |
| 285 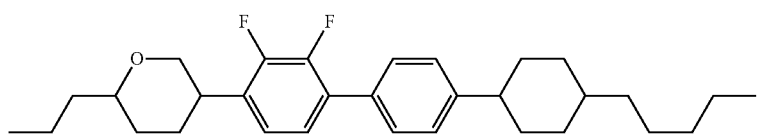 |
| 286 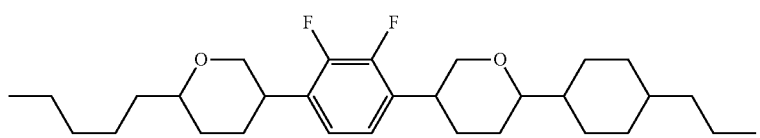 [SMILES: CCCCCC1CCC(c2ccc(C3CCC(C4CCC(CCC)CC4)OC3)c(F)c2F)CO1] |
| 287 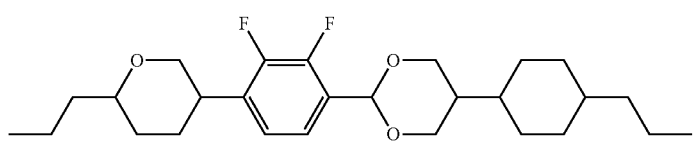 [SMILES: CCCC1CCC(C2COC(c3ccc(C4CCC(CCC)OC4)c(F)c3F)OC2)CC1] |
| 288 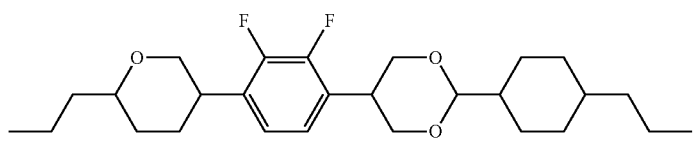 |
| 289 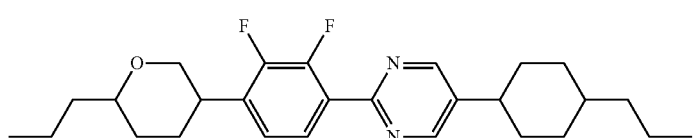 [SMILES: CCCC1CCC(c2ccc(-c3ccc(C4CCC(CCC)OC4)c(F)c3F)nc2)CC1] |
| 290 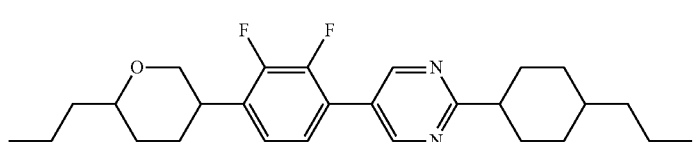 |
| 291 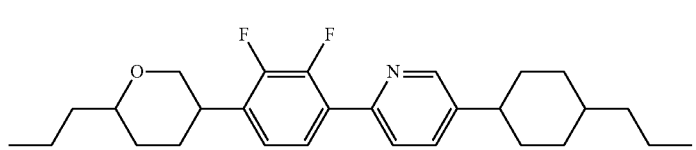 |
| 292 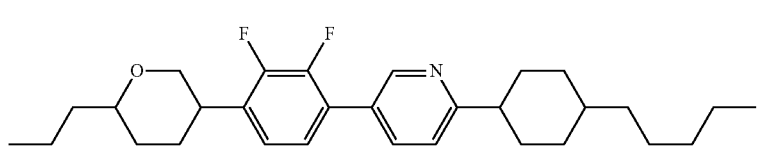 [SMILES: CCCCCC1CCC(c2ccc(-c3ccc(C4CCC(CCC)OC4)c(F)c3F)cn2)CC1] |
| 293 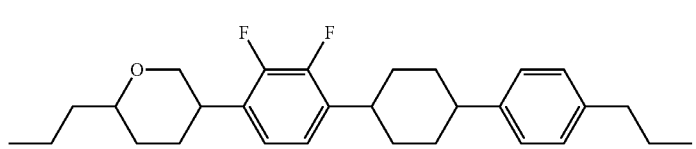 |

| No. | |
|---|---|
| 294 | 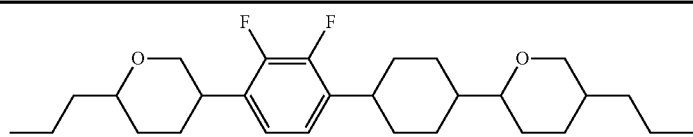 |
| 295 | 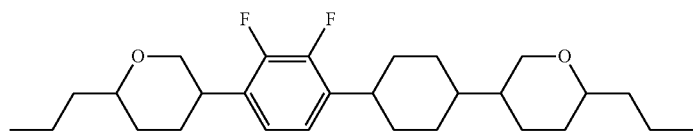 [SMILES: CCCC1CCC(c2ccc(C3CCC(C4CCC(CCC)OC4)CC3)c(F)c2F)CO1] |
| 296 | 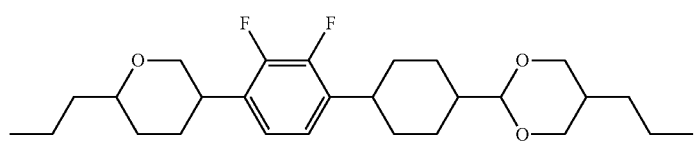 |
| 297 | 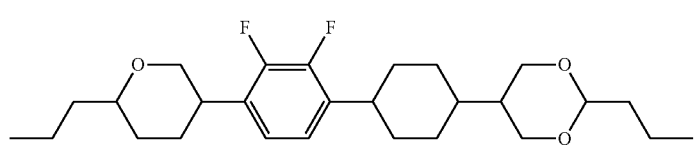 |
| 298 | 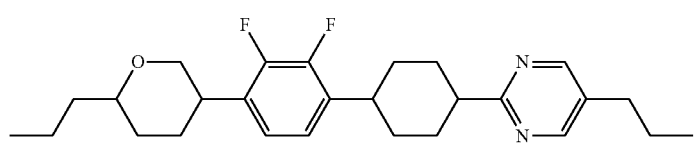 [SMILES: CCCc1cnc(C2CCC(c3ccc(C4CCC(CCC)OC4)c(F)c3F)CC2)nc1] |
| 299 | 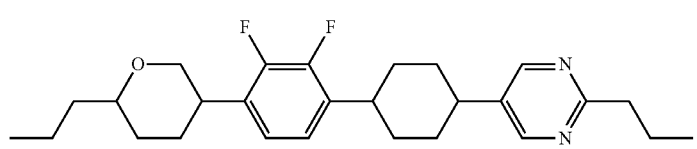 |
| 300 | 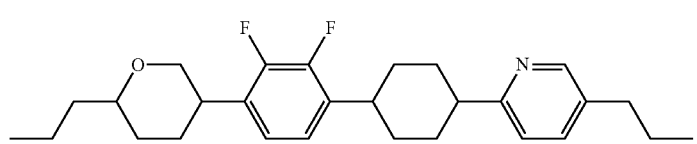 |
| 301 | 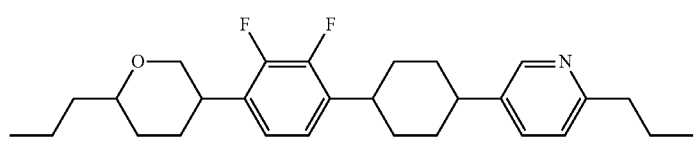 |
| 302 | 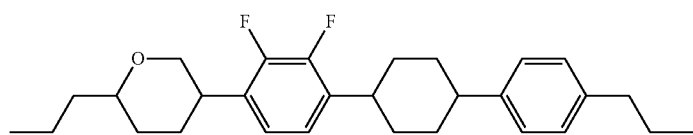 |
| 303 | 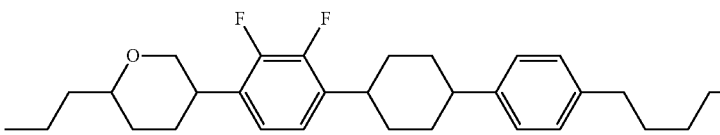 |
| 304 | 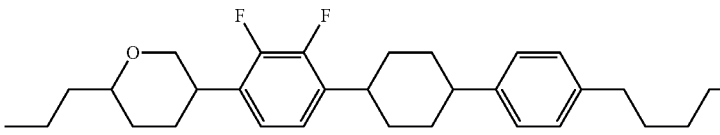 |

-continued

| No. | |
|---|---|
| 305 | 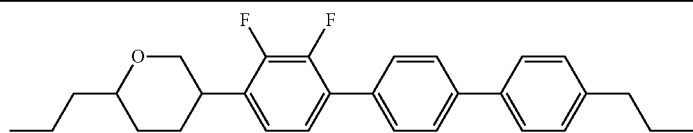 |
| 306 | 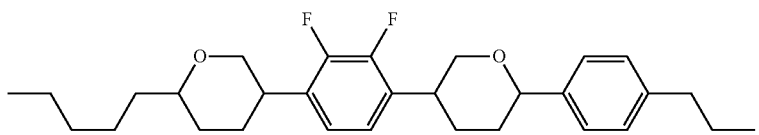 [SMILES: CCCCCC1CCC(c2ccc(C3CCC(c4ccc(CCC)cc4)OC3)c(F)c2F)CO1] |
| 307 | 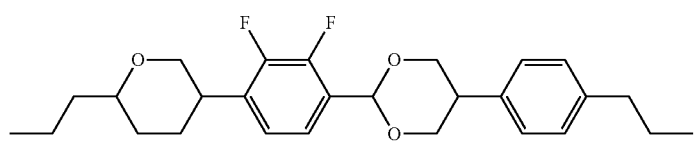 |
| 308 | 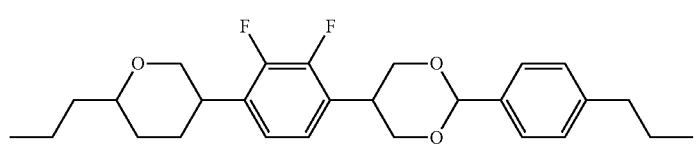 |
| 309 | 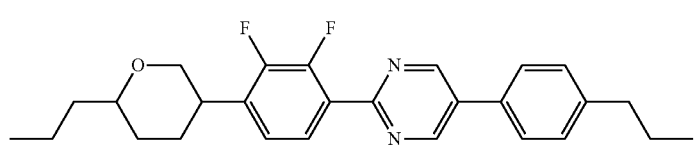 [SMILES: CCCc1ccc(-c2cnc(-c3ccc(C4CCC(CCC)OC4)c(F)c3F)nc2)cc1] |
| 310 | 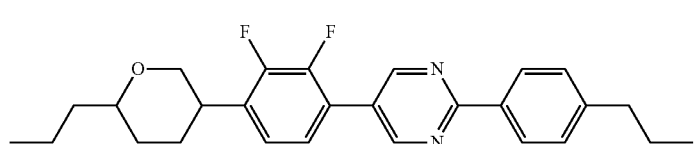 |
| 311 | 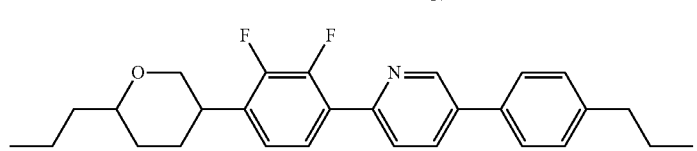 |
| 312 | 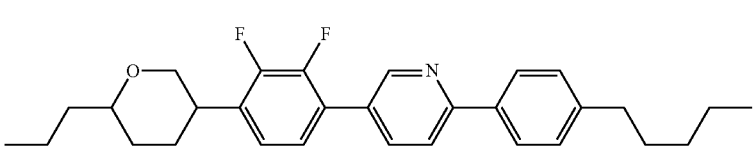 [SMILES: CCCCCc1ccc(-c2ccc(-c3ccc(C4CCC(CCC)OC4)c(F)c3F)cn2)cc1] |
| 313 | 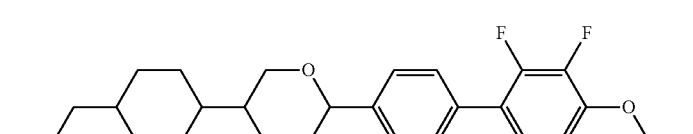 |

Comparative Example 1

The liquid crystal composition B was prepared from 15% by weight of the compound (b) that had been synthesized by the synthetic method described in JP 2000-008040 A (Patent document No. 3) and 85% by weight of the mother liquid crystals (A). The extrapolated values of physical properties of the liquid crystal compound (b) were calculated by measuring the physical property values of the resulting liquid crystal composition B and then by extrapolating the measured value. The extrapolated values were as follows.

Maximum temperature (NI)=121.3° C.; dielectric anisotropy ($\Delta\epsilon$)=−7.3; refractive index anisotropy ($\Delta n$)=0.107; viscosity ($\eta$)=61.4 mPa·s.

Example 10

The liquid crystal composition D was prepared from 10% by weight of the compound No. 1 and 90% by weight of the mother liquid crystals (A). The extrapolated values of physical properties of the compound No. 1 were calculated by measuring the physical property values of the resulting liquid crystal composition D and then by extrapolating the measured value. The extrapolated values were as follows.

Maximum temperature (NI)=234.6° C.; dielectric anisotropy ($\Delta\epsilon$)=−6.70; refractive index anisotropy ($\Delta n$)=0.126; viscosity ($\eta$)=63.5 mPa·s.

Example 11

The liquid crystal composition E was prepared from 15% by weight of the compound No. 41 and 85% by weight of the mother liquid crystals (A). The extrapolated values of physical properties of the compound No. 41 were calculated by measuring the physical property values of the resulting liquid crystal composition E and then by extrapolating the measured value. The extrapolated values were as follows.

Maximum temperature (NI)=238.6° C.; dielectric anisotropy ($\Delta\epsilon$)=−5.48; refractive index anisotropy ($\Delta n$)=0.122; viscosity ($\eta$)=66.1 mPa·s.

Example 12

The liquid crystal composition F was prepared from 15% by weight of the compound No. 109 and 85% by weight of the mother liquid crystals (A). The extrapolated values of physical properties of the compound No. 109 were calculated by measuring the physical property values of the resulting liquid crystal composition F and then by extrapolating the measured value. The extrapolated values were as follows.

Maximum temperature (NI)=243.3° C.; dielectric anisotropy ($\Delta\epsilon$)=−5.59; refractive index anisotropy ($\Delta n$)=0.126; viscosity ($\eta$)=65.4 mPa·s.

Example 13

The liquid crystal composition G was prepared from 15% by weight of the compound No. 44 and 85% by weight of the mother liquid crystals (A). The extrapolated values of physical properties of the compound No. 44 were calculated by measuring the physical property values of the resulting liquid crystal composition G and then by extrapolating the measured value. The extrapolated values were as follows.

Maximum temperature (NI)=238.6° C.; dielectric anisotropy ($\Delta\epsilon$)=−5.42; refractive index anisotropy ($\Delta n$)=0.182; viscosity ($\eta$)=82.4 mPa·s.

Example 14

The liquid crystal composition H was prepared from 15% by weight of the compound No. 40 and 85% by weight of the mother liquid crystals (A). The extrapolated values of physical properties of the compound No. 40 were calculated by measuring the physical property values of the resulting liquid crystal composition H and then by extrapolating the measured value. The extrapolated values were as follows.

Maximum temperature (NI)=245.3° C.; dielectric anisotropy ($\Delta\epsilon$)=−5.71; refractive index anisotropy ($\Delta n$)=0.122; viscosity ($\eta$)=72.3 mPa·s.

Example 15

The liquid crystal composition I was prepared from 15% by weight of the compound No. 108 and 85% by weight of the mother liquid crystals (A). The extrapolated values of physical properties of the compound No. 108 were calculated by measuring the physical property values of the resulting liquid crystal composition I and then by extrapolating the measured value. The extrapolated values were as follows.

Maximum temperature (NI)=245.3° C.; dielectric anisotropy ($\Delta\epsilon$)=−5.41; refractive index anisotropy ($\Delta n$)=0.128; viscosity ($\eta$)=69.5 mPa·s.

Example 16

The liquid crystal composition J was prepared from 15% by weight of the compound No. 75 and 85% by weight of the mother liquid crystals (A). The extrapolated values of physical properties of the compound No. 75 were calculated by measuring the physical property values of the resulting liquid crystal composition J and then by extrapolating the measured value. The extrapolated values were as follows.

Maximum temperature (NI)=245.9° C.; dielectric anisotropy ($\Delta\epsilon$)=−4.05; refractive index anisotropy ($\Delta n$)=0.122; viscosity ($\eta$)=60.6 mPa·s.

Example 17

The liquid crystal composition K was prepared from 15% by weight of the compound No. 143 and 85% by weight of the mother liquid crystals (A). The extrapolated values of physical properties of the compound No. 143 were calculated by measuring the physical property values of the resulting liquid crystal composition K and then by extrapolating the measured value. The extrapolated values were as follows.

Maximum temperature (NI)=243.9° C.; dielectric anisotropy ($\Delta\epsilon$)=−4.74; refractive index anisotropy ($\Delta n$)=0.124; viscosity ($\eta$)=63.3 mPa·s.

Example 18

The liquid crystal composition L was prepared from 15% by weight of the compound No. 313 and 85% by weight of the mother liquid crystals (A). The extrapolated values of physical properties of the compound No. 313 were calculated by measuring the physical property values of the resulting liquid crystal composition L and then by extrapolating the measured value. The extrapolated values were as follows.

Maximum temperature (NI)=252.6° C.; dielectric anisotropy ($\Delta\epsilon$)=−4.88; refractive index anisotropy ($\Delta n$)=0.191; viscosity ($\eta$)=88.9 mPa·s.

Comparative Example 2

The liquid crystal composition M was prepared from 3% by weight of the compound (c) prepared by the method described in the example as a reference and 97% by weight of the mother liquid crystals (A). The extrapolated values of physical properties of the liquid crystal compound (c) were calculated by measuring the physical property values of the resulting liquid crystal composition M and then by extrapolating the measured value. The extrapolated values were as follows.

Maximum temperature (NI)=261.3° C.; dielectric anisotropy ($\Delta\epsilon$)=−2.7; refractive index anisotropy ($\Delta n$)=0.150; viscosity ($\eta$)=70.5 mPa·s.

It was found that the absolute value of the dielectric anisotropy of the liquid crystal compound (c) was small in comparison with the compound No. 1 that was similar to the compound (c).

As a molecular weight increases, viscosity increases generally. The compound No. 1 in Example 4, the compound No. 41 in Example 5 and the compound No. 109 in Example 6 have an additional molecular weight corresponding to one cyclohexane ring in comparison with the compound (b) in Comparative example. However, their viscosities were surprisingly equivalent. Furthermore, it was found that the compound No. 1, the compound No. 41 and the compound No. 109 had a much high maximum temperature (NI) when they were compared with the compound (b).

Accordingly, it was found that the compound No. 1, the compound No. 41 and the compound No. 109 were superior in view of a much high maximum temperature (NI) in comparison with the compound (b), although they had an equivalent viscosity.

Examples of the Liquid Crystal Composition

Typical compositions of the invention were summarized in Examples 19 to 32. First, compounds that are a component of the composition and their amounts (% by weight) were shown. The compounds were expressed in the symbols of a left-terminal group, a bonding group, a ring structure and a right-terminal group according to the definition in Table 1.

TABLE 1

Method of Description of Compounds using Symbols
R—(A$_1$)—Z$_1$— . . . —Z$_n$—(A$_n$)—R'

| 1) Left-terminal Group R— | Symbol |
|---|---|
| C$_n$H$_{2n+1}$— | n- |
| C$_n$H$_{2n+1}$O— | nO— |
| C$_m$H$_{2m+1}$OC$_n$H$_{2n}$— | mOn— |
| CH$_2$=CH— | V— |
| C$_n$H$_{2n+1}$—CH=CH— | nV— |
| CH$_2$=CH—C$_n$H$_{2n}$— | Vn— |
| C$_m$H$_{2m+1}$—CH=CH—C$_n$H$_{2n}$— | mVn— |
| CF$_2$=CH— | VFF— |
| CF$_2$=CH—C$_n$H$_{2n}$— | VFFn— |

| 2) Right-terminal Group —R' | Symbol |
|---|---|
| —C$_n$H$_{2n+1}$ | -n |
| —OC$_n$H$_{2n+1}$ | —On |
| —CH=CH$_2$ | —V |
| —CH=CH—C$_n$H$_{2n+1}$ | —Vn |
| —C$_n$H$_{2n}$—CH=CH$_2$ | —nV |
| —CH=CF$_2$ | —VFF |
| —COOCH$_3$ | —EMe |
| —CN | —C |
| —F | —F |
| —Cl | —CL |
| —OCF$_3$ | —OCF3 |
| —CF$_3$ | —CF3 |

| 3) Bonding Group —Z$_n$— | Symbol |
|---|---|
| —C$_n$H$_{2n}$— | n |
| —COO— | E |
| —CH=CH— | V |
| —CH$_2$O— | 1O |
| —CF$_2$O— | X |
| —C≡C— | T |

| 4) Ring Structure —A$_n$— | Symbol |
|---|---|
|  | H |
| 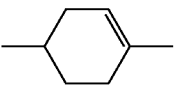 | Ch |

TABLE 1-continued

Method of Description of Compounds using Symbols
R—(A$_1$)—Z$_1$— . . . —Z$_n$—(A$_n$)—R'

| 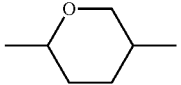 | Dh |
| 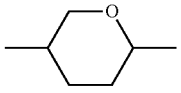 | dh |
| 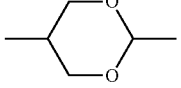 | G |
| 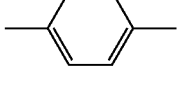 | B |
| 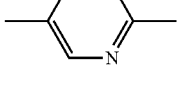 | Py |
| 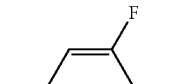 | B(2F) |
| 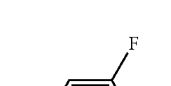 | B(F) |
| 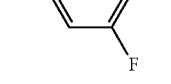 | B(F,F) |
| 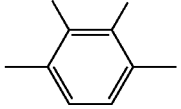 | B(2F,3F) |
| 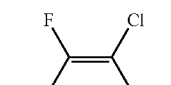 | B(2F,3CL) |
| 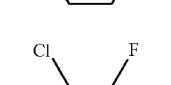 | B(2CL,3F) |

TABLE 1-continued

Method of Description of Compounds using Symbols
R—(A₁)—Z₁— . . . —Zₙ—(Aₙ)—R'

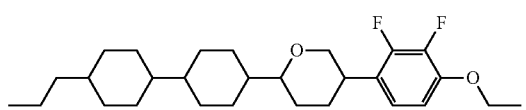 [SMILES: CCCC1CCC(C2CCC(C3CCC(c4ccc(OCC)c(F)c4F)CO3)CC2)CC1]
Cro(7F,8F)

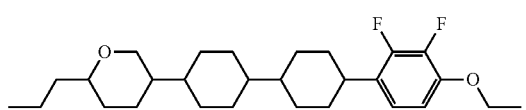 [SMILES: CCCC1CCC(C2CCC(C3CCC(c4ccc(OCC)c(F)c4F)CC3)CC2)CO1]
Np(1F,7F,8F)

5) Examples of Description

Example 1. 3-HHDhB(2F,3F)—O2

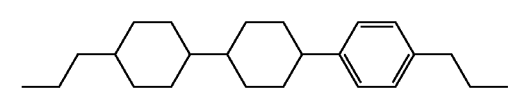

Example 2. 3-DhHHB(2F,3F)—O2

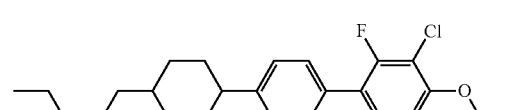

Example 3. 3-HHB-3

Example 4. 5-HBB(2F,3CL)—O2

Example 19

| | | |
|---|---|---|
| 3-HHDhB(2F,3F)-O2 | (No. 1) | 4% |
| 5-DhHHB(2F,3F)-O2 | (No. 109) | 4% |
| 3-HH-O1 | (12-1) | 8% |
| 5-HH-O1 | (12-1) | 4% |
| 3-HH-4 | (12-1) | 5% |
| 3-HB(2F,3F)-O2 | (6-1) | 12% |
| 5-HB(2F,3F)-O2 | (6-1) | 21% |
| 2-HHB(2F,3F)-1 | (7-1) | 5% |
| 3-HHB(2F,3F)-1 | (7-1) | 7% |
| 3-HHB(2F,3F)-O2 | (7-1) | 10% |
| 5-HHB(2F,3F)-O2 | (7-1) | 20% |

NI = 74.6° C.; Δn = 0.080; η = 25.3 mPa · s; Δε = −4.3.

Example 20

| | | |
|---|---|---|
| 5-HDhHB(2F,3F)-O2 | (No. 41) | 3% |
| 3-HDhBB(2F,3F)-O2 | (No. 44) | 7% |
| 3-HB-O1 | (12-5) | 15% |
| 3-HH-4 | (12-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 12% |
| 3-HHB(2F,3F)-O2 | (7-1) | 13% |
| 5-HHB(2F,3F)-O2 | (7-1) | 3% |
| 3-HHB-1 | (13-1) | 6% |

NI = 94.2° C.; Δn = 0.095; η = 38.8 mPa · s; Δε = −3.4.

Example 21

| | | |
|---|---|---|
| 3-HHDhB(2F,3F)-O2 | (No. 1) | 3% |
| 3-HDhBB(2F,3F)-O2 | (No. 44) | 3% |
| 3-HB-O1 | (12-5) | 15% |
| 3-HH-4 | (12-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 12% |
| 3-HHB(2F,3F)-O2 | (7-1) | 13% |
| 5-HHB(2F,3F)-O2 | (7-1) | 7% |
| 6-HEB(2F,3F)-O2 | (6-6) | 6% |

NI = 86.2° C.; Δn = 0.089; η = 36.0 mPa · s; Δε = −3.7.

Example 22

| | | |
|---|---|---|
| 5-DhHHB(2F,3F)-O2 | (No. 109) | 3% |
| 3-HDhBB(2F,3F)-O2 | (No. 44) | 5% |
| 3-HH-4 | (12-1) | 14% |
| 3-H2B(2F,3F)-O2 | (6-4) | 22% |
| 5-H2B(2F,3F)-O2 | (6-4) | 22% |
| 2-HHB(2F,3CL)-O2 | (7-12) | 2% |
| 3-HHB(2F,3CL)-O2 | (7-12) | 3% |
| 4-HHB(2F,3CL)-O2 | (7-12) | 2% |
| 3-HBB(2F,3F)-O2 | (7-7) | 9% |
| V-HHB-1 | (13-1) | 6% |
| 3-HHB-3 | (13-1) | 6% |
| 3-HHEBH-3 | (14-6) | 3% |
| 3-HHEBH-4 | (14-6) | 3% |

NI = 85.9° C.; Δn = 0.096; η = 27.9 mPa · s; Δε = −3.8.

Example 23

| | | |
|---|---|---|
| 3-HDhHB(2F,3F)-O2 | (No. 40) | 3% |
| 3-DhHHB(2F,3F)-O2 | (No. 108) | 3% |
| 2-HH-5 | (12-1) | 3% |
| 3-HH-4 | (12-1) | 15% |
| 3-HH-5 | (12-1) | 4% |
| 3-H2B(2F,3F)-O2 | (6-4) | 12% |
| 5-H2B(2F,3F)-O2 | (6-4) | 15% |
| 3-HHB(2F,3CL)-O2 | (7-12) | 5% |
| 2-HBB(2F,3F)-O2 | (7-7) | 3% |
| 3-HBB(2F,3F)-O2 | (7-7) | 9% |
| 5-HBB(2F,3F)-O2 | (7-7) | 6% |
| 3-HHB-1 | (13-1) | 3% |
| 3-HHB-3 | (13-1) | 4% |

| | | |
|---|---|---|
| 3-HHB-O1 | (13-1) | 3% |
| 3-HB-O2 | (12-5) | 12% |

NI = 84.9° C.; Δn = 0.093; η = 20.6 mPa·s; Δε = −4.0.

The helical pitch was 60.3 μm when 0.25 part of the compound (Op-05) was added to the preceding composition.

Example 24

| | | |
|---|---|---|
| 3-HdhHB(2F,3F)-O2 | (No. 74) | 3% |
| 3-dhHHB(2F,3F)-O2 | (No. 142) | 3% |
| 3-HB-O1 | (12-5) | 15% |
| 3-HH-4 | (12-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 6% |
| 3-HHB(2F,3F)-O2 | (7-1) | 13% |
| 5-HHB(2F,3F)-O2 | (7-1) | 13% |
| 3-HHB-1 | (13-1) | 6% |

Example 25

| | | |
|---|---|---|
| 3-HHDhB(2F,3F)-O2 | (No. 1) | 4% |
| 5-DhHHB(2F,3F)-O2 | (No. 109) | 3% |
| 2-BEB(F)-C | (5-14) | 5% |
| 3-BEB(F)-C | (5-14) | 4% |
| 4-BEB(F)-C | (5-14) | 12% |
| 1V2-BEB(F,F)-C | (5-15) | 16% |
| 3-HB-O2 | (12-5) | 10% |
| 3-HH-4 | (12-1) | 3% |
| 3-HHB-F | (3-1) | 3% |
| 3-HHB-1 | (13-1) | 8% |
| 3-HHB-O1 | (13-1) | 4% |
| 3-HBEB-F | (3-37) | 4% |
| 5-HHEB-F | (3-10) | 7% |
| 3-H2BTB-2 | (13-17) | 4% |
| 3-H2BTB-3 | (13-17) | 4% |
| 3-H2BTB-4 | (13-17) | 4% |
| 3-HB(F)TB-2 | (13-18) | 5% |

NI = 89.1° C.; Δn = 0.141; Δε = 27.2; Vth; η = 39.3 mPa·sec.

Example 26

| | | |
|---|---|---|
| 5-HDhHB(2F,3F)-O2 | (No. 41) | 5% |
| 3-HDhBB(2F,3F)-O2 | (No. 44) | 7% |
| 1V2-BEB(F,F)-C | (5-15) | 6% |
| 3-HB-C | (5-1) | 18% |
| 2-BTB-1 | (12-10) | 10% |
| 5-HH-VFF | (12-1) | 30% |
| 3-HHB-1 | (13-1) | 4% |
| VFF-HHB-1 | (13-1) | 5% |
| VFF2-HHB-1 | (13-1) | 11% |
| 3-H2BTB-4 | (13-17) | 4% |

NI = 90.6° C.; Δn = 0.124; Δε = 5.3; η = 18.7 mPa·sec.

Example 27

| | | |
|---|---|---|
| 3-HHDhB(2F,3F)-O2 | (No. 1) | 4% |
| 5-DhHHB(2F,3F)-O2 | (No. 109) | 4% |
| 2-HB-C | (5-1) | 5% |
| 3-HB-C | (5-1) | 12% |
| 3-HB-O2 | (12-5) | 11% |
| 2-BTB-1 | (12-10) | 3% |
| 3-HHB-F | (3-1) | 4% |
| 3-HHB-1 | (13-1) | 8% |
| 3-HHB-O1 | (13-1) | 5% |
| 3-HHB-3 | (13-1) | 14% |
| 5-HHEB-F | (3-10) | 4% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 5% |

NI = 109.2° C.; Δn = 0.101; Δε = 3.7; η = 20.8 mPa·sec.

Example 28

| | | |
|---|---|---|
| 3-HDhHB(2F,3F)-O2 | (No. 40) | 3% |
| 3-DhHHB(2F,3F)-O2 | (No. 108) | 3% |
| 5-HB-CL | (2-2) | 18% |
| 3-HH-4 | (12-1) | 12% |
| 3-HH-5 | (12-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 7% |
| 4-HHB(F)-F | (3-2) | 9% |
| 5-HHB(F)-F | (3-2) | 9% |
| 7-HHB(F)-F | (3-2) | 8% |
| 5-HBB(F)-F | (3-23) | 4% |
| 1O1-HBBH-5 | (14-1) | 3% |
| 4-HHBB(F,F)-F | (4-6) | 3% |
| 5-HHBB(F,F)-F | (4-6) | 3% |
| 3-HH2BB(F,F)-F | (4-15) | 3% |

NI = 116.7° C.; Δn = 0.090; Δε = 2.8; η = 18.3 mPa·sec.

Example 29

| | | |
|---|---|---|
| 3-HdhHB(2F,3F)-O2 | (No. 74) | 5% |
| 3-dhHHB(2F,3F)-O2 | (No. 142) | 3% |
| 2-BEB(F)-C | (5-14) | 5% |
| 3-BEB(F)-C | (5-14) | 4% |
| 4-BEB(F)-C | (5-14) | 12% |
| 1V2-BEB(F,F)-C | (5-15) | 16% |
| 3-HB-O2 | (12-5) | 10% |
| 3-HH-4 | (12-1) | 5% |
| 3-HHB-F | (3-1) | 3% |
| 3-HHB-1 | (13-1) | 8% |
| 3-HHB-O1 | (13-1) | 4% |
| 3-HBEB-F | (3-37) | 4% |
| 3-HHEB-F | (3-10) | 4% |
| 3-H2BTB-2 | (13-17) | 4% |
| 3-H2BTB-3 | (13-17) | 4% |
| 3-H2BTB-4 | (13-17) | 4% |
| 3-HB(F)TB-2 | (13-18) | 5% |

Example 30

| | | |
|---|---|---|
| 3-HHDhB(2F,3F)-O2 | (No. 1) | 4% |
| 5-DhHHB(2F,3F)-O2 | (No. 109) | 4% |
| 3-HH-O1 | (12-1) | 8% |
| 5-HH-O1 | (12-1) | 4% |
| 3-HH-4 | (12-1) | 5% |
| 3-HB(2F,3F)-O2 | (6-1) | 7% |
| 5-HB(2F,3F)-O2 | (6-1) | 21% |
| 3-HHB(2F,3F)-1 | (7-1) | 7% |

-continued

| | | |
|---|---|---|
| 3-HHB(2F,3F)-O2 | (7-1) | 10% |
| 5-HHB(2F,3F)-O2 | (7-1) | 20% |
| 2-BB(2F,3F)B-3 | (8-1) | 5% |
| 2-BB(2F,3F)B-4 | (8-1) | 5% |

NI = 79.3° C.; Δn = 0.095; η = 26.2 mPa · s; Δε = −4.0.

Example 31

| | | |
|---|---|---|
| 3-HdhHB(2F,3F)-O2 | (No. 74) | 3% |
| 3-dhHHB(2F,3F)-O2 | (No. 142) | 7% |
| 3-HB-O1 | (12-5) | 20% |
| 3-HH-4 | (12-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 10% |
| 3-HHB(2F,3F)-1 | (7-1) | 12% |
| 3-HHB(2F,3F)-O2 | (7-1) | 8% |
| 3-HHB-1 | (13-1) | 6% |
| 5-HH1ONp(1F,7F,8F)-O4 | (9-3) | 5% |

Example 32

| | | |
|---|---|---|
| 3-HHDhB(2F,3F)-O2 | (No. 1) | 3% |
| 3-HDhBB(2F,3F)-O2 | (No. 44) | 3% |
| 3-HB-O1 | (12-5) | 15% |
| 3-HH-4 | (12-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 2% |
| 3-HHB(2F,3F)-O2 | (7-1) | 13% |
| 5-HHB(2F,3F)-O2 | (7-1) | 7% |
| 6-HEB(2F,3F)-O2 | (6-6) | 6% |
| 3-HH1OCro(7F,8F)-5 | (10-6) | 5% |
| 3-HH1OB(2F,3F,6Me)-O2 | (11-7) | 5% |

NI = 85.9° C.; Δn = 0.089; η = 40.7 mPa · s; Δε = −4.1.

INDUSTRIAL APPLICABILITY

The invention provides a liquid crystal compound having an excellent compatibility with other liquid crystal materials and a large negative dielectric anisotropy (Δε).

The invention also provides a new liquid crystal composition including the liquid crystal compound as a component, and having features that are desired physical properties, by suitably selecting the rings, the substituents and so forth of the compound. It also provides a liquid crystal display device containing the liquid crystal composition.

The invention claimed is:

1. A compound represented by formula (1-1-1), (1-1-3), (1-1-4), or (1-1-6):

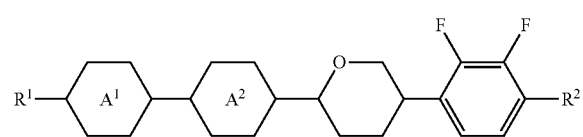
(1-1-1)

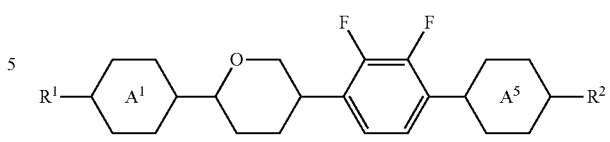
(1-1-4)

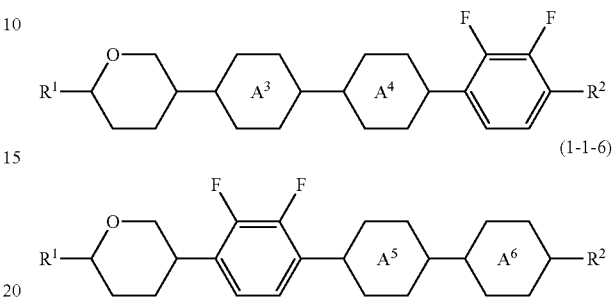
(1-1-3)

(1-1-6)

wherein

R$^1$ and R$^2$ are independently hydrogen, alkyl having 1 to 10 carbons or alkoxy having 1 to 9 carbons;

the ring A$^1$, the ring A$^2$, the ring A$^3$, the ring A$^4$, the ring A$^5$ and the ring A$^6$ are independently 1,4-cyclohexylene, 1,4-cyclohexenylene, 1,4-phenylene, 1,3-dioxane-2,5-diyl, pyrimidine-2,5-diyl, pyrimidine-3,6-diyl, pyridine-2,5-diyl or pyridine-3,6-diyl.

2. The compound according to claim 1, wherein in formula (1-1-1) according to claim 1, the ring A$^1$ and the ring A$^2$ are 1,4-cyclohexylene.

3. A compound represented by formula (1-1-2) or (1-2-2):

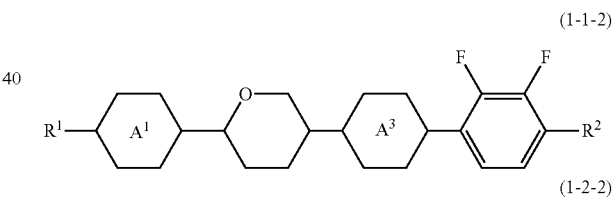
(1-1-2)

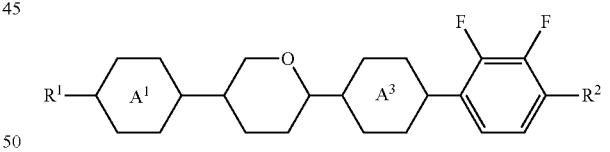
(1-2-2)

wherein R$^1$ and R$^2$ are independently hydrogen, alkyl having 1 to 10 carbons or alkoxy having 1 to 9 carbons; and the ring A$^1$ and the ring A$^3$ are independently 1,4-cyclohexylene, 1,4-cyclohexenylene, 1,4-phenylene, 1,3-dioxane-2,5-diyl, pyrimidine-2,5-diyl, pyrimidine-3,6-diyl, pyridine-2,5-diyl or pyridine-3,6-diyl.

4. The compound according to claim 3, wherein in formulas (1-1-2) and (1-2-2) according to claim 3, the ring A$^1$ and the ring A$^3$ are 1,4-cyclohexylene.

5. The compound according to claim 1, wherein in formulas (1-1-3) according to claim 1, the ring A$^3$ and the ring A$^4$ are 1,4-cyclohexylene.

6. The compound according to claim 1, wherein in formula (1-1-4) according to claim 1, the ring A$^1$ and the ring A$^5$ are 1,4-cyclohexylene.

7. A compound represented by formula (1-1-5) or (1-2-5):

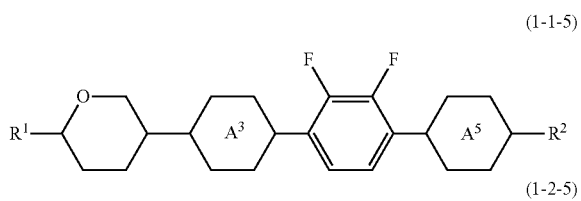

(1-1-5)

(1-2-5)

wherein $R^1$ and $R^2$ are independently hydrogen, alkyl having 1 to 10 carbons or alkoxy having 1 to 9 carbons; and the ring $A^3$ and the ring $A^5$ are independently 1,4-cyclohexylene, 1,4-cyclohexenylene, 1,4-phenylene, 1,3-dioxane-2,5-diyl, pyrimidine-2,5-diyl, pyrimidine-3,6-diyl, pyridine-2,5-diyl or pyridine-3,6-diyl.

8. The compound according to claim 7, wherein in formula (1-1-5) or (1-2-5) according to claim 7, the ring $A^3$ and the ring $A^5$ are 1,4-cyclohexylene.

9. The compound according to claim 1, wherein in formula (1-1-6) according to claim 1, the ring $A^5$ and the ring $A^6$ are 1,4-cyclohexylene.

10. A compound represented by any one of formulas (1-A) to (1-F):

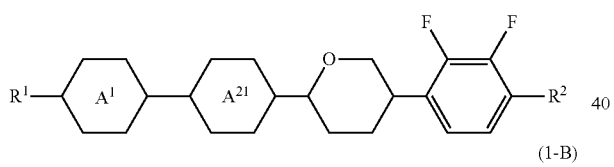

(1-A)

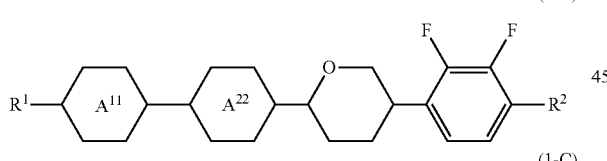

(1-B)

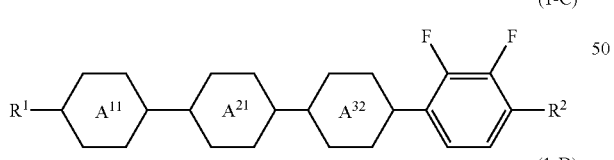

(1-C)

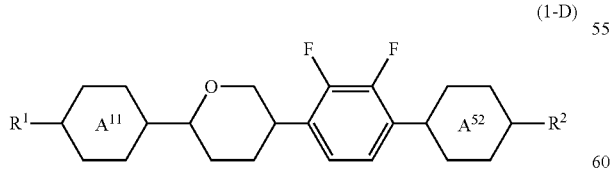

(1-D)

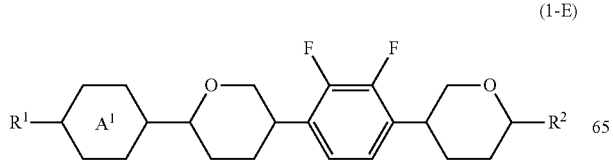

(1-E)

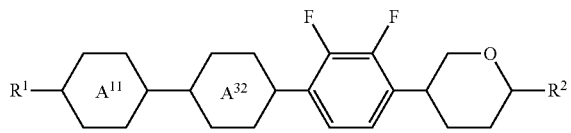

(1-F)

wherein
$R^1$ and $R^2$ are independently hydrogen, alkyl having 1 to 10 carbons or alkoxy having 1 to 9 carbons;
the ring $A^1$ is 1,4-cyclohexylene, 1,4-cyclohexenylene, 1,4-phenylene, tetrahydropyran-2,5-diyl, tetrahydropyran-3,6-diyl, 1,3-dioxane-2,5-diyl, pyrimidine-2,5-diyl, pyrimidine-3,6-diyl, pyridine-2,5-diyl or pyridine-3,6-diyl,
the ring $A^{11}$ and the ring $A^{21}$ are independently tetrahydropyran-2,5-diyl or tetrahydropyran-3,6-diyl; and
the ring $A^{22}$, the ring $A^{32}$ and the ring $A^{52}$ are independently 1,4-cyclohexylene, 1,4-cyclohexenylene, 1,4-phenylene, 1,3-dioxane-2,5-diyl, pyrimidine-2,5-diyl, pyrimidine-3,6-diyl, pyridine-2,5-diyl or pyridine-3,6-diyl.

11. The compound according to claim 10, wherein in formulas (1-A) to (1-F) according to claim 10, the ring $A^1$, the ring $A^{22}$, the ring $A^{32}$ and the ring $A^{52}$ are 1,4-cyclohexylene.

12. A liquid crystal composition including a first component and a second component, wherein the first component is at least one selected from compounds according to claim 1.

13. The liquid crystal composition according to claim 12, including at least one compound selected from the group of compounds represented by formulas (2) to (4) as the second component:

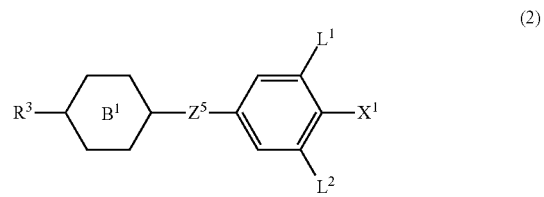

(2)

(3)

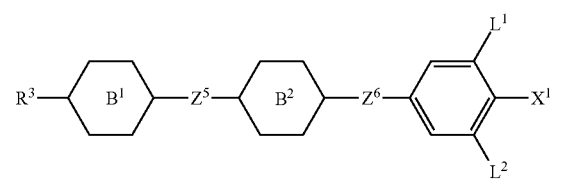

(4)

wherein
$R^3$ is independently alkyl having 1 to 10 carbons or alkenyl having 2 to 10 carbons, and in the alkyl and the alkenyl, at least one hydrogen may be replaced by fluorine and at least one —$CH_2$— may be replaced by —O—;

$X^1$ is independently fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

the ring B$^1$, the ring B$^2$ and the ring B$^3$ are independently 1,4-cyclohexylene, 1,3-dioxane-2,5-diyl, pyrimidine-2,5-diyl, tetrahydropyran-2,5-diyl or 1,4-phenylene in which at least one hydrogen may be replaced by fluorine;

$Z^5$ and $Z^6$ are independently —(CH$_2$)$_2$—, —(CH$_2$)$_4$—, —COO—, —CF$_2$O—, —OCF$_2$—, —CH=CH—, —C≡C—, —CH$_2$O— or a single bond; and $L^1$ and $L^2$ are independently hydrogen or fluorine.

hydrogen may be replaced by fluorine, 1,3-dioxane-2,5-diyl, tetrahydropyran-2,5-diyl or pyrimidine-2,5-diyl;

$Z^7$ is —(CH$_2$)$_2$—, —COO—, —CF$_2$O—, —OCF$_2$—, —C≡C—, —CH$_2$O— or a single bond;

$L^3$ and $L^4$ are independently hydrogen or fluorine; and o is 0, 1 or 2, and p is 0 or 1.

15. The liquid crystal composition according to claim 12, including at least one compound selected from the group of compounds represented by formulas (6) to (11) as the second component:

(6)
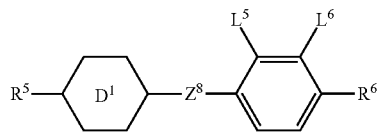

(7)
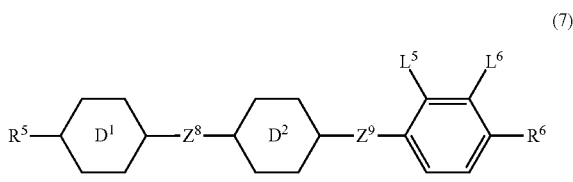

(8)
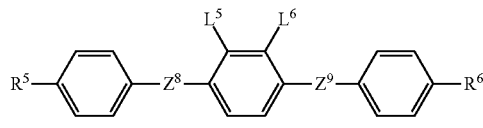

(9)
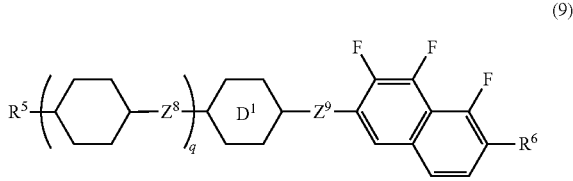

(10)
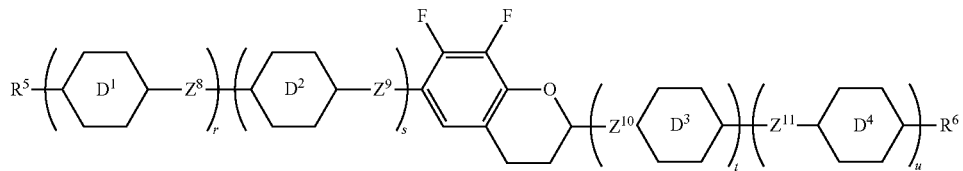

(11)
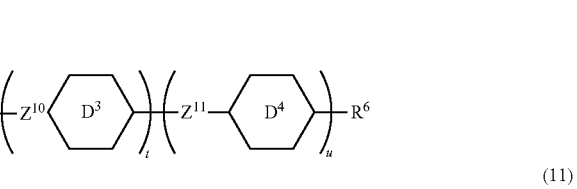

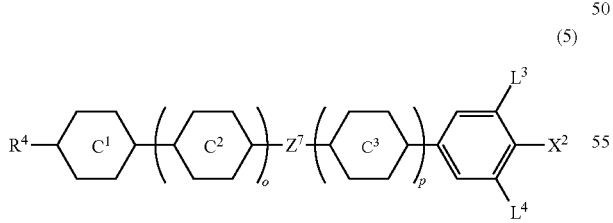

14. The liquid crystal composition according to claim 12, including at least one compound selected from the group of compounds represented by formula (5) as the second component:

(5)
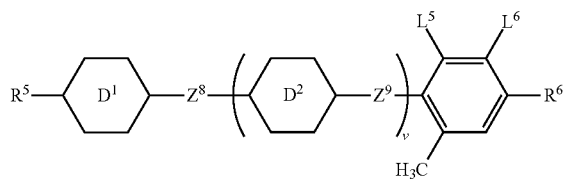

wherein

R$^4$ is alkyl having 1 to 10 carbons or alkenyl having 2 to 10 carbons, and in the alkyl and the alkenyl, at least one hydrogen may be replaced by fluorine and at least one —CH2— may be replaced by —O—;

X$^2$ is —C≡N or —C≡C—C≡N;

the ring C$^1$, the ring C$^2$ and the ring C$^3$ are independently 1,4-cyclohexylene, 1,4-phenylene in which at least one wherein R$^5$ and R$^6$ are independently alkyl having 1 to 10 carbons or alkenyl having 2 to 10 carbons, and in the alkyl or the alkenyl at least one —CH$_2$— may be replaced by —O—, and in the alkenyl at least one hydrogen may be replaced by fluorine;

the ring D$^1$, the ring D$^2$, the ring D$^3$ and the ring D$^4$ are independently 1,4-cyclohexylene, 1,4-cyclohexenylene, 1,4-phenylene in which at least one hydrogen may be replaced by fluorine or tetrahydropyran-2,5-diyl;

$Z^8$, $Z^9$, $Z^{10}$, and $Z^{11}$ are independently —(CH$_2$)$_2$—, —COO—, —CH$_2$O—, —OCF$_2$—, —OCF$_2$(CH$_2$)$_2$— or a single bond;

L$^5$ and L$^6$ are independently fluorine or chlorine; and q, r, s, t, u and v are independently 0 or 1, and the sum of r, s, t and u is 1 or 2.

16. The liquid crystal composition according to claim 12, including at least one compound selected from the group of compounds represented by formulas (12) to (14) as the second component:

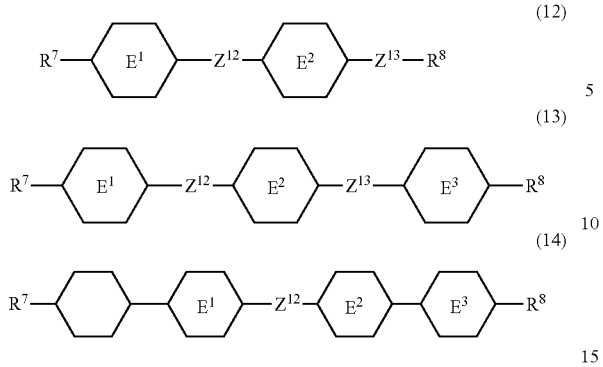

wherein
R⁷ and R⁸ are independently alkyl having 1 to 10 carbons or alkenyl having 2 to 10 carbons, and in the alkyl or the alkenyl at least one —CH$_2$— may be replaced by —O—, and in the alkenyl at least one hydrogen may be replaced by fluorine;
the ring E¹, the ring E² and the ring E³ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and
Z¹² and Z¹³ are independently —C≡C—, —COO—, —(CH$_2$)$_2$—, —CH=CH— or a single bond.

17. The liquid crystal composition according to claim 13, further including at least one compound selected from the group of compounds represented by formula (5):

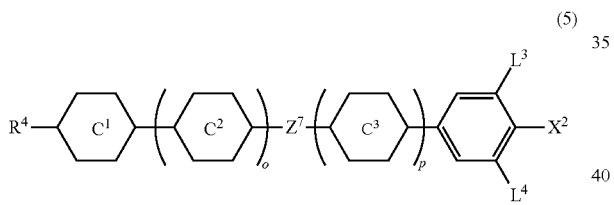

wherein
R⁴ is alkyl having 1 to 10 carbons or alkenyl having 2 to 10 carbons, and in the alkyl and the alkenyl, at least one hydrogen may be replaced by fluorine and at least one —CH$_2$— may be replaced by —O—;
X² is —C≡N or —C≡C—C≡N;
the ring C¹, the ring C² and the ring C³ are independently 1,4-cyclohexylene, 1,4-phenylene in which at least one hydrogen may be replaced by fluorine, 1,3-dioxane-2,5-diyl, tetrahydropyran-2,5-diyl or pyrimidine-2,5-diyl;
Z⁷ is —(CH$_2$)$_2$—, —COO—, —CF$_2$O—, —OCF$_2$—, —C≡C—, —CH$_2$O— or a single bond;
L³ and L⁴ are independently hydrogen or fluorine; and
o is 0, 1 or 2, and p is 0 or 1.

18. The liquid crystal composition according to claim 13, further including at least one compound selected from the group of compounds represented by formulas (12) to (14):

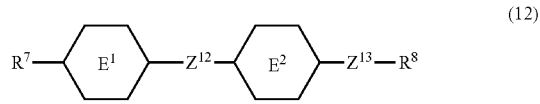

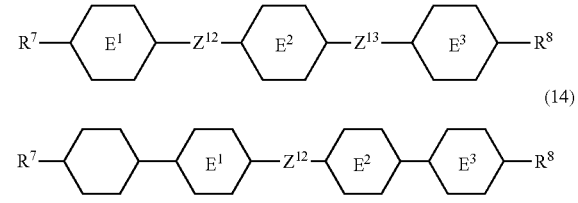

wherein
R⁷ and R⁸ are independently alkyl having 1 to 10 carbons or alkenyl having 2 to 10 carbons, and in the alkyl or the alkenyl at least one —CH$_2$— may be replaced by —O—, and in the alkenyl at least one hydrogen may be replaced by fluorine;
the ring E¹, the ring E² and the ring E³ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and
Z¹² and Z¹³ are independently —C≡C—, —COO—, —(CH$_2$)$_2$—, —CH=CH— or a single bond.

19. The liquid crystal composition according to claim 14, further including at least one compound selected from the group of compounds represented by formulas (12) to (14):

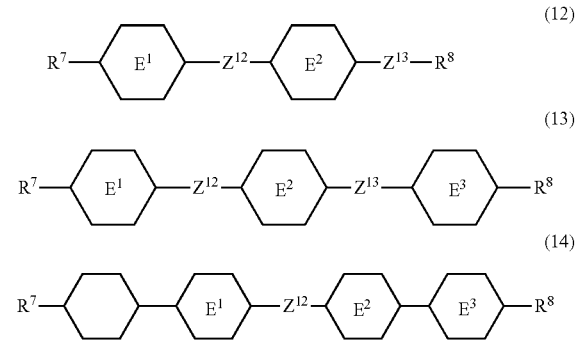

wherein
R⁷ and R⁸ are independently alkyl having 1 to 10 carbons or alkenyl having 2 to 10 carbons, and in the alkyl or the alkenyl at least one —CH$_2$— may be replaced by —O—, and in the alkenyl at least one hydrogen may be replaced by fluorine;
the ring E¹, the ring E² and the ring E³ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and
Z¹² and Z¹³ are independently —C≡C—, —COO—, —(CH$_2$)$_2$—, —CH=CH— or a single bond.

20. The liquid crystal composition according to claim 15, further including at least one compound selected from the group of compounds represented by formulas (12) to (14):

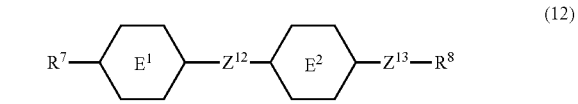

-continued

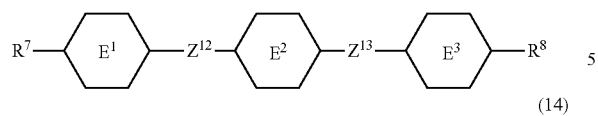
(13)

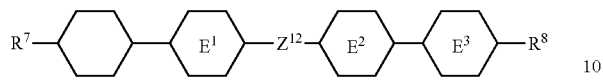
(14)

wherein
$R^7$ and $R^8$ are independently alkyl having 1 to 10 carbons or alkenyl having 2 to 10 carbons, and in the alkyl or the alkenyl at least one —$CH_2$— may be replaced by —O—, and in the alkenyl at least one hydrogen may be replaced by fluorine;

the ring $E^1$, the ring $E^2$ and the ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{12}$ and $^{13}$ are independently —C≡C—, —COO—, —$(CH_2)_2$—, —CH=CH— or a single bond.

21. The liquid crystal composition according to claim 12, further including at least one optically active compound and/or at least one polymerizable compound.

22. The liquid crystal composition according to claim 12, further including at least one antioxidant and/or at least one ultraviolet light absorber.

23. A liquid crystal display device containing the liquid crystal composition according to claim 12.

* * * * *